United States Patent
Benjamin et al.

(10) Patent No.: US 11,932,682 B2
(45) Date of Patent: Mar. 19, 2024

(54) **

(56) References Cited

U.S. PATENT DOCUMENTS

| | | | |
|---|---|---|---|
| 8,871,207 | B2 | 10/2014 | Lanzavecchia |
| 9,243,054 | B2 | 1/2016 | Burioni et al. |
| 9,340,603 | B2 | 5/2016 | Lanzavecchia |
| 10,442,854 | B2 | 10/2019 | Kallewaard-Lelay et al. |
| 2007/0219149 | A1 | 9/2007 | Hasegawa et al. |
| 2010/0080813 | A1 | 4/2010 | Lanzaveechia |
| 2011/0014187 | A1 | 1/2011 | Burioni et al. |
| 2012/0128684 | A1 | 5/2012 | Marasco et al. |
| 2017/0218054 | A1 | 8/2017 | Kallewaard-Lelay et al. |
| 2018/0155413 | A1 | 6/2018 | Kallewaard-Lelay et al. |
| 2019/0015509 | A1 | 1/2019 | Kallewaard-Lelay et al. |
| 2020/0109187 | A1 | 4/2020 | Kallewaard-Lelay et al. |

FOREIGN PATENT DOCUMENTS

| | | |
|---|---|---|
| CN | 103906763 A | 10/2016 |
| EP | 1167382 A1 | 1/2002 |
| EP | 2919813 B1 | 10/2018 |
| JP | A 2014-527403 A | 10/2014 |
| JP | A 2015-501815 A | 1/2015 |
| RU | 2366662 C2 | 9/2009 |
| RU | 2536956 C1 | 12/2014 |
| WO | 00/52031 A1 | 9/2000 |
| WO | 00/52473 A1 | 9/2000 |
| WO | 2004/001007 A1 | 12/2003 |
| WO | 2004/007667 A1 | 1/2004 |
| WO | 2005/007697 A1 | 1/2005 |
| WO | 2006/124269 A1 | 11/2006 |
| WO | 2007/045477 A1 | 4/2007 |
| WO | 2007/109742 A1 | 9/2007 |
| WO | 2007/117577 A1 | 10/2007 |
| WO | 2007/134327 A1 | 11/2007 |
| WO | 2008/028946 A1 | 3/2008 |
| WO | 2008/054606 A1 | 5/2008 |
| WO | 2008/066691 A1 | 5/2008 |
| WO | 2008/076379 A1 | 6/2008 |
| WO | 2008/084410 A1 | 7/2008 |
| WO | 2008/110937 A1 | 9/2008 |
| WO | 2009/115972 A1 | 9/2009 |
| WO | 2010/010466 A1 | 1/2010 |
| WO | 2010/010467 A1 | 1/2010 |
| WO | 2010/054007 A1 | 5/2010 |
| WO | 2012/082634 A1 | 6/2012 |
| WO | 2013/007770 A1 | 1/2013 |
| WO | 2013/011347 A1 | 1/2013 |
| WO | 2013/043729 A1 | 3/2013 |
| WO | 2013/044203 A1 | 3/2013 |
| WO | 2013/086052 A2 | 6/2013 |
| WO | 2013/132007 A1 | 9/2013 |
| WO | 2014/078268 A1 | 5/2014 |
| WO | 2014/158001 A1 | 10/2014 |
| WO | 2015/051010 A1 | 4/2015 |
| WO | 2016/011035 A2 | 1/2016 |
| WO | 2016/196470 A1 | 12/2016 |
| WO | 2017/123685 A1 | 7/2017 |
| WO | 2017/147248 A1 | 8/2017 |

OTHER PUBLICATIONS

GenBank Accession ACS95408, mmunoglobulin heavy chain variable region, partial [*Homo sapiens*], 2010.*

Benjamin et al., "A Broadly Neutralizing Human Monoclonal Antibody Directed against a Novel Conserved Epitope on the Influenza Virus H3 Hemagglutinin Globular Head," J Viral 88(12):6743-6750 (2014).

Biere et al., "Differentiation of Influenza B Virus Lineages Yamagata and Victoria by Real-Time PCR," J Clin Microbial 48: 1425-1427 (2010).

Chai et al., "A broadly protective therapeutic antibody against influenza B virus with two mechanisms of action," Nature Comm 8:14234 (2017).

Corti et al., "A Neutralizing Antibody Selected from Plasma Cells That Binds to Group 1 and Group 2 Influenza A Hemag-2Jutinins", Science (2011), 333 (6044):850-856.

Corti et al., "Cross-neutralization of four paramyxoviruses by a human monoclonal antibody", Nature (2013), 501(7467):439-443.

Corti, et al., "Heterosubtypic neutralizing antibodies are produced by individuals immunized with a seasonal influenza vaccine", The Journal of Clinical Investigation (2010), 120: 1663-1673.

Corti et al., "Tackling influenza with broadly neutralizing antibodies," Curr Opin Virol 24:60-69 (2017).

Dreyfus et al., "Highly Conserved Protective Epitopes on Influenza B Viruses", Science (2012), 337(6100): 1343-1348.

Ekiert et al., "Antibody recognition of a highly conserved influenza virus epitope: implications for universal prevention and therapy", Science (2009), 324 (5924):246-251.

Ekiert et al., "A Highly Conserved Neutralizing Epitope on Group 2 Influenza A Viruses", Science (2011), 333 (6044):843-850.

Ekiert et al., "Cross-neutralization of influenza A viruses mediated by a single antibody loop", Nature (2012), 489(7417):526-532.

Friesen et al., "A common solution to group 2 influenza virus neutralization," Proc Natl Acad Sci USA 111 (1):445-450 (2014).

Gen Bank Accession AAK94805, immunoglobulin light chain variable region, partial [*Homo sapiens*], Dec. 31, 2001.

Gen Bank Accession ACS95408, immunoglobulin heavy chain variable region, partial [*Homo sapiens*], Mar. 29, 2010.

Gerhard, Walter, "Prospects for Universal Influenza Virus Vaccine", Emerging Infectious Diseases (2006), 12(4):569-574.

Gioia et al., "Cross-subtype Immunity against Avian Influenza in Persons Recently Vaccinated for Influenza", Emerging Infectious Diseases (2008), 14(1):121-128.

Greenspan et al., "Defining epitopes: It's not as easy as it seems," Nature Biotechnol 17:936-937 (1999).

Hassantoufighi et al., "A practical influenza neutralization assay to simultaneously quantify hemagglutinin and neuraminidase-inhibiting antibody responses," Vaccine 28:790-797 (2010).

Kallewaard et al., "Structure and Function Analysis of an Antibody Recognizing All Influenza A Subtypes," 2016, Cell, vol. 166, pp. 596-608.

Kashyap et al., "Combinatorial antibody libraries from survivors of the Turkish H5NI avian influenza outbreak reveal virus neutralization strategies", PNAS (2008), 105(16):5986-5991.

Kaverin et al., "Epitope Mapping of the Hemagglutinin Molecule of a Highly Pathogenic H5NI Influenza Virus by Using Monoclonal Antibodies", Journal of Virology (2007), 81 (23): 12911-12917.

Kozbor et al., "The production of monoclonal antibodies from human lymphocytes", Immunology Today (1983), 4(3):72-79.

Krause et al., "A Broadly Neutralizing Human Monoclonal Antibody That Recognizes a Conserved, Novel Epitope on the Globular Head of the Influenza HINI Virus Hemagglutinin", Journal of Virology (2011), 85(20): 10905-10908.

Lee et al., "Heterosubtypic antibody recognition of the influenza virus hemagglutinin receptor binding site enhanced by avidity", PNAS (2012), 109( 42): 17040-17045.

Li et al., "Pandemic HINI influenza vaccine induces a recall response in humans that favors broadly cross-reactive memory B cells", PNAS (2012), 109(23):9047-9052.

Nakamura et al., "An In Vivo Human-Plasmablast Enrichment Technique Allows Rapid Identification of Therapeutic Influenza A Antibodies", Cell Host & Microbe (2013), 14:93-103.

Nguyen et al., "Heterosubtypic Immunity to Influenza A Virus Infection Requires B Cells but Not CDS+ Cytotoxic T Lymphocytes" (2001), 183:368-376.

Okuno et al., "A Common Neutralizing Epitope Conserved between the Hemagglutinins of Influenza A Virus HI and H2 Strains", Journal Of Virology, 67(5):2552-2558.

Pappas et al., "Rapid development of broadly influenza neutralizing antibodies through redundant mutations", Nature (2014), 516(7531)418-422.

Paul et al., eds. Fundamental Immunology 3rd Edition (1993), pp. 292-295.

Prabhu et al., "Monoclonal Antibodies against the Fusion Peptide of Hemagglutinin Protect Mice from Lethal Influenza A Virus H5NI Infection", Journal Of Virology (2009), 83(6):2553-2562.

(56) References Cited

OTHER PUBLICATIONS

Ren et al., "Epitope-focused vaccine design against influenza A and B viruses," Curr Opin Immunol 42:83-90 (2016).
Rowe et al., "Detection of Antibody to Avian Influenza A (H5NI) Virus in Human Serum by Using a Combination of Serologic Assays", Journal of Clinical Microbiology (1999), 37(4):937-943.
Rudikoff et al., "Single amino acid substitution altering antigen-binding specificity," Proc Natl Acad Sci USA 79(6):1979-1983 (1982).
Simmons et al., "Prophylactic and Therapeutic Efficacy of Human Monoclonal Antibodies against H5NI Influenza", PloS Medicine,m 4(5):el 78: 0928-0936 (2007).
Smirnov et al., "Prevention and treatment of bronchopneumonia in mice caused by mouse-adapted variant of avian H5N2 influenza A virus using monoclonal antibody against conserved epitope in the HA stem region", Archives of Virology, 145(8):1733-1741 (2000).
Sui et al., "Structural and fucntional bases for broad-spectrum neutralization of avian and human influenza A viruses", Nature Structural & Molecular Biology, 16(3):265-273 (2009).
Temperton et al., "Longitudinally Profiling Neutralizing Antibody Response to SARS Coronavirus with Pseudotypes", Emerging Infectious Diseases, 11(3):411-416 (2005).
Thompson et al., "Influenza-Associated Hospitalizations in the United States," JAMA 292:1333-1340 (2004).
Throsby et al., "Heterosubtypic Neutralizinig Monoclonal Antibodies Cross-Protective against H5NI and HINI Recovered from Human IgM+ Memory B Cells", PloS One, 3(12):e3942:pp. 1-15 (2008).
Traggiai, et al., An efficient method to make human monoclonal antibodies from memory B cells: potent neutralization of SARS coronavirus:, 10:871-875 (2004).
Vareckov et al., "HA2-specific monoclonal antibodies as tools for differential recognition of influenza A virus antigenic subtypes", Virus Research 132(1-2):181-186 (2008).
Wagner et al., "Bispecific antibody generated with sortase and click chemistry has broad antiinfluenza activity," Proc Natl Acad Sci USA 111(47):16820-16825 (2014).
Wang et al., Broadly Protective Monoclonal Antibodies against H3 Influenza Viruses following Sequential Immunization with Different Hemagglutinins, PLoS Pathogens, 6(2):e 1000796:pp. I-9 (2010).
Wang et al., "Crystal Structure of Unliganded Influenza B Virus Hemagglutinin," J Virol 82(6):3011-3020 (2008).
Whittle et al., "Broadly neutralizing human antibody that recognizes the receptor-binding pocket of influenza virus hemagglutinin", PNAS, 108(34): 14216-14221 (2011).
Wilson et al., "Structure of the hemagglutinin membrane glycoprotein of influenza virus at 3 A resolution," Nature 289:366-373 (1981).
Wrammert et al., "Broadly cross-reactive antibodies dominate the human B cell response against 2009 pandemic HINI influenza virus infection", Journal of Expermental Medicine,208:181-193 (2011).
Wrammert et al., "Rapid Cloning Of High Affinity Human Monoclonal Antibodies Against Influenza Virus", Nature, 453(7195):667-671 (2008).
Xiang et al., "Framework Residues 71 and 93 of the Chimeric B72.3 Antibody are Major Determinants of the Conformation of Heavy-chain Hypervariable Loops," J Mo/ Biol 253:385-390 (1995).
Yasugi et al., "Human Monoclonal Antibodies Broadly Neutralizing against Influenza B Virus," PLOS Pathog 9(2):e1003150 (2013).
Yoshida et al., "Cross-Protective Potential of a Novel Monoclonal Antibody Directed against Antigenic Site B of the Hemagglutinin of Influenza A Viruses", PloS Pathogens,5(3:e1000350 (2009).
Zabetakis et al., "Contributions of the Complementarity Determining Regions to the Thermal Stability of a Single-Domain Antibody," PLoS One 8(1 0):e77678 (2013).

Zhou et al., "Hospitalizations Associated With Influenza and Respiratory Syncytial Virus in the United States, 1993-2008," Clin Infect Dis 54(10):1427-1436.
European Search Opinion for corresponding EP 14 850 550.6.
International Search Report for corresponding PCT/US2014/058652 dated Jan. 9, 2015.
International Preliminary Report on Patentability with Written Opinion of the International Search Report for corresponding PCT/US2014/058652 dated Jan. 29, 2015.
Non-final Office Action issued in co-pending U.S. Appl. No. 15/325,603, dated Jun. 27, 2017.
Final Office Action issued in co-pending U.S. Appl. No. 15/325,603, dated Mar. 8, 2018.
Non-final Office Action issued in co-pending U.S. Appl. No. 15/325,603, dated Sep. 7, 2018.
Non-final Office Action issued in U.S. Appl. No. 15/577,799, dated Feb. 21, 2019.
Bouvier, "The Future of Influenza Vaccines: A Historical and Clinical Perspective," Vaccines 6:58 (2018).
Non-Final Office Action in U.S. Appl. No. 16/068,941, dated Oct. 21, 2019.
Abed et al., "A Review of Clinical Influenza A and B Infections with Reduced Susceptibility to Both Oseltamivir and Zanamivir," Open Forum Infectious Diseases 4(3): ofx105 (2017).
Ali et al., "Evaluation of MEDI8852, an Anti-Influenza A Monoclonal Antibody, in Treating Acute Uncomplicated Influenza," Antimicrobial Agents and Chemotherapy 62(11): e00694-18 (2018).
Deyev and Lebedenko, "Modern Technologies for Creating Synthetic Antibodies for Clinical Application," Acta Naturae 1: 32-50 (2009).
Ignatiev, "Features of the Antigenic Structure of Hemagglutinin Recognized by Antibodies Against Modern Influenza A Viruses of Subtypes H5 and H1," Abstract of Dissertation, Virology (2012).
Lin et al., "Recent Changes Among Human Influenza Viruses," Virus Research 103: 47-52 (2004).
Pan et al., "Weight-based Dosing in Medication Use: What Should We Know?" Patient Preference and Adherence 10: 549-560 (2016).
Office Action in Chinese Application No. 201580038244.1 dated Jan. 17, 2020.
Non-final Office Action in U.S. Appl. No. 16/560,040 dated Apr. 16, 2020.
Office Action in U.S. Appl. No. 16/068,941 dated Feb. 5, 2020.
Office Action in Chinese Application No. 201480053969.3 dated Feb. 3, 2020.
Office Action in Russian Application No. 2016117053 dated Aug. 14, 2018.
Office Action in Taiwanese Application No. 107146861 dated Feb. 5, 2020.
Office Action in Australian Application No. 2015289805 dated Feb. 19, 2020.
Office Action issued in Japanese Application No. 2017-523183 dated Aug. 20, 2019.
Office Action issued in Japanese Application 2017-523183 dated Feb. 18, 2020.
Office Action issued in European Application No. 16728534.5 dated Sep. 6, 2018.
Extended European Search Report for EP 17738889.9 dated Sep. 19, 2019.
Davies and Riechmann. "Affinity improvement of single antibody VH domains: residues in all three hypervariable regions affect antigen binding." Immunotechnology. 2:169-179 (1996).
Holt et al. "Domain antibodies: proteins for therapy." Trends Biotech. 21(11):484 (2003).

* cited by examiner

Figure 15

(Boxed positions: 18, 19, 42, 45)

| | 1–50 |
|---|---|
| WI05 HA2 | G I F G A I A G F I E N G W E G M V D G W Y G F R H Q N S E G I G Q A A D L K S T Q A A I N Q I N G |
| Pa99 HA2 | G I F G A I A G F I E N G W E G M V D G W Y G F R H Q N S E G T G Q A A D L K S T Q A A I N Q I N G |
| Aichi68 HA2 | G L F G A I A G F I E N G W E G M I D G W Y G F R H Q N S E G T G Q A A D L K S T Q A A I D Q I N G |
| HK68 HA2 | G L F G A I A G F I E N G W E G M I D G W Y G F R H Q N S E G T G Q A A D L K S T Q A A I D Q I N G |

| | 51–100 |
|---|---|
| WI05 HA2 | K L N R L I G K T N E K F H Q I E K E F S E V E G R I Q D L E K Y V E D T K I D L W S Y N A E L L V |
| Pa99 HA2 | K L N R L I E K T N E K F H Q I E K E F S E V E G R I Q D L E K Y V E D T K I D L W S Y N A E L L V |
| Aichi68 HA2 | K L N R V I E K T N E K F H Q I E K E F S E V E G R I Q D L E K Y V E D T K I D L W S Y N A E L L V |
| HK68 HA2 | K L N R V I E K T N E K F H Q I E K E F S E V E G R I Q D L E K Y V E D T K I D L W S Y N A E L L V |

| | 101–150 |
|---|---|
| WI05 HA2 | A L E N Q H T I D L T D S E M N K L F E R T K K Q L R E N A E D M G N G C F K I Y H K C D N A C I G |
| Pa99 HA2 | A L E N Q H T I D L T D S E M N K L F E R T K K Q L R E N A E D M G N G C F K I Y H K C D N A C I G |
| Aichi68 HA2 | A L E N Q H T I D L T D S E M N K L F E K T R R Q L R E N A E E M G N G C F K I Y H K C D N A C I E |
| HK68 HA2 | A L E N Q H T I D L T D S E M N K L F E K T R R Q L R E N A E D M G N G C F K I Y H K C D N A C I E |

| | 151–200 |
|---|---|
| WI05 HA2 | S I R N G T Y D H D V Y R D E A L N N R F Q I K G V E L K S G Y K D W I L W I S F A I S C F L L C V |
| Pa99 HA2 | S I R N G T Y D H D V Y R D E A L N N R F Q I K G V E L K S G Y K D W I L W I S F A I S C F L L C V |
| Aichi68 HA2 | S I R N G T Y D H D V Y R D E A L N N R F Q I K G V E L K S G Y K D W I L W I S F A I S C F L L C V |
| HK68 HA2 | S I R N G T Y D H D V Y R D E A L N N R F Q I K G V E L K S G Y K D W I L W I S F A I S C F L L C V |

| | 201–221 | |
|---|---|---|
| WI05 HA2 | A L L G F I M W A C Q K G N I R C N I C I | SEQ ID NO:169 |
| Pa99 HA2 | V L L G F I M W A C Q K G N I R C N I C I | SEQ ID NO:170 |
| Aichi68 HA2 | V L L G F I M W A C Q R G N I R C N I C I | SEQ ID NO:171 |
| HK68 HA2 | V L L G F I M W A C Q R G N I R C N I C I | SEQ ID NO:172 |

FIG. 18

VL Percent Identity

| | 1 | 2 | 3 | 3-GL | 4 | 5 | 6 | 7 | 8 | 9 | 10 | 11 | 12 | 13 | 14 | 15 | |
|---|---|---|---|---|---|---|---|---|---|---|---|---|---|---|---|---|---|
| 1 |  | 99.0 | 99.0 | 99.0 | 88.3 | 88.3 | 88.3 | 86.4 | 86.4 | 92.2 | 92.2 | 96.1 | 96.1 | 96.1 | 96.1 | 96.1 | 1 | Antibody 1
| 2 | 1.0 |  | 100.0 | 100.0 | 88.3 | 89.3 | 89.3 | 86.4 | 87.4 | 92.2 | 93.2 | 97.1 | 97.1 | 97.1 | 97.1 | 97.1 | 2 | Antibody 2
| 3 | 1.0 | 0.0 |  | 100.0 | 88.3 | 89.3 | 89.3 | 86.4 | 87.4 | 92.2 | 93.2 | 97.1 | 97.1 | 97.1 | 97.1 | 97.1 | 3 | Antibody 3
| 3-GL | 1.0 | 0.0 | 0.0 |  | 88.3 | 89.3 | 89.3 | 86.4 | 87.4 | 92.2 | 93.2 | 97.1 | 97.1 | 97.1 | 97.1 | 97.1 | 3-GL | Antibody 3-GL
| 4 | 11.7 | 11.7 | 11.7 | 11.7 |  | 99.0 | 99.0 | 85.4 | 84.5 | 87.4 | 86.4 | 85.4 | 85.4 | 85.4 | 85.4 | 85.4 | 4 | Antibody 4
| 5 | 11.7 | 10.5 | 10.5 | 10.5 | 1.0 |  | 100.0 | 84.5 | 85.4 | 86.4 | 87.4 | 86.4 | 86.4 | 86.4 | 86.4 | 86.4 | 5 | Antibody 5
| 6 | 11.7 | 10.5 | 10.5 | 10.5 | 1.0 | 0.0 |  | 84.5 | 85.4 | 86.4 | 87.4 | 86.4 | 86.4 | 86.4 | 86.4 | 86.4 | 6 | Antibody 6
| 7 | 15.0 | 15.0 | 15.0 | 15.0 | 15.2 | 16.4 | 16.4 |  | 99.0 | 88.3 | 87.4 | 83.5 | 83.5 | 83.5 | 83.5 | 83.5 | 7 | Antibody 7
| 8 | 15.0 | 13.9 | 13.9 | 13.9 | 16.4 | 15.2 | 15.2 | 1.0 |  | 87.4 | 88.3 | 84.5 | 84.5 | 84.5 | 84.5 | 84.5 | 8 | Antibody 8
| 9 | 8.2 | 8.2 | 8.2 | 8.2 | 12.8 | 14.0 | 14.0 | 12.7 | 13.9 |  | 99.0 | 89.3 | 89.3 | 89.3 | 89.3 | 89.3 | 9 | Antibody 9
| 10 | 8.2 | 7.1 | 7.1 | 7.1 | 14.0 | 12.8 | 12.8 | 13.9 | 12.7 | 1.0 |  | 90.3 | 90.3 | 90.3 | 90.3 | 90.3 | 10 | Antibody 10
| 11 | 4.0 | 3.0 | 3.0 | 3.0 | 15.2 | 14.0 | 14.0 | 18.7 | 17.5 | 11.5 | 10.4 |  | 99.0 | 99.0 | 99.0 | 99.0 | 11 | Antibody 11
| 12 | 4.0 | 3.0 | 3.0 | 3.0 | 15.2 | 14.0 | 14.0 | 18.7 | 17.5 | 11.5 | 10.4 | 1.0 |  | 99.0 | 99.0 | 100.0 | 12 | Antibody 12
| 13 | 4.0 | 3.0 | 3.0 | 3.0 | 15.2 | 14.0 | 14.0 | 18.7 | 17.5 | 11.5 | 10.4 | 1.0 | 2.0 |  | 99.0 | 98.1 | 13 | Antibody 13
| 14 | 4.0 | 3.0 | 3.0 | 3.0 | 15.2 | 14.0 | 14.0 | 18.7 | 17.5 | 11.5 | 10.4 | 0.0 | 1.0 | 1.0 |  | 99.0 | 14 | Antibody 14
| 15 | 4.0 | 3.0 | 3.0 | 3.0 | 15.2 | 14.0 | 14.0 | 18.7 | 17.5 | 11.5 | 10.4 | 1.0 | 0.0 | 2.0 | 1.0 |  | 15 | Antibody 15
| | 1 | 2 | 3 | 3-GL | 4 | 5 | 6 | 7 | 8 | 9 | 10 | 11 | 12 | 13 | 14 | 15 | |

Divergence

NEUTRALIZING ANTI-INFLUENZA A ANTIBODIES AND USES THEREOF

CROSS-REFERENCE TO RELATED APPLICATIONS

This application is a Divisional application of U.S. application Ser. No. 16/596,039, filed Oct. 8, 2019, which is a Divisional application of U.S. application Ser. No. 15/026,276, filed Mar. 31, 2016 and issued as U.S. Pat. No. 10,494,419, which is a U.S. National Stage application of International Application No. PCT/US2014/058652 filed on Oct. 1, 2014, said International Application No. PCT/US2014/058652 claims benefit under 35 U.S.C. § 119(e) of the U.S. Provisional Application Nos. 61/885,808, filed Oct. 2, 2013 and 62/002,414, filed May 23, 2014. Each of the above listed applications is incorporated by reference herein in its entirety for all purposes.

REFERENCE TO THE SEQUENCE LISTING

This application incorporates by reference a Sequence Listing submitted with this application as text file entitled 0098_0030 US3_SL, created on Oct. 20, 2021, and having a size of 92.0 kilobytes.

FIELD OF THE INVENTION

The invention relates to antibodies that have broad neutralizing activity against influenza A virus and to uses of such antibodies.

BACKGROUND TO THE INVENTION

Influenza viruses cause annual influenza epidemics and occasional pandemics, which pose a significant threat to public health worldwide. Seasonal influenza infection is associated with 200,000-500,000 deaths each year, particularly in young children, immunocompromised patients and the elderly. Mortality rates typically increase further during seasons with pandemic influenza outbreaks. There remains a significant unmet medical need to develop potent anti-viral therapeutics for preventing and treating influenza infections, particularly in under-served populations.

There are three types of influenza viruses, types A, B and C. Influenza A viruses can infect a wide variety of birds and mammals, including humans, pigs, chickens and ferrets. Influenza A viruses can be classified into subtypes based on allelic variations in antigenic regions of two genes that encode surface glycoproteins hemagglutinin (HA) and neuraminidase (NA). HA is the receptor-binding and membrane fusion glycoprotein, which mediates viral attachment and entry into target cells; HA is the primary target of protective humoral immune responses. The HA protein is trimeric in structure and is comprised of three identical copies of a single polypeptide precursor, HA0, which upon proteolytic maturation, is cleaved into a pH-dependent, metastable intermediate containing the globular head (HA1) and the stalk region (HA2). The membrane distal "globular head" constitutes the majority of the HA1 structure and contains the sialic acid binding pocket for viral entry and major antigenic domains. The membrane proximal "stalk" structure, assembled from HA2 and some HA1 residues, contains the fusion machinery, which undergoes a conformational change in the low pH environment of late endosomes to trigger membrane fusion and penetration into cells. The degree of sequence homology between influenza A subtypes is smaller in the HA1 (34%-59% homology between subtypes) than in the HA2 region (51%-80% homology). Neutralizing antibodies elicited by influenza virus infection are normally targeted to the variable HA1 globular head to prevent viral receptor binding and are usually strain-specific. Rarely, broad cross-reactive monoclonal antibodies have been identified that target the globular head of HA (Krause J. C. et al. 2011 J. Virol. 85; Whittle J. et al., 2011 PNAS 108; Ekiert D C et al., 2012 Nature 489; Lee P S et al., 2012 PNAS 109). In contrast, the structure of the stalk region is relatively conserved and a handful of broadly neutralizing antibodies have recently been identified that bind to HA stalk to prevent the pH-triggered fusion step for viral entry (Ekiert D. C. et al., 2009 Science 324; Sui J. et al., Nat Struct Mol Biol 16; Wrammert J et al., 2011 J Exp Med 208; Ekiert D. C et al., 2011 Science 333; *Corti* D et al., 2010 J Clin Invest 120; Throsby M., 2008 PLoS One 3). The majority of these stalk reactive neutralizing antibodies are either specific to influenza A group 1 viruses or specific to group 2 viruses. Very recently, stalk binding antibodies were isolated that were cross-reactive to both groups 1 and 2 viruses (Corti D. et al., 2011 Science 333; Li G M et al., 2012 PNAS 109 and Cyrille D et al., 2012 Science 337; Nakamura G et al., 2013, Cell Host & Microbe 14).

To date, there are no marketed antibodies that broadly neutralize or inhibit all influenza A virus infection or attenuate disease caused by influenza A virus. Therefore, there remains a need for new antibodies that protect against multiple group 1 and group 2 subtypes of influenza A virus.

DESCRIPTION OF THE INVENTION

The invention provides an antibody to influenza A virus or a binding fragment thereof that is capable of binding to influenza A virus hemagglutinin and neutralizing at least one group 1 subtype and at least 1 group 2 subtype of influenza A virus.

Preferably antibody or binding fragments of the invention are capable of binding to influenza A virus hemagglutinin and neutralizing at least 1, 2, 3, 4, 5, 6, 7, 8, 9 or 10 influenza A virus group 1 subtype and at least 1, 2, 3, 4, 5, or 6 influenza A virus group 2 subtypes. Further preferably, antibody or binding fragments of the invention are capable of binding to influenza A virus hemagglutinin and neutralizing at least 5 influenza A virus group 1 subtypes and at least 1 or 2 influenza A virus group 2 subtypes.

The hemagglutinin subtypes of influenza A viruses fall into two major phylogenetic groupings, identified as group 1, which includes subtypes H1, H2, H5, H6, H8, H9, H11, H12, H13, H16 and H17 and group 2, which includes subtypes H3, H4, H7, H10, H14, and H15. In one embodiment, an antibody or binding fragment according to the invention is capable of binding to and/or neutralizing one or more influenza A virus group 1 subtypes selected from H1, H2, H5, H6, H8, H9, H11, H12, H13, H16 and H17 and variants thereof and one or more influenza A virus group 2 subtype selected from H3, H4, H7, H10, H14 and H15 and variants thereof. In another embodiment, an antibody or binding fragment according to the invention is capable of binding to and/or neutralizing influenza A virus group 1 subtypes H1, H2, H5, H6, H8, H9, H11, H12, H13, H16 and H17 and influenza A virus group 2 subtypes H3, H4, H7, H10, H14 and H15. In another embodiment, the antibody or binding fragment is capable of binding to and/or neutralizing group 1 subtypes H1, H2, H5, H6, and H9 and group 2 subtypes H3 and H7. In a further embodiment, the antibody or binding fragment is capable of binding to and/or neutralizing group 1 subtypes H1, H2, H5 and H6 and group 2 subtypes H3 and H7.

The invention is based on isolation of a naturally-occurring human monoclonal antibody (mAb) from IgG memory B cells that were collected from individual donors as starting materials. Optimization was used to generate antibody variants with improved characteristics, as described herein. The optimized antibody variants are not naturally occurring; they are generated using recombinant techniques. Antibody or fragments thereof of the invention bind to the stalk region of HA and neutralize infection of more than one subtype of influenza A virus, selected from group 1 and group 2 subtypes, respectively. Antibodies of the invention, which are anti-Influenza A HA stalk-binding antibodies, demonstrated a broader breath of coverage or better neutralizing activity against influenza A viruses compared to an antibody from the published literature (Antibody Fl6v4, described in WO2013/011347A1) and shown in Table 6 of Example 5. Additionally, antibodies of the invention may be more effective than other mAb(s) in blocking HA maturation as shown in FIGS. 1B, 1C and 1D of Example 6.

In some embodiments, the antibody or binding fragment thereof includes a set of six CDRs in which the set of six CDRs is selected from the group consisting of:

(a) HCDR1 of SEQ ID NO.: 3, HCDR2 of SEQ ID NO.: 4, HCDR3 of SEQ ID NO.: 5, LCDR1 of SEQ ID NO.: 8, LCDR2 of SEQ ID NO.: 9 and LCDR3 of SEQ ID NO.: 10;

(b) HCDR1 of SEQ ID NO.: 13, HCDR2 of SEQ ID NO.: 14, HCDR3 of SEQ ID NO.: 15, LCDR1 of SEQ ID NO.: 18, LCDR2 of SEQ ID NO.: 19, LCDR3 of SEQ ID NO.: 20;

(c) HCDR1 of SEQ ID NO.: 23, HCDR2 of SEQ ID NO.: 24, HCDR3 of SEQ ID NO.: 25, LCDR1 of SEQ ID NO.: 28, LCDR2 of SEQ ID NO.: 29 and LCDR3 of SEQ ID NO.: 30;

(d) HCDR1 of SEQ ID NO.: 33, HCDR2 of SEQ ID NO.: 34, HCDR3 of SEQ ID NO.: 35, LCDR1 of SEQ ID NO.: 38, LCDR2 of SEQ ID NO.: 39 and LCDR3 of SEQ ID NO.: 40;

(e) HCDR1 of SEQ ID NO.: 43, HCDR2 of SEQ ID NO.: 44, HCDR3 of SEQ ID NO.: 45, LCDR1 of SEQ ID NO.: 48, LCDR2 of SEQ ID NO.: 49 and LCDR3 of SEQ ID NO.: 50;

(f) HCDR1 of SEQ ID NO.: 53, HCDR2 of SEQ ID NO.: 54, HCDR3 of SEQ ID NO.: 55, LCDR1 of SEQ ID NO.: 58, LCDR2 of SEQ ID NO.: 59 and LCDR3 of SEQ ID NO.: 60;

(g) HCDR1 of SEQ ID NO.: 63, HCDR2 of SEQ ID NO.: 64, HCDR3 of SEQ ID NO.: 65, LCDR1 of SEQ ID NO.: 68, LCDR2 of SEQ ID NO.: 69 and LCDR3 of SEQ ID NO.: 70;

(h) HCDR1 of SEQ ID NO.: 73, HCDR2 of SEQ ID NO.: 74, HCDR3 of SEQ ID NO.: 75, LCDR1 of SEQ ID NO.: 78, LCDR2 of SEQ ID NO.: 79 and LCDR3 of SEQ ID NO.: 80;

(i) HCDR1 of SEQ ID NO.: 83, HCDR2 of SEQ ID NO.: 84, HCDR3 of SEQ ID NO.: 85, LCDR1 of SEQ ID NO.: 88, LCDR2 of SEQ ID NO.: 89, LCDR3 of SEQ ID NO.: 90;

(j) HCDR1 of SEQ ID NO.: 93, HCDR2 of SEQ ID NO.: 94, HCDR3 of SEQ ID NO.: 95, LCDR1 of SEQ ID NO.: 98, LCDR2 of SEQ ID NO.: 99 and LCDR3 of SEQ ID NO.: 100;

(k) HCDR1 of SEQ ID NO.: 103, HCDR2 of SEQ ID NO.: 104, HCDR3 of SEQ ID NO.: 105, LCDR1 of SEQ ID NO.: 108, LCDR2 of SEQ ID NO.: 109 and LCDR3 of SEQ ID NO.: 110;

(l) HCDR1 of SEQ ID NO.: 113, HCDR2 of SEQ ID NO.: 114, HCDR3 of SEQ ID NO.: 115, LCDR1 of SEQ ID NO.: 118, LCDR2 of SEQ ID NO.: 119 and LCDR3 of SEQ ID NO.: 110;

(m) HCDR1 of SEQ ID NO.: 123, HCDR2 of SEQ ID NO.: 124, HCDR3 of SEQ ID NO.: 125, LCDR1 of SEQ ID NO.: 128, LCDR2 of SEQ ID NO.: 129 and LCDR3 of SEQ ID NO.: 130;

(n) HCDR1 of SEQ ID NO.: 133, HCDR2 of SEQ ID NO.: 134, HCDR3 of SEQ ID NO.: 135, LCDR1 of SEQ ID NO.: 138, LCDR2 of SEQ ID NO.: 139 and LCDR3 of SEQ ID NO.: 140; and (o) HCDR1 of SEQ ID NO.: 143, HCDR2 of SEQ ID NO.: 144, HCDR3 of SEQ ID NO.: 145, LCDR1 of SEQ ID NO.: 148, LCDR2 of SEQ ID NO.: 149 and LCDR3 of SEQ ID NO.: 150;

(p) a set of six CDRS according to any one of (a) to (o) comprising one or more amino acid substitutions, deletions or insertions;

(q) a set of six CDRS according to any one of (a) to (p) comprising 1, 2, 3, 4, 5, 6, 7, 8, 9, 10, 11, 12, 13, 14, 15, 16, 17, 18, 19, 20, 21, 22, 23, or 24 or 25 amino acid substitutions;

(r) a set of six CDRs HCDR1, HCDR2, HCDR3, LCDR1, LCDR2, LCDR3 according to any one of (a) to (q) comprising:

(i) a HCDR1 having an amino acid sequence identical to or comprising 3 or fewer amino acid residue substitutions relative to SEQ ID NO: 3;

(ii) a HCDR2 having an amino acid sequence identical to or comprising 5 or fewer amino acid residue substitutions relative to SEQ ID NO:4;

(iii) a HCDR3 having an amino acid sequence identical to or comprising 6 or fewer amino acid residue substitutions relative to SEQ ID NO:5;

(iv) a LCDR1 having an amino acid sequence identical to or comprising 5 or fewer amino acid residue substitutions and/or one deletion relative to SEQ ID NO:6;

(v) a LCDR2 having an amino acid sequence identical to or comprising 5 or fewer amino acid residue substitutions relative to SEQ ID NO:7; and (vi) a LCDR3 having an amino acid sequence identical to or comprising 1 or fewer amino acid residue substitutions relative to SEQ ID NO:8;

(s) a set of six CDRs HCDR1, HCDR2, HCDR3, LCDR1, LCDR2, LCDR3 according to any one of (a) to (r) comprising:

(i) a HCDR1 in which:
Kabat residue 31 is S,
Kabat residue 32 is N or Y,
Kabat residue 33 is N, S, or R,
Kabat residue 34 is A,
Kabat residue 35 is V or T,
Kabat residue 35A is W
Kabat residue 35B is N;

(ii) a HCDR2 in which:
Kabat residue 50 is R,
Kabat residue 51 is T,
Kabat residue 52 is Y,
Kabat residue 52A is Y,
Kabat residue 53 is R,
Kabat residue 54 is S,
Kabat residue 55 is K or G,
Kabat residue 56 is W, Kabat residue 57 is Y,
Kabat residue 58 is N or Y,
Kabat residue 59 is D,
Kabat residue 60 is Y,
Kabat residue 61 is A,
Kabat residue 62 is E, V or d,
Kabat residue 63 is S or F,
Kabat residue 64 is V or L,
Kabat residue 65 is K;
(iii) a HCDR3 in which:
Kabat residue 95 is S or G,
Kabat residue 96 is G,
Kabat residue 97 is H,
Kabat residue 98 is I,
Kabat residue 99 is T,
Kabat residue 100 is V or E,
Kabat residue 100A is F,
Kabat residue 100B is G,
Kabat residue 100C is V or L,
Kabat residue 100D is N,
Kabat residue 100E is V or I,
Kabat residue 100F is D,
Kabat residue 100G is A,
Kabat residue 100F is F or Y,
Kabat residue 101 is D,
Kabat residue 102 is M, I or V;
(iv) a LCDR1 in which:
Kabat residue 24 is R,
Kabat residue 25 is T, A or absent,
Kabat residue 26 is S or A,
Kabat residue 27 is Q,
Kabat residue 28 is S or R,
Kabat residue 29 is L,
Kabat residue 30 is S, N or R
Kabat residue 31 is S,
Kabat residue 32 is Y,
Kabat residue 33 is L, T or D,
Kabat residue 34 is H;
(v) a LCDR2 in which:
Kabat residue 50 is A,
Kabat residue 51 is A, T or S,
Kabat residue 52 is S or T,
Kabat residue 53 is S or T,
Kabat residue 54 is L or R,
Kabat residue 55 is Q, L or G,
Kabat residue 56 is S, and,
(vi) a LCDR3 in which:
Kabat residue 89 is Q,
Kabat residue 90 is Q or L,
Kabat residue 91 is S,
Kabat residue 92 is R, and
Kabat residue 93 is T.

The invention provides antibodies and binding fragments thereof comprising a set of six CDRs: HCDR1, HCDR2, HCDR3, LCDR1, LCDR2, LCDR3, wherein the set of six CDRs is shown in Tables 11 and 13.

Variant antibody sequences of the invention may share 75% or more (e.g., 80%, 85%, 90%, 95%, 97%, 98%, 99% or more) amino acid sequence identity with the sequences recited in the application. In some embodiments the sequence identity is calculated with regard to the full length of the reference sequence (i.e. the sequence recited in the application). In some further embodiments, percentage identity, as referred to herein, is as determined using BLAST version 2.1.3 using the default parameters specified by the NCBI (the National Center for Biotechnology Information; http://www.ncbi.nlm.nih.gov/) [Blosum 62 matrix; gap open penalty=1 1 and gap extension penalty=1].

Variant antibodies are also included within the scope of the invention. Thus, variants of the sequences recited in the application are also included within the scope of the invention. Variants of the antibody sequences having improved affinity and/or potency may be obtained using methods known in the art and are included within the scope of the invention. For example, amino acid substitutions may be used to obtain antibodies with further improved affinity. Alternatively, codon optimization of the nucleotide sequence may be used to improve the efficiency of translation in expression systems for the production of the antibody. Further, polynucleotides comprising a sequence optimized for antibody specificity or neutralizing activity by the application of a directed evolution method to any of the nucleic acid sequences of the invention are also within the scope of the invention.

The invention provides an antibody or binding fragment thereof according to the invention comprising a VH having at least 75% identity and/or a VL having at least 75% identity to a VH and/or VL selected from the group consisting of:
(a) VH of SEQ ID NO.: 2 and VL of SEQ ID NO.: 7,
(b) VH of SEQ ID NO.: 12 and VL of SEQ ID NO.: 17,
(c) VH of SEQ ID NO.: 22 and VL of SEQ ID NO.: 27,
(d) VH of SEQ ID NO.: 32 and VL of SEQ ID NO.: 37,
(e) VH of SEQ ID NO.: 42 and VL of SEQ ID NO.: 47,
(f) VH of SEQ ID NO.: 52 and VL of SEQ ID NO.: 57,
(g) VH of SEQ ID NO.: 62 and VL of SEQ ID NO.: 67,
(h) VH of SEQ ID NO.: 72 and VL of SEQ ID NO.: 77,
(i) VH of SEQ ID NO.: 82 and VL of SEQ ID NO.: 87,
(j) VH of SEQ ID NO.: 92 and VL of SEQ ID NO.: 97,
(k) VH of SEQ ID NO.: 102 and VL of SEQ ID NO.: 107,
(l) VH of SEQ ID NO.: 112 and VL of SEQ ID NO.: 117,
(m) VH of SEQ ID NO.: 122 and VL of SEQ ID NO.: 127,
(n) VH of SEQ ID NO.: 132 and VL of SEQ ID NO.: 137,
(o) VH of SEQ ID NO.: 144 and VL of SEQ ID NO.: 147 and
(p) VH of SEQ ID NO: 152 and VL of SEQ ID NO: 157.

An antibody or binding fragment thereof according to the invention may comprise a VH and a VL selected from the group consisting of:
(a) VH of SEQ ID NO.: 2 and VL of SEQ ID NO.: 7,
(b) VH of SEQ ID NO.: 12 and VL of SEQ ID NO.: 17,
(c) VH of SEQ ID NO.: 22 and VL of SEQ ID NO.: 27,
(d) VH of SEQ ID NO.: 32 and VL of SEQ ID NO.: 37,
(e) VH of SEQ ID NO.: 42 and VL of SEQ ID NO.: 47,
(f) VH of SEQ ID NO.: 52 and VL of SEQ ID NO.: 57,
(g) VH of SEQ ID NO.: 62 and VL of SEQ ID NO.: 67,
(h) VH of SEQ ID NO.: 72 and VL of SEQ ID NO.: 77,
(i) VH of SEQ ID NO.: 82 and VL of SEQ ID NO.: 87,
(j) VH of SEQ ID NO.: 92 and VL of SEQ ID NO.: 97,
(k) VH of SEQ ID NO.: 102 and VL of SEQ ID NO.: 107,
(l) VH of SEQ ID NO.: 112 and VL of SEQ ID NO.: 117,
(m) VH of SEQ ID NO.: 122 and VL of SEQ ID NO.: 127,
(n) VH of SEQ ID NO.: 132 and VL of SEQ ID NO.: 137,
(o) VH of SEQ ID NO.: 144 and VL of SEQ ID NO.: 147 and
(p) VH of SEQ ID NO: 152 and VL of SEQ ID NO: 157.

An antibody or binding fragment thereof according to the invention may be selected from the group consisting of: an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual-specific antibody, and a bispecific antibody.

An antibody or binding fragment thereof according to the invention may comprise a VH comprising a human germline framework, preferably VH6-1 and/or a VL comprising a human germline framework, preferably VK1-39. Preferably an antibody or binding fragment thereof according to the invention comprises a VH comprising human germline framework VH6-1 and a VL comprising a human germline framework VK1-39. The VH6 framework is rarely used in antibodies.

An antibody or binding fragment thereof according to the invention may comprise an Fc region, preferably the antibody is an IgG1, IgG2 or IgG4 or a binding fragment thereof.

In one embodiment, an antibody of the invention comprises a human IgG constant domain having one or more amino acid substitutions relative to a wild-type human IgG constant domain. An antibody of the invention may comprise a human IgG constant domain having the M252Y, S254T, and T256E ("YTE") amino acid substitutions, wherein amino acid residues are numbered according to the EU index as in Kabat.

The invention also provides an antibody to influenza A virus or a binding fragment thereof that is capable of binding to influenza A virus hemagglutinin and neutralizing at least one group 1 subtype and at least one group 2 subtype of influenza A virus characterized in that the antibody or binding fragment thereof competes for binding to influenza A virus hemagglutinin with an antibody of the invention, described above. Accordingly, the invention comprises an antibody, or fragment thereof, that binds to the same epitope as an antibody of the invention, or an antibody that competes for binding with an antibody of the invention.

The invention further provides an isolated nucleic acid encoding an antibody or fragment thereof according to the invention. Preferably, the nucleic acid is a cDNA. The invention also includes nucleic acid sequences encoding part or all of the light and heavy chains and CDRs of the antibodies of the present invention. Thus, provided herein are nucleic acid sequences encoding part or all of the light and heavy chains and CDRs of exemplary antibodies of the invention. The SEQ ID numbers for the nucleic acid sequences encoding the CDRs, heavy chain and light chain variable regions of the exemplary antibodies of the invention are provided. Due to the redundancy of the genetic code, variants of these sequences will exist that encode the same amino acid sequences.

The invention yet further provides a vector comprising an isolated nucleic acid according to the invention; preferably the vector is an expression vector.

Additionally, the invention provides a host cell comprising an isolated nucleic acid or a vector according to the invention. Suitable host cells include mammalian cell lines, such as those derived from HEK or CHO cells.

Further, the invention provides a method for manufacturing an antibody or fragment of the invention comprising culturing a host cell of the invention under conditions suitable for expression of the antibody or fragment thereof.

Such methods may further comprise isolating the antibody or fragment thereof from the host cell culture and optionally formulating the isolated antibody or fragment into a composition.

The invention yet further provides a composition comprising an antibody or fragment thereof according to the invention and a pharmaceutically acceptable carrier.

Also provided by the invention is a composition comprising an antibody or fragment thereof according to the invention, histidine and NaCl at a pH in the range of from about 5.5 to about 6.5, preferably at about pH 6.0; yet more preferably comprising an antibody or fragment thereof according to the invention, about 20 to about 30 mM histidine and about 0.1 to about 0.2 M NaCl, at a pH in the range of from about 5.5 to about 6.5, preferably at about pH 6.0; most preferably comprising 25 mM His and 0.15M NaCl at a pH in the range of from about 5.5 to about 6.5, for example, at about pH 6.0

Additionally, the invention provides:
- an antibody or fragment thereof according to the invention for use in the prophylaxis or treatment of influenza A infection in a subject;
- the use of an antibody or fragment thereof according to the invention in the manufacture of a medicament for the prophylaxis or treatment of Influenza A infection in a subject;
- a method for prophylaxis or treatment of Influenza A infection in a subject comprising administration of an antibody or fragment thereof according to the invention;
- the use of an antibody or fragment thereof according to the invention to prevent the pH-triggered fusion step for Influenza A viral entry into cells; or
- the use of an antibody or fragment thereof according to the invention to inhibit Influenza A virus HA maturation.

Exemplary antibodies of the invention include, but are not limited to: Antibody 3, Antibody 5, Antibody 6, Antibody 8, Antibody 10, Antibody 11, Antibody 12, Antibody 13, Antibody 14, and Antibody 15.

The invention also provides the use of an antibody or binding fragment thereof according to the invention in in vitro diagnosis of influenza A infection in a subject.

DETAILED DESCRIPTION

Introduction

The present invention provides antibodies, including human forms, as well as fragments, derivatives/conjugates and compositions thereof that bind to Influenza A virus hemagglutinin (HA) stalk and neutralize influenza A virus infection group 1 and group 2 subtypes as described herein; such anti-influenza A virus HA stalk antibodies are referred to herein as antibodies of the invention.

As used herein, the term "neutralize" refers to the ability of an antibody, or binding fragment thereof, to bind to an infectious agent, such as influenza A virus, and reduce the biological activity, for example, virulence, of the infectious agent. The minimal requirement for neutralization is the ability for the antibody, or binding fragment thereof, to bind to the infectious agent. In one embodiment, the antibody or binding fragment thereof of the invention immunospecifically binds at least one specified epitope or antigenic determinant of the Influenza A virus. In a more particular embodiment, the antibody or binding fragment thereof of the invention immunospecifically binds at least one specified epitope or antigenic determinant of the Influenza A virus HA stalk protein.

An antibody can neutralize the activity of an infectious agent, such as Influenza A virus at various points during the lifecycle of the virus. For example, an antibody may interfere with viral attachment to a target cell by interfering with the interaction of the virus and one or more cell surface receptors. Alternately, an antibody may interfere with one or more post-attachment interactions of the virus with its receptors, for example, by interfering with viral internalization by receptor-mediated endocytosis.

In one embodiment, the antibody or binding fragment thereof neutralizes the activity of Influenza A by interfering with the fusion process, for example, by interfering with fusion of the viral and endosomal membranes. In another embodiment, the antibody or binding fragment thereof interferes with protease mediated cleavage of HA0, thus interfering with viral maturation and the formation of the HA2 viral fusion peptide. For example, in one embodiment, the antibody or binding fragment thereof interferes with protease mediated HA0 cleavage, necessary for activation of the Influenza A virus.

As used herein, the terms "antibody" and "antibodies", also known as immunoglobulins, encompass monoclonal antibodies (including full-length monoclonal antibodies), human antibodies, humanized antibodies, camelid antibodies, chimeric antibodies, single-chain Fvs (scFv), single-chain antibodies, single domain antibodies, domain antibodies, Fab fragments, F(ab')2 fragments, antibody fragments that exhibit the desired biological activity (e.g. the antigen binding portion), disulfide-linked Fvs (dsFv), and anti-idiotypic (anti-Id) antibodies (including, e.g., anti-Id antibodies to antibodies of the invention), intrabodies, and epitope-binding fragments of any of the above. In particular, antibodies include immunoglobulin molecules and immunologically active fragments of immunoglobulin molecules, i.e., molecules that contain at least one antigen-binding site. Immunoglobulin molecules can be of any isotype (e.g., IgG, IgE, IgM, IgD, IgA and IgY), subisotype (e.g., IgG1, IgG2, IgG3, IgG4, IgA1 and IgA2) or allotype (e.g., Gm, e.g., G1m(f, z, a or x), G2m(n), G3m(g, b, or c), Am, Em, and Km(1, 2 or 3)).

Human antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains (CH). Each light chain has a variable domain at one end (VL) and a constant domain (CL) at its other end; the constant domain of the light chain is aligned with the first constant domain of the heavy chain, and the light chain variable domain is aligned with the variable domain of the heavy chain. Light chains are classified as either lambda chains or kappa chains based on the amino acid sequence of the light chain constant region. The variable domain of a kappa light chain may also be denoted herein as VK.

The antibodies of the invention include full length or intact antibody, antibody fragments, including antigen binding fragments, native sequence antibody or amino acid variants, human, humanized, post-translationally modified, chimeric or fusion antibodies, immunoconjugates, and functional fragments thereof. The antibodies can be modified in the Fc region to provide desired effector functions or serum half-life. As discussed in more detail in the sections below, with the appropriate Fc regions, the naked antibody bound on the cell surface can induce cytotoxicity, e.g., via antibody-dependent cellular cytotoxicity (ADCC) or by recruiting complement in complement dependent cytotoxicity (CDC), or by recruiting nonspecific cytotoxic cells that express one or more effector ligands that recognize bound antibody on the Influenza A virus HA stalk and subsequently cause phagocytosis of the cell in antibody dependent cell-mediated phagocytosis (ADCP), or some other mechanism. Alternatively, where it is desirable to eliminate or reduce effector function, so as to minimize side effects or therapeutic complications, certain other Fc regions may be used. The Fc region of the antibodies of the invention can be modified to increase the binding affinity for FcRn and thus increase serum half-life. Alternatively, the Fc region can be conjugated to PEG or albumin to increase the serum half-life, or some other conjugation that results in the desired effect.

The present anti-Influenza A virus HA stalk antibodies are useful for diagnosing, preventing, treating and/or alleviating one or more symptoms of the Influenza A virus infection in a mammal.

The invention provides a composition comprising an anti-Influenza A virus HA stalk antibody of the invention and a carrier. For the purposes of preventing or treating Influenza A virus infection, compositions can be administered to the patient in need of such treatment. The invention also provides formulations comprising an anti-Influenza A virus HA stalk antibody of the invention and a carrier. In one embodiment, the formulation is a therapeutic formulation comprising a pharmaceutically acceptable carrier.

In certain embodiments the invention provides methods useful for preventing or treating Influenza A infection in a mammal, comprising administering a therapeutically effective amount of the antibody to the mammal. The antibody therapeutic compositions can be administered short term (acutely), chronically, or intermittently as directed by physician.

In certain embodiments the invention also provides articles of manufacture comprising at least an anti-Influenza A virus HA stalk antibody, such as sterile dosage forms and kits. Kits can be provided which contain the antibodies for detection and quantitation of Influenza A virus in vitro, e.g. in an ELISA or a Western blot. Such antibody useful for detection may be provided with a label such as a fluorescent or radiolabel.

Terminology

Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise.

Unless defined otherwise, all technical and scientific terms used herein have the same meaning as commonly understood by one of ordinary skill in the art to which this invention is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this invention.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The numbering of amino acids in the variable domain, complementarity determining region (CDRs) and framework regions (FR), of an antibody follow, unless otherwise indicated, the Kabat definition as set forth in Kabat et al. Sequences of Proteins of Immunological Interest, 5th Ed.

Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insertion (residue 52a according to Kabat) after residue 52 of H2 and inserted residues (e.g. residues 82a, 82b, and 82c, etc., according to Kabat) after heavy chain FR residue 82. The Kabat numbering of residues may be determined for a given antibody by alignment at regions of homology of the sequence of the antibody with a "standard" Kabat numbered sequence. Maximal alignment of framework residues frequently requires the insertion of "spacer" residues in the numbering system, to be used for the Fv region. In addition, the identity of certain individual residues at any given Kabat site number may vary from antibody chain to antibody chain due to interspecies or allelic divergence.

Anti-Influenza a Virus HA Stalk Antibodies

In certain embodiments, the antibodies are isolated and/or purified and/or pyrogen free antibodies. The term "purified" as used herein, refers to other molecules, e.g., polypeptide, nucleic acid molecule that have been identified and separated and/or recovered from a component of its natural environment. Thus, in one embodiment the antibodies of the invention are purified antibodies wherein they have been separated from one or more components of their natural environment. The term "isolated antibody" as used herein refers to an antibody which is substantially free of other antibody molecules having different antigenic specificities (e.g., an isolated antibody that specifically binds to Influenza A virus HA stalk is substantially free of antibodies that specifically bind antigens other than those of Influenza A virus HA stalk). Thus, in one embodiment the antibodies of the invention are isolated antibodies wherein they have been separated from antibodies with a different specificity. Typically an isolated antibody is a monoclonal antibody. Moreover, an isolated antibody of the invention may be substantially free of one or more other cellular materials and/or chemicals and is herein referred to an isolated and purified antibody. In one embodiment of the invention, a combination of "isolated" monoclonal antibodies relates to antibodies having different specificities and being combined in a well-defined composition. Methods of production and purification/isolation of antibodies are described below in more detail.

The isolated antibodies of the present invention comprise antibody amino acid sequences disclosed herein encoded by any suitable polynucleotide, or any isolated or formulated antibody.

The antibodies of the invention immunospecifically bind at least one specified epitope specific to the Influenza A virus HA stalk protein. The term "epitope" as used herein refers to a protein determinant capable of binding to an antibody. Epitopes usually include chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

In one embodiment, the antibody or binding fragment thereof binds to an epitope that is conserved among at least H1, H2, H3, H4, H5, H6, H7, H8, H9, H10, H11, H12, H13, H14, H15, H16 or H17 or all influenza A HA subtypes. In another embodiment, the antibody or binding fragment thereof binds to an epitope that is conserved among one or more, or at least 1, 2, 3, 4, 5, 6, 7, 8, 9, or 10 influenza A virus group 1 subtypes selected from H1, H2, H5, H6, H8, H9, H11, H12, H13 and H16 and one or more, or at least 1, 2, 3, 4, 5, or 6 group 2 subtypes selected from H3, H4, H7, H10, H14 and H15.

In one embodiment, the antibody or binding fragment thereof binds at least 17H1, H2, H3, H4, H5, H6, H7, H8, H9, H10, H11, H12, H13, H14, H15, H16 or H17 or all influenza A subtypes with an ECK of between about 0.01 ug/ml and about 5 ug/ml, or between about 0.01 ug/ml and about 0.5 ug/ml, or between about 0.01 ug/ml and about 0.1 ug/ml, or less than about 5 ug/ml, 1 ug/ml, 0.5 ug/ml, 0.1 ug/ml, or 0.05 ug/ml. In another embodiment, the antibody or binding fragment thereof binds one or more, or at least 1, 2, 3, 4, 5, 6, 7, 8, 9, or 10 influenza A virus group 1 subtypes selected from H1, H2, H5, H6, H8, H9, H11, H12, H13 and H16 and one or more, or at least 1, 2, 3, 4, 5, or 6 group 2 subtypes selected from H3, H4, H7, H10, H14 and H15 with an ECK of between about 0.01 ug/ml and about 5 ug/ml, or between about 0.01 ug/ml and about 0.5 ug/ml, or between about 0.01 ug/ml and about 0.1 ug/ml, or less than about 5 ug/ml, 1 ug/ml, 0.5 ug/ml, 0.1 ug/ml, or 0.05 ug/ml.

In one embodiment, the antibody or binding fragment thereof recognizes an epitope that is either a linear epitope, or continuous epitope. In another embodiment, the antibody or binding fragment thereof recognizes a non-linear or conformational epitope. In one embodiment, the epitope is located in the highly conserved stalk region of HA2. In a more particular embodiment, the antibody or binding fragment binds to a conformational epitope in the highly conserved stalk region of HA2. In one embodiment, the epitope includes one or more amino acids selected from: positions 18, 19, 42, 45 in the stalk region of HA2 (positions are numbered according to H3 numbering system as described in Weiss et al., J. Mol. Biol. (1990) 212, 737-761 (1990)) as contact residues. In a more particular embodiment, the epitope includes one or more amino acids selected from 18, 19, 42 and 45 in the stalk region of HA2 as contact residues. In a further embodiment, the epitope includes amino acids 18, 19, 42 and 45 in the stalk region of HA2 as contact residues. In yet a further embodiment, the epitope includes amino acids 18, 19, and 42 in the stalk region of HA2 as contact residues.

The epitope or epitopes recognized by the antibody or binding fragment thereof of the invention may have a number of uses. For example, the epitope in purified or synthetic form can be used to raise immune responses (i.e., as a vaccine, or for the production of antibodies for other uses) or for screening sera for antibodies that immunoreact with the epitope. In one embodiment, an epitope recognized by the antibody or binding fragment thereof of the invention, or an antigen having such an epitope may be used as a vaccine for raising an immune response. In another embodiment, the antibodies and binding fragments of the invention can be used to monitor the quality of vaccines, for example, by determining whether the antigen in a vaccine contains the correct immunogenic epitope in the correct conformation.

Variable Regions

As used herein, the term "parent antibody" refers to an antibody which is encoded by an amino acid sequence used for the preparation of the variant or derivative, defined herein. The parent polypeptide may comprise a native antibody sequence (i.e., a naturally occurring, including a naturally occurring allelic variant) or an antibody sequence with pre-existing amino acid sequence modifications (such as other insertions, deletions and/or substitutions) of a naturally occurring sequence. The parent antibody may be a humanized antibody or a human antibody. In specific embodiments, antibodies of the invention are variants of the parent antibody. As used herein, the term "variant" refers to an antibody, which differs in amino acid sequence from a "parent" antibody amino acid sequence by virtue of addition, deletion and/or substitution of one or more amino acid residue(s) in the parent antibody sequence.

The antigen-binding portion of an antibody comprises one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

Antibodies of the invention comprise at least one antigen binding domain, comprising a VH and a VL domain described herein.

In certain embodiments, the purified antibodies comprise a VH and/or VL that has a given percent identify to at least one of the VH and/or VL sequences disclosed in Table 1 As used herein, the term "percent (%) sequence identity", also including "homology" is defined as the percentage of amino acid residues or nucleotides in a candidate sequence that are identical with the amino acid residues or nucleotides in the reference sequences, such as parent antibody sequence, after aligning the sequences and introducing gaps, if necessary, to achieve the maximum percent sequence identity, and not considering any conservative substitutions as part of the sequence identity. Optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

Antibodies of the invention may comprise a VH amino acid sequence having at least 65%, 70%, 75%, 80%, 85%, 90%, 95% or having 100% identity to the VH amino acid sequences described herein. The antibodies may have a VH amino acid sequence having at least, 90%, 91%, 92%, 93%, 94%, 95%, 96%, 97%, 98%, 99% or having 100% identity to the amino acid sequence of the VH amino acid sequences described herein.

Antibodies of the invention may comprise a VL amino acid sequence having at least 65%, 70%, 75%, 80%, 85%, 90%, 95% or having 100% identity to the VL amino acid sequences described herein. The antibodies may have a VL amino acid sequence having at least, 90%, 91%, 92%, 93%, 94%, 95%, 96%, 97%, 98%, 99% or having 100% identity to the VL amino acid sequences described herein.

Antibodies within the scope of the of the invention are capable of neutralizing one or more group 1 subtype and one or more group 2 subtype of Influenza A virus, as described herein.

Complementarity Determining Regions (CDRs)

While the variable domain (VH and VL) comprises the antigen-binding region; the variability is not evenly distributed through the variable domains of antibodies. It is concentrated in segments called Complementarity Determining Regions (CDRs), both in the light chain (VL or VK) and the heavy chain (VH) variable domains. The more highly conserved portions of the variable domains are called the framework regions (FR). The variable domains of native heavy and light chains each comprise four FR, largely adopting a β-sheet configuration, connected by three CDRs, which form loops connecting, and in some cases forming part of, the β-sheet structure. The CDRs in each chain are held together in close proximity by the FR and, with the CDRs from the other chain, contribute to the formation of the antigen-binding site of antibodies (see, Kabat et al., Supra). The three CDRs of the heavy chain are designated CDR-H1, CDR-H2, and CDR-H3, and the three CDRs of the light chain are designated CDR-L1, CDR-L2, and CDR-L3. The Kabat numbering system is used herein. As such, CDR-H1 begins at approximately amino acid 31 (i.e., approximately 9 residues after the first cysteine residue), includes approximately 5-7 amino acids, and ends at the next tyrosine residue. CDR-H2 begins at the fifteenth residue after the end of CDR-H1, includes approximately 16-19 amino acids, and ends at the next arginine or lysine residue. CDR-H3 begins at approximately the thirty third amino acid residue after the end of CDR-H2; includes 3-25 amino acids; and ends at the sequence W-G-X-G, where X is any amino acid. CDR-L1 begins at approximately residue 24 (i.e., following a cysteine residue); includes approximately 10-17 residues; and ends at the next tyrosine residue. CDR-L2 begins at approximately the sixteenth residue after the end of CDR-L1 and includes approximately 7 residues. CDR-L3 begins at approximately the thirty third residue after the end of CDR-L2; includes approximately 7-11 residues and ends at the sequence F-G-X-G, where X is any amino acid. Note that CDRs vary considerably from antibody to antibody (and by definition will not exhibit homology with the Kabat consensus sequences).

The present invention encompasses neutralizing anti-Influenza A HA stalk antibodies comprising amino acids in a sequence that is substantially the same as an amino acid sequence described herein. Amino acid sequences that are substantially the same as the sequences described herein include sequences comprising conservative amino acid substitutions, as well as amino acid deletions and/or insertions in an amino acid sequence of for example, Antibody 11, Antibody 12, Antibody 13, Antibody 14 or Antibody 15, or in an amino acid sequence shown in SEQ ID NOs: 102, 112, 122, 132, or 142. A conservative amino acid substitution refers to the replacement of a first amino acid by a second amino acid that has chemical and/or physical properties (e.g, charge, structure, polarity, hydrophobicity/hydrophilicity) that are similar to those of the first amino acid. Conservative substitutions include replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

Framework Regions

The variable domains of the heavy and light chains each comprise four framework regions (FR1, FR2, FR3, FR4), which are the more highly conserved portions of the variable domains. The four FRs of the heavy chain are designated FR-H1, FR-H2, FR-H3 and FR-H4, and the four FRs of the light chain are designated FR-L1, FR-L2, FR-L3 and FR-L4. The Kabat numbering system is used herein, See Table 1, Kabat et al, Supra. As such, FR-H1 begins at position 1 and ends at approximately amino acid 30, FR-H2 is approximately from amino acid 36 to 49, FR-H3 is approximately from amino acid 66 to 94 and FR-H4 is approximately amino acid 103 to 113. FR-L1 begins at amino acid 1 and ends at approximately amino acid 23, FR-L2 is approximately from amino acid 35 to 49, FR-L3 is approximately from amino acid 57 to 88 and FR-L4 is approximately from amino acid 98 to 107. In certain embodiments the framework regions may contain substitutions according to the Kabat numbering system, e.g., insertion at 106A in FR-L1. In addition to naturally occurring substitutions, one or more alterations (e.g., substitutions) of FR residues may also be introduced in an antibody of the invention, provided it retains neutralizing ability. In certain embodiments, these result in an improvement or optimization in the binding affinity of the antibody for Influenza A virus HA stalk. Examples of framework region residues to modify include those which non-covalently bind antigen directly (Amit et al., Science, 233:747-753 (1986)); interact with/effect the conformation of a CDR (Chothia et al., J. Mol. Biol., 196:901-917 (1987)); and/or participate in the VL-VH interface (U.S. Pat. No. 5,225,539).

In another embodiment the FR may comprise one or more amino acid changes for the purposes of "germlining". For example, the amino acid sequences of selected antibody heavy and light chains are compared to germline heavy and light chain amino acid sequences and where certain framework residues of the selected VL and/or VH chains differ from the germline configuration (e.g., as a result of somatic mutation of the immunoglobulin genes used to prepare the phage library), it may be desirable to "back-mutate" the altered framework residues of the selected antibodies to the germline configuration (i.e., change the framework amino acid sequences of the selected antibodies so that they are the same as the germline framework amino acid sequences). Such "back-mutation" (or "germlining") of framework residues can be accomplished by standard molecular biology methods for introducing specific mutations (e.g., site-directed mutagenesis; PCR-mediated mutagenesis, and the like).

Nucleotide Sequences Encoding Antibodies of the Invention

In addition to the amino acid sequences described above, the invention further provides nucleotide sequences corresponding to the amino acid sequences and encoding for the human antibodies of the invention. In one embodiment, the invention provides polynucleotides comprising a nucleotide sequence encoding an antibody described herein or fragments thereof. These include, but are not limited to, nucleotide sequences that code for the above referenced amino acid sequences. Thus, the present invention also provides polynucleotide sequences encoding VH and VL framework regions including CDRs and FRs of antibodies described herein as well as expression vectors for their efficient expression in cells (e.g. mammalian cells). Methods of making the antibodies using polynucleotides are described below in more detail.

The invention also encompasses polynucleotides that hybridize under stringent or lower stringency hybridization conditions, e.g., as defined herein, to polynucleotides that encode an antibody of the invention described herein. The term "stringency" as used herein refers to experimental conditions (e.g. temperature and salt concentration) of a hybridization experiment to denote the degree of homology between the probe and the filter bound nucleic acid; the higher the stringency, the higher percent homology between the probe and filter bound nucleic acid.

Stringent hybridization conditions include, but are not limited to, hybridization to filter-bound DNA in 6× sodium chloride/sodium citrate (SSC) at about 45° C. followed by one or more washes in 0.2×SSC/0.1% SDS at about 50-65° C., highly stringent conditions such as hybridization to filter-bound DNA in 6×SSC at about 45° C. followed by one or more washes in 0.1×SSC/0.2% SDS at about 65° C., or any other stringent hybridization conditions known to those skilled in the art (see, for example, Ausubel, F. M. et al., eds. 1989 Current Protocols in Molecular Biology, vol. 1, Green Publishing Associates, Inc. and John Wiley and Sons, Inc., NY at pages 6.3.1 to 6.3.6 and 2.10.3).

Substantially identical sequences may be polymorphic sequences, i.e., alternative sequences or alleles in a population. An allelic difference may be as small as one base pair. Substantially identical sequences may also comprise mutagenized sequences, including sequences comprising silent mutations. A mutation may comprise one or more residue changes, a deletion of one or more residues, or an insertion of one or more additional residues.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

A polynucleotide encoding an antibody may also be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably polyA+ RNA, isolated from, any tissue or cells expressing the antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY), to generate antibodies having a different amino acid sequence, for example to create amino acid substitutions, deletions, and/or insertions.

Binding Characteristics

As described above, the anti-Influenza A virus HA stalk antibodies of the invention immunospecifically bind at least one specified epitope or antigenic determinants of the Influenza A virus HA stalk protein, peptide, subunit, fragment, portion or any combination thereof either exclusively or preferentially with respect to other polypeptides. The term "epitope" or "antigenic determinant" as used herein refers to a protein determinant capable of binding to an antibody, wherein the term "binding" herein preferably relates to a specific binding. These protein determinants or epitopes usually consist of chemically active surface groupings of molecules such as amino acids or sugar side chains and usually have a specific three dimensional structural characteristics, as well as specific charge characteristics. Conformational and non-conformational epitopes are distinguished in that the binding to the former but not the latter is lost in the presence of denaturing solvents. The term "discontinuous epitope" as used herein, refers to a conformational epitope on a protein antigen which is formed from at least two separate regions in the primary sequence of the protein.

The interactions between antigens and antibodies are the same as for other non-covalent protein-protein interactions. In general, four types of binding interactions exist between antigens and antibodies: (i) hydrogen bonds, (ii) dispersion forces, (iii) electrostatic forces between Lewis acids and Lewis bases, and (iv) hydrophobic interactions. Hydrophobic interactions are a major driving force for the antibody-antigen interaction, and are based on repulsion of water by non-polar groups rather than attraction of molecules (Tanford, 1978). However, certain physical forces also contribute to antigen-antibody binding, for example, the fit or complimentary of epitope shapes with different antibody binding sites. Moreover, other materials and antigens may cross-react with an antibody, thereby competing for available free antibody.

Measurement of the affinity constant and specificity of binding between antigen and antibody is a pivotal element in determining the efficacy of prophylactic, therapeutic, diagnostic and research methods using the antibodies of the invention. "Binding affinity" generally refers to the strength of the sum total of the noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the equilibrium dissociation constant (Kd), which is calculated as the ratio $k_{off}/k_{on}$. See, e.g., Chen, Y., et al., (1999) *J. Mol Biol* 293:865-881. Affinity can be measured by common methods known in the art, including those described and exemplified herein. An example of a commercially available system for kinetic characterization includes the OCTET® family of instruments. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

Determination of binding affinity can be measured using the specific techniques described further in the Example section, and methods well known in the art. One such method includes measuring the disassociation constant "Kd" by a radiolabeled antigen binding assay (RIA) performed with the Fab version of an antibody of interest and its antigen as described by the following assay that measures solution binding affinity of Fabs for antigen by equilibrating Fab with a minimal concentration of ($^{125}$I)-labeled antigen in the presence of a titration series of unlabeled antigen, then capturing bound antigen with an anti-Fab antibody-coated plate (Chen, et al., (1999) *J. Mol Biol* 293:865-881). To establish conditions for the assay, microtiter plates (Dynex) are coated overnight with 5 μg/ml of a capturing anti-Fab antibody (Cappel Labs) in 50 mM sodium carbonate (H 9.6), and subsequently blocked with 2% (w/v) bovine serum albumin in PBS for two to five hours at room temperature (approximately 23° C.). In a non-adsorbant plate (Nunc #269620), 100 pM or 26 pM [$^{125}$I]-antigen are mixed with serial dilutions of a Fab of interest (e.g., consistent with assessment of an anti-VEGF antibody, Fab-12, in Presta et al., (1997) *Cancer Res.* 57:4593-4599). The Fab of interest is then incubated overnight; however, the incubation may continue for a longer period (e.g., 65 hours) to insure that equilibrium is reached. Thereafter, the mixtures are transferred to the capture plate for incubation at room temperature (e.g., for one hour). The solution is then removed and the plate washed eight times with 0.1% Tween-20 in PBS. When the plates have dried, 150 μl/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays.

In another instance the Kd value may be measured by using surface plasmon resonance assays using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 110 mM sodium acetate, pH 4.8, into 5 ug/ml (~0.2 uM) before injection at a flow rate of 5 ul/minute to achieve approximately 10 response units (RU) of coupled protein. Following the injection of antigen, IM ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 ul/min. Association rates ($k_{on}$) and dissociation rates ($k_{off}$) are calculated using a simple one-to-one Langmuir binding model (BIAcore Evaluation Software version 3.2) by simultaneously fitting the association and dissociation sensorgram.

If the on-rate exceeds $10^6$ $M^{-1}$ $S^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stir red cuvette. An "on-rate" or "rate of association" or "association rate" or "$k_{on}$" according to this invention can also be determined with the same surface plasmon resonance technique described above using a BIAcore™-2000 or a BIAcore™-3000 (BIAcore, Inc., Piscataway, N.J.) as described above.

Methods and reagents suitable for determination of binding characteristics of an antibody of the present invention, or an altered/mutant derivative thereof (discussed below), are known in the art and/or are commercially available (U.S. Pat. Nos. 6,849,425; 6,632,926; 6,294,391; 6,143,574). Moreover, equipment and software designed for such kinetic analyses are commercially available (e.g. Biacore® A100, and Biacore® 2000 instruments; Biacore International AB, Uppsala, Sweden).

In one embodiment, antibodies of the present invention, including binding fragments or variants thereof, may also be described or specified in terms of their binding affinity for Influenza A virus polypeptides. Typically, antibodies with high affinity have Kd of less than $10^{-7}$ M. In one embodiment, antibodies or binding fragments thereof bind Influenza A polypeptides, or fragments or variants thereof, with a dissociation constant or Kd of less than or equal to $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M or $10^{-15}$ M. Influenza A polypeptides can include HA polypeptides. In a more particular embodiment, antibodies or binding fragments thereof bind Influenza A polypeptides, or fragments or variants thereof, with a dissociation constant or Kd of less than or equal to $5 \times 10^{-10}$ M, $10^{-10}$ M, $5 \times 10^{-11}$ M, $10^{-11}$ M, $5 \times 10^{-12}$ M or $10^{-12}$ M. The invention encompasses antibodies that bind Influenza A polypeptides with a dissociation constant or Kd that is within a range between any of the individual recited values.

In another embodiment, antibodies or binding fragments thereof of the invention bind Influenza A polypeptides or fragments or variants thereof with an off rate ($k_{off}$) of less than or equal to $5 \times 10^{-2}$ $sec^{-1}$, $10^{-2}$ $sec^{-1}$, $5 \times 10^{-3}$ $sec^{-1}$ or $10^{-3}$ $sec^{-1}$, $5 \times 10^{-4}$ $sec^{-1}$, $10^{-4}$ $sec^{-1}$, $5 \times 10^{-5}$ $sec^{-1}$, or $10^{-5}$ $sec^{-1}$, $5 \times 10^{-6}$ $sec^{-1}$, $10^{-6}$ $sec^{-1}$, $5 \times 10^{-7}$ $sec^{-1}$ or $10^{-7}$ $sec^{-1}$. In a more particular embodiment, antibodies or binding fragments thereof of the invention bind Influenza A polypeptides or fragments or variants thereof with an off rate ($k_{off}$) less than or equal to $5 \times 10^{-4}$ $sec^{-1}$, $10^{-4}$ $sec^{-1}$, $5 \times 10^{-5}$ $sec^{-1}$, or $10^{-5}$ $sec^{-1}$, $5 \times 10^{-6}$ $sec^{-1}$, $10^{-6}$ $sec^{-1}$, $5 \times 10^{-7}$ $sec^{-1}$ or $10^{-7}$ $sec^{-1}$. The invention also encompasses antibodies that bind Influenza A polypeptides with an off rate ($k_{off}$) that is within a range between any of the individual recited values.

In another embodiment, antibodies or binding fragments thereof of the invention bind Influenza A polypeptides or fragments or variants thereof with an on rate ($k_{on}$) of greater than or equal to $10^3$ $M^{-1}$ $sec^{-1}$, $5 \times 10^3$ $M^{-1}$ $sec^{-1}$, $10^4$ $M^{-1}$ $sec^{-1}$, $5 \times 10^4$ $M^{-1}$ $sec^{-1}$, $10^5$ $M^{-1}$ $sec^{-1}$, $5 \times 10^5$ $M^{-1}$ $sec^{-1}$, $10^6$ $M^{-1}$ sec-1, $5 \times 10^6$ $M^{-1}$ $sec^{-1}$, $10^7$ $M^{-1}$ sec-1, or $5 \times 10^7$ $M^{-1}$ $sec^{-1}$. In a more particular embodiment, antibodies or binding fragments thereof of the invention bind Influenza A polypeptides or fragments or variants thereof with an on rate ($k_{on}$) greater than or equal to $10^5$ $M^{-1}$ $sec^{-1}$, $5 \times 10^5$ $M^{-1}$ $sec^{-1}$, $10^6$ $M^{-1}$ sec-1, $5 \times 10^6$ $M^{-1}$ $sec^{-1}$, $10^7$ $M^{-1}$ $sec^{-1}$ or $5 \times 10^7$ $M^{-1}$ $sec^{-1}$. The invention encompasses antibodies that bind Influenza A polypeptides with on rate ($k_{on}$) that is within a range between any of the individual recited values.

In one embodiment, a binding assay may be performed either as direct binding assays or as competition-binding assays. Binding can be detected using standard ELISA or standard Flow Cytometry assays. In a direct binding assay, a candidate antibody is tested for binding to its cognate antigen. Competition-binding assay, on the other hand, assess the ability of a candidate antibody to compete with a known antibody or other compound that binds to the Influenza A virus HA stalk. In general any method that permits the binding of an antibody with the Influenza A virus HA stalk that can be detected is encompassed with the scope of the present invention for detecting and measuring the binding characteristics of the antibodies. One of skill in the art will recognize these well-known methods and for this reason are not provided in detail here. These methods are also utilized to screen a panel of antibodies for those providing the desired characteristics.

An antibody of the invention immunospecifically binds to Influenza A virus HA stalk and is capable of neutralizing Influenza A virus infection. Neutralization assays can be performed as described herein in the Examples section or using other methods known in the art. The term "inhibitory concentration 50%" (abbreviated as "$IC_{50}$") represents the concentration of an inhibitor (e.g., an antibody of the invention) that is required for 50% neutralization of Influenza A virus. It will be understood by one of ordinary skill in the art that a lower $IC_{50}$ value corresponds to a more potent inhibitor.

In one embodiment, an antibody or binding fragment thereof according to the invention has a neutralizing potency expressed as 50% inhibitory concentration ($IC_{50}$ ug/ml) in the range of from about 0.01 ug/ml to about 50 ug/ml, or in the range of from about 0.01 ug/ml to about 5 ug/ml of antibody, or in the range of from about 0.01 ug/ml to about 0.1 ug/ml of antibody for neutralization of influenza A virus in a microneutralization assay. The highest concentration of antibody used in microneutralization assay described herein was 50 ug/ml. The high potency of antibodies of the invention means that lower concentrations of antibody can be used to attain 50% neutralization of influenza A virus.

In certain embodiments, the antibodies of the invention may induce cell death. An antibody which "induces cell death" is one which causes a viable cell to become nonviable. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e., in the absence of complement) and in the absence of immune effector cells. To determine whether the antibody is able to induce cell death, loss of membrane integrity as evaluated by uptake of propidium iodide (PI), trypan blue (see Moore et al. *Cytotechnology* 17:1-11 (1995)), 7AAD or other methods well known in the art can be assessed relative to untreated cells.

In a specific embodiment, the antibodies of the invention may induce cell death via apoptosis. An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody which induces apoptosis is one which results in about 2 to 50 fold, preferably about 5 to 50 fold, and most preferably about 10 to 50 fold, induction of annexin binding relative to untreated cell in an annexin binding assay.

In another specific embodiment, the antibodies of the invention may induce cell death via antibody-dependent cellular cytotoxicity (ADCC) and/or complement-dependent cell-mediated cytotoxicity (CDC) and/or antibody dependent cell-mediated phagocytosis (ADCP). Expression of ADCC activity and CDC activity of the human IgG1 subclass antibodies generally involves binding of the Fc region of the antibody to a receptor for an antibody (hereinafter referred to as "FcγR") existing on the surface of effector cells such as killer cells, natural killer cells or activated macrophages. Various complement components can be bound. Regarding the binding, it has been suggested that several amino acid residues in the hinge region and the second domain of C region (hereinafter referred to as "Cγ2 domain") of the antibody are important (*Eur. J. Immunol.*, 23, 1098 (1993), *Immunology*, 86, 319 (1995), *Chemical Immunology*, 65, 88 (1997)) and that a sugar chain in the Cγ2 domain (*Chemical Immunology*, 65, 88 (1997)) is also important.

To assess ADCC activity of an antibody of interest, an in vitro ADCC assay can be used, such as that described in U.S. Pat. No. 5,500,362. The assay may also be performed using a commercially available kit, e.g. CytoTox 96® (Promega). Useful effector cells for such assays include, but are not limited to peripheral blood mononuclear cells (PBMC), Natural Killer (NK) cells, and NK cell lines. NK cell lines expressing a transgenic Fc receptor (e.g. CD16) and associated signaling polypeptide (e.g. $FC_\varepsilon RI$-γ) may also serve as effector cells (WO 2006/023148). For example, the ability of any particular antibody to mediate lysis by complement activation and/or ADCC can be assayed. The cells of interest are grown and labeled in vitro; the antibody is added to the cell culture in combination with immune cells which may be activated by the antigen antibody complexes; i.e., effector cells involved in the ADCC response. The antibody can also be tested for complement activation. In either case, cytolysis is detected by the release of label from the lysed cells. The extent of cell lysis may also be determined by detecting the release of cytoplasmic proteins (e.g. LDH) into the supernatant. In fact, antibodies can be screened using the patient's own serum as a source of complement and/or immune cells. Antibodies that are capable of mediating human ADCC in the in vitro test can then be used therapeutically in that particular patient. ADCC activity of the molecule of interest may also be assessed in vivo, e.g., in an animal model such as that disclosed in Clynes et al., *Proc. Natl. Acad. Sci.* (USA) 95:652-656 (1998). Moreover, techniques for modulating (i.e., increasing or decreasing) the level of ADCC, and optionally CDC activity, of an antibody are well-known in the art (e.g., U.S. Pat. Nos. 5,624,821; 6,194,551; 7,317,091). Antibodies of the present invention may be capable or may have been modified to have the ability of inducing ADCC and/or CDC. Assays to determine ADCC function can be practiced using human effector cells to assess human ADCC function. Such assays may also include those intended to screen for antibodies that induce, mediate, enhance, block cell death by necrotic and/or apoptotic mechanisms. Such methods including assays utilizing viable dyes, methods of detecting and analyzing caspases, and assays measuring DNA breaks can be used to assess the apoptotic activity of cells cultured in vitro with an antibody of interest.

Production of Antibodies

The following describes exemplary techniques for the production of the antibodies useful in the present invention.

Monoclonal Antibodies

Monoclonal antibodies can be prepared using a wide variety of techniques known in the art including the use of hybridoma (Kohler et al., *Nature*, 256:495 (1975); Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681 (Elsevier, N.Y., 1981), recombinant, and phage display technologies, or a combination thereof. The term "monoclonal antibody" as used herein refers to an antibody obtained from a population of substantially homogeneous or isolated antibodies, e.g., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against the same determinant on the antigen. In addition to their specificity, monoclonal antibodies are advantageous in that they may be synthesized uncontaminated by other antibodies. The modifier "monoclonal" is not to be construed as requiring production of the antibody by any particular method. Following is a description of representative methods for producing monoclonal antibodies which is not intended to be limiting and may be used to produce, for example, monoclonal mammalian, chimeric, humanized, human, domain, diabodies, vaccibodies, linear and multispecific antibodies.

Hybridoma Techniques

Methods for producing and screening for specific antibodies using hybridoma technology are routine and well known in the art. In the hybridoma method, mice or other appropriate host animals, such as hamster, are immunized as described above to elicit lymphocytes that produce or are capable of producing antibodies that will specifically bind to the antigen used for immunization. Alternatively, lymphocytes may be immunized in vitro. After immunization, lymphocytes are isolated and then fused with a myeloma cell line using a suitable fusing agent or fusion partner, such as polyethylene glycol, to form a hybridoma cell (Goding, *Monoclonal Antibodies: Principles and Practice*, pp. 59-103 (Academic Press, 1986)). In certain embodiments, the selected myeloma cells are those that fuse efficiently, support stable high-level production of antibody by the selected antibody-producing cells, and are sensitive to a selective medium that selects against the unfused parental cells. In one aspect, the myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); and Brodeur et al., *Monoclonal Antibody Production Techniques and Applications*, pp. 51-63 (Marcel Dekker, Inc., New York, 1987)).

Once hybridoma cells that produce antibodies of the desired specificity, affinity, and/or activity are identified, the clones may be subcloned by limiting dilution procedures and grown by standard methods (Goding, Supra). Suitable culture media for this purpose include, for example, D-MEM or RPMI-1640 medium. In addition, the hybridoma cells may be grown in vivo as ascites tumors in an animal e.g., by i.p. injection of the cells into mice.

The monoclonal antibodies secreted by the sub-clones are suitably separated from the culture medium, ascites fluid, or serum by conventional antibody purification procedures such as, for example, affinity chromatography (e.g., using protein A or protein G-Sepharose) or ion-exchange chromatography, affinity tags, hydroxylapatite chromatography, gel electrophoresis, dialysis, etc. Exemplary purification methods are described in more detail below.

Recombinant DNA Techniques

Methods for producing and screening for specific antibodies using recombinant DNA technology are routine and well known in the art (e.g. U.S. Pat. No. 4,816,567). DNA encoding the monoclonal antibodies may be readily isolated and/or sequenced using conventional procedures (e.g., by using oligonucleotide probes that are capable of binding specifically to genes encoding the heavy and light chains of murine antibodies). Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Pluckthun, *Immunol. Revs.*, 130:151-188 (1992). As described below for antibodies generated by phage display and humanization of antibodies, DNA or genetic material for recombinant antibodies can be obtained from source(s) other than hybridomas to generate antibodies of the invention.

Recombinant expression of an antibody or variant thereof generally requires construction of an expression vector containing a polynucleotide that encodes the antibody. The invention, thus, provides replicable vectors comprising a nucleotide sequence encoding an antibody molecule, a heavy or light chain of an antibody, a heavy or light chain variable domain of an antibody or a portion thereof, or a heavy or light chain CDR, operably linked to a promoter. Such vectors may include the nucleotide sequence encoding the constant region of the antibody molecule (see, e.g., U.S. Pat. Nos. 5,981,216; 5,591,639; 5,658,759 and 5,122,464) and the variable domain of the antibody may be cloned into such a vector for expression of the entire heavy, the entire light chain, or both the entire heavy and light chains.

Once the expression vector is transferred to a host cell by conventional techniques, the transfected cells are then cultured by conventional techniques to produce an antibody. Thus, the invention includes host cells containing a polynucleotide encoding an antibody of the invention or fragments thereof, or a heavy or light chain thereof, or portion thereof, or a single-chain antibody of the invention, operably linked to a heterologous promoter. In certain embodiments for the expression of double-chained antibodies, vectors encoding both the heavy and light chains may be co-expressed in the host cell for expression of the entire immunoglobulin molecule, as detailed below.

Mammalian cell lines available as hosts for expression of recombinant antibodies are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Different host cells have characteristic and specific mechanisms for the post-translational processing and modification of proteins and gene products. Appropriate cell lines or host systems can be chosen to ensure the correct modification and processing of the antibody or portion thereof expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, Hs578T, HTB2, BT2O and T47D, NS0 (a murine myeloma cell line that does not endogenously produce any functional immunoglobulin chains), SP20, CRL7O3O and HsS78Bst cells. Human cell lines developed by immortalizing human lymphocytes can be used to recombinantly produce monoclonal antibodies. The human cell line PER.C6. (Crucell, Netherlands) can be used to recombinantly produce monoclonal antibodies.

Additional cell lines which may be used as hosts for expression of recombinant antibodies include, but are not limited to, insect cells (e.g. Sf21/Sf9, *Trichoplusia ni* Bti-Tn5b1-4) or yeast cells (e.g. *S. cerevisiae, Pichia*, U.S. Pat. No. 7,326,681; etc), plants cells (US20080066200); and chicken cells (WO2008142124).

In certain embodiments, antibodies of the invention are expressed in a cell line with stable expression of the antibody. Stable expression can be used for long-term, high-yield production of recombinant proteins. For example, cell lines which stably express the antibody molecule may be generated. Host cells can be transformed with an appropriately engineered vector comprising expression control elements (e.g., promoter, enhancer, transcription terminators, polyadenylation sites, etc.), and a selectable marker gene. Following the introduction of the foreign DNA, cells may be allowed to grow for 1-2 days in an enriched media, and then are switched to a selective media. The selectable marker in the recombinant plasmid confers resistance to the selection and allows cells that stably integrated the plasmid into their chromosomes to grow and form foci which in turn can be cloned and expanded into cell lines. Methods for producing stable cell lines with a high yield are well known in the art and reagents are generally available commercially.

In certain embodiments, antibodies of the invention are expressed in a cell line with transient expression of the antibody. Transient transfection is a process in which the nucleic acid introduced into a cell does not integrate into the genome or chromosomal DNA of that cell. It is in fact maintained as an extra-chromosomal element, e.g. as an episome, in the cell. Transcription processes of the nucleic acid of the episome are not affected and a protein encoded by the nucleic acid of the episome is produced.

The cell line, either stable or transiently transfected, is maintained in cell culture medium and conditions well known in the art resulting in the expression and production of monoclonal antibodies. In certain embodiments, the mammalian cell culture media is based on commercially available media formulations, including, for example, DMEM or Ham's F12. In other embodiments, the cell culture media is modified to support increases in both cell growth and biologic protein expression. As used herein, the terms "cell culture medium," "culture medium," and "medium formulation" refer to a nutritive solution for the maintenance, growth, propagation, or expansion of cells in an artificial in vitro environment outside of a multicellular organism or tissue. Cell culture medium may be optimized for a specific cell culture use, including, for example, cell culture growth medium which is formulated to promote cellular growth, or cell culture production medium which is formulated to promote recombinant protein production. The terms nutrient, ingredient, and component are used interchangeably herein to refer to the constituents that make up a cell culture medium.

In one embodiment, the cell lines are maintained using a fed batch method. As used herein, "fed batch method," refers to a method by which a fed batch cell culture is supplied with additional nutrients after first being incubated with a basal medium. For example, a fed batch method may comprise adding supplemental media according to a determined feeding schedule within a given time period. Thus, a "fed batch cell culture" refers to a cell culture wherein the cells, typically mammalian, and culture medium are supplied to the culturing vessel initially and additional culture nutrients are fed, continuously or in discrete increments, to the culture during culturing, with or without periodic cell and/or product harvest before termination of culture.

The cell culture medium used and the nutrients contained therein are known to one of skill in the art. In one embodiment, the cell culture medium comprises a basal medium and at least one hydrolysate, e.g., soy-based hydrolysate, a yeast-based hydrolysate, or a combination of the two types of hydrolysates resulting in a modified basal medium. In another embodiment, the additional nutrients may include only a basal medium, such as a concentrated basal medium, or may include only hydrolysates, or concentrated hydrolysates. Suitable basal media include, but are not limited to Dulbecco's Modified Eagle's Medium (DMEM), DME/F12, Minimal Essential Medium (MEM), Basal Medium Eagle (BME), RPMI 1640, F-10, F-12, α-Minimal Essential Medium (α-MEM), Glasgow's Minimal Essential Medium (G-MEM), PF CHO (see, e.g., CHO protein free medium (Sigma) or EX-CELL™ 325 PF CHO Serum-Free Medium for CHO Cells Protein-Free (SAFC Bioscience), and Iscove's Modified Dulbecco's Medium. Other examples of basal media which may be used in the invention include BME Basal Medium (Gibco-Invitrogen, see also Eagle, H (1965) Proc. Soc. Exp. Biol. Med. 89, 36); Dulbecco's Modified Eagle Medium (DMEM, powder) (Gibco-Invitrogen (#31600); see also Dulbecco and Freeman (1959) Virology 8, 396; Smith et al. (1960) Virology 12, 185. Tissue Culture Standards Committee, In Vitro 6:2, 93); CMRL 1066 Medium (Gibco-Invitrogen (#11530), see also Parker R. C. et al (1957) Special Publications, N.Y. Academy of Sciences, 5, 303).

The basal medium may be serum-free, meaning that the medium contains no serum (e.g., fetal bovine serum (FBS), horse serum, goat serum, or any other animal-derived serum known to one skilled in the art) or animal protein free media or chemically defined media.

The basal medium may be modified in order to remove certain non-nutritional components found in standard basal medium, such as various inorganic and organic buffers, surfactant(s), and sodium chloride. Removing such components from basal cell medium allows an increased concentration of the remaining nutritional components, and may improve overall cell growth and protein expression. In addition, omitted components may be added back into the cell culture medium containing the modified basal cell medium according to the requirements of the cell culture conditions. In certain embodiments, the cell culture medium contains a modified basal cell medium, and at least one of the following nutrients, an iron source, a recombinant growth factor; a buffer; a surfactant; an osmolarity regulator; an energy source; and non-animal hydrolysates. In addition, the modified basal cell medium may optionally contain amino acids, vitamins, or a combination of both amino acids and vitamins. In another embodiment, the modified basal medium further contains glutamine, e.g, L-glutamine, and/or methotrexate.

Antibody production can be conducted in large quantity by a bioreactor process using fed-batch, batch, perfusion or continuous feed bioreactor methods known in the art. Large-scale bioreactors have at least 1000 liters of capacity, preferably about 1,000 to 100,000 liters of capacity. These bioreactors may use agitator impellers to distribute oxygen and nutrients. Small scale bioreactors refers generally to cell culturing in no more than approximately 100 liters in volumetric capacity, and can range from about 1 liter to about 100 liters. Alternatively, single-use bioreactors (SUB) may be used for either large-scale or small-scale culturing.

Temperature, pH, agitation, aeration and inoculum density will vary depending upon the host cells used and the recombinant protein to be expressed. For example, a recombinant protein cell culture may be maintained at a temperature between 30 and 45° C. The pH of the culture medium may be monitored during the culture process such that the pH stays at an optimum level, which may be for certain host cells, within a pH range of 6.0 to 8.0. An impellor driven mixing may be used for such culture methods for agitation. The rotational speed of the impellor may be approximately 50 to 200 cm/sec tip speed, but other airlift or other mixing/aeration systems known in the art may be used, depending on the type of host cell being cultured. Sufficient aeration is provided to maintain a dissolved oxygen concentration of approximately 20% to 80% air saturation in the culture, again, depending upon the selected host cell being cultured. Alternatively, a bioreactor may sparge air or oxygen directly into the culture medium. Other methods of oxygen supply exist, including bubble-free aeration systems employing hollow fiber membrane aerators.

Phage Display Techniques

Monoclonal antibodies or antibody fragments can be isolated from antibody phage libraries generated using the techniques described in McCafferty et al., *Nature*, 348:552-554 (1990). Clackson et al., *Nature*, 352:624-628 (1991) and Marks et al., J. Mol. Biol., 222:581-597 (1991). In such methods antibodies can be isolated by screening of a recombinant combinatorial antibody library, preferably a scFv phage display library, prepared using human VL and VH cDNAs prepared from mRNA derived from human lymphocytes. Methodologies for preparing and screening such libraries are known in the art. In addition to commercially available kits for generating phage display libraries (e.g., the Pharmacia Recombinant Phage Antibody System, catalog no. 27-9400-01; and the Stratagene SurfZAP™ phage display kit, catalog no. 240612), examples of methods and reagents particularly amenable for use in generating and screening antibody display libraries can be found in, for example, U.S. Pat. Nos. 6,248,516; 6,545,142; 6,291,158; 6,291,159; 6,291,160; 6,291,161; 6,680,192; 5,969,108; 6,172,197; 6,806,079; 5,885,793; 6,521,404; 6,544,731; 6,555,313; 6,593,081; 6,582,915; 7,195,866. Thus, these techniques are viable alternatives to traditional monoclonal antibody hybridoma techniques for generation and isolation of monoclonal antibodies.

In phage display methods, functional antibody domains are displayed on the surface of phage particles which carry the polynucleotide sequences encoding them. In a particular embodiment, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein.

As described in the above references, after phage selection, the antibody coding regions from the phage can be isolated and used to generate whole antibodies, including human antibodies, humanized antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864-869 (1992); and Better et al., Science 240:1041-1043 (1988).

Examples of techniques which can be used to produce single-chain Fvs and antibodies include those described in U.S. Pat. Nos. 4,946,778 and 5,258,498. Thus, techniques described above and those well known in the art can be used to generate recombinant antibodies wherein the binding domain, e.g. ScFv, was isolated from a phage display library.

Antibody Purification and Isolation

Once an antibody molecule has been produced by recombinant or hybridoma expression, it may be purified by any method known in the art for purification of an immunoglobulin molecule, for example, by chromatography (e.g., ion exchange, affinity, particularly by affinity for the specific antigens Protein A or Protein G, and sizing column chromatography), centrifugation, differential solubility, or by any other standard technique for the purification of proteins. Further, the antibodies of the present invention or fragments thereof may be fused to heterologous polypeptide sequences (referred to herein as "tags") to facilitate purification.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., *Bio/Technology*, 10:163-167 (1992) describe a procedure for isolating antibodies which are secreted into the periplasmic space of *E. coli*. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, hydrophobic interaction chromatography, ion exchange chromatography, gel electrophoresis, dialysis, and/or affinity chromatography either alone or in combination with other purification steps. The suitability of protein A as an affinity ligand depends on the species and isotype of any immunoglobulin Fc domain that is present in the antibody and will be understood by one of skill in the art. The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $CH_3$ domain, the Bakerbond ABX resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin, SEPHAROSE chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, and performed at low salt concentrations (e.g., from about 0-0.25 M salt).

Thus, in certain embodiments is provided antibodies of the invention that are substantially purified/isolated. In one embodiment, these isolated/purified recombinantly expressed antibodies may be administered to a patient to mediate a prophylactic or therapeutic effect. A prophylactic is a medication or a treatment designed and used to prevent a disease, disorder or infection from occurring. A therapeutic is concerned specifically with the treatment of a particular disease, disorder or infection. A therapeutic dose is the amount needed to treat a particular disease, disorder or infection. In another embodiment these isolated/purified antibodies may be used to diagnose Influenza A virus infection.

Human Antibodies

Human antibodies can be generated using methods well known in the art. Human antibodies avoid some of the problems associated with antibodies that possess murine or rat variable and/or constant regions. The presence of such murine or rat derived proteins can lead to the rapid clearance of the antibodies or can lead to the generation of an immune response against the antibody by a patient.

Human antibodies can be derived by in vitro methods. Suitable examples include but are not limited to phage display (MedImmune (formerly CAT), Morphosys, Dyax, Biosite/Medarex, Xoma, Symphogen, Alexion (formerly Proliferon), Affimed) ribosome display (MedImmune (formerly CAT)), yeast display, and the like. The phage display technology (See e.g., U.S. Pat. No. 5,969,108) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., *Current Opinion in Structural Biology* 3:564-571 (1993). Several sources of V-gene segments can be used for phage display. Clackson et al., *Nature,* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

Immunoglobulin genes undergo various modifications during maturation of the immune response, including recombination between V, D and J gene segments, isotype switching, and hypermutation in the variable regions. Recombination and somatic hypermutation are the foundation for generation of antibody diversity and affinity maturation, but they can also generate sequence liabilities that may make commercial production of such immunoglobulins as therapeutic agents difficult or increase the immunogenicity risk of the antibody. In general, mutations in CDR regions are likely to contribute to improved affinity and function, while mutations in framework regions may increase the risk of immunogenicity. This risk can be reduced by reverting framework mutations to germline while ensuring that activity of the antibody is not adversely impacted. The diversification processes may also generate some structural liabilities or these structural liabilities may exist within germline sequences contributing to the heavy and light chain variable domains. Regardless of the source, it may be desirable to remove potential structural liabilities that may result in instability, aggregation, heterogeneity of product, or increased immunogenicity. Examples of undesirable liabilities include unpaired cysteines (which may lead to disulfide bond scrambling, or variable sulfhydryl adduct formation), N-linked glycosylation sites (resulting in heterogeneity of structure and activity), as well as deamidation (e.g. NG, NS), isomerization (DG), oxidation (exposed methionine), and hydrolysis (DP) sites.

Accordingly, in order to reduce the risk of immunogenicity and improve pharmaceutical properties, it may be desirable to revert a framework sequence to germline, revert a CDR to germline, and/or remove a structural liability.

Thus, in one embodiment, where a particular antibody differs from its respective germline sequence at the amino acid level, the antibody sequence can be mutated back to the germline sequence. Such corrective mutations can occur at one, two, three or more positions, or a combination of any of the mutated positions, using standard molecular biological techniques.

Antibody Fragments

In certain embodiments, the present antibodies are antibody fragments or antibodies comprising these fragments. The antibody fragment comprises a portion of the full length antibody, which generally is the antigen binding or variable region thereof. Examples of antibody fragments include Fab, Fab', F(ab')$_2$, Fd and Fv fragments. Diabodies; linear antibodies (U.S. Pat. No. 5,641,870) and single-chain antibody molecules.

Traditionally, these fragments were derived via proteolytic digestion of intact antibodies using techniques well known in the art. However, these fragments can now be produced directly by recombinant host cells. Fab, Fv and scFv antibody fragments can all be expressed in and secreted from *E. coli*, thus allowing the facile production of large amounts of these fragments. In one embodiment, the antibody fragments can be isolated from the antibody phage libraries discussed above. Alternatively, Fab'-SH fragments can also be directly recovered from *E. coli* and chemically coupled to form F(ab')$_2$ fragments (Carter et al., *Bio/Technology,* 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single-chain Fv fragment (scFv). In certain embodiments, the antibody is not a Fab fragment. Fv and scFv are the only species with intact combining sites that are devoid of constant regions; thus, they are suitable for reduced non-specific binding during in vivo use. scFv fusion proteins may be constructed to yield fusion of an effector protein at either the amino or the carboxy terminus of an scFv.

In certain embodiments, the present antibodies are domain antibodies, e.g., antibodies containing the small functional binding units of antibodies, corresponding to the variable regions of the heavy (VH) or light (VL) chains of human antibodies. Examples of domain antibodies include, but are not limited to, those of Domantis (see, for example, WO04/058821; WO04/081026; WO04/003019; WO03/002609; U.S. Pat. Nos. 6,291,158; 6,582,915; 6,696,245; and 6,593,081).

In certain embodiments of the invention, the present antibodies are linear antibodies. Linear antibodies comprise a pair of tandem Fd segments (VH-CH1-VH-CH1) which form a pair of antigen-binding regions. See, Zapata et al., *Protein Eng.,* 8(10):1057-1062 (1995).

Other Amino Acid Sequence Modifications

In addition to the above described human, humanized and/or chimeric antibodies, the present invention also encompasses further modifications and, their variants and fragments thereof, of the antibodies of the invention comprising one or more amino acid residues and/or polypeptide substitutions, additions and/or deletions in the variable light (VL) domain and/or variable heavy (VH) domain and/or Fc region and post translational modifications. Included in these modifications are antibody conjugates wherein an antibody has been covalently attached to a moiety. Moieties suitable for attachment to the antibodies include but are not limited to, proteins, peptides, drugs, labels, and cytotoxins. These changes to the antibodies may be made to alter or fine tune the characteristics (biochemical, binding and/or functional) of the antibodies as is appropriate for treatment and/or diagnosis of Influenza A infection. Methods for forming conjugates, making amino acid and/or polypeptide changes and post-translational modifications are well known in the art, some of which are detailed below.

Amino acid changes to the antibodies necessarily results in sequences that are less than 100% identical to the above identified antibody sequences or parent antibody sequence. In certain embodiments, in this context, the antibodies many have about 25% to about 95% sequence identity to the amino acid sequence of either the heavy or light chain variable domain of an antibody as described herein. Thus, in one embodiment a modified antibody may have an amino acid sequence having at least 25%, 35%, 45%, 55%, 65%, 75%, 80%, 85%, 90%, 95%, 96%, 97%, 98% or 99% amino acid sequence identity or similarity with the amino acid sequence of either the heavy or light chain variable domain of an antibody as described herein. In another embodiment, an altered antibody may have an amino acid sequence having at least 25%, 35%, 45%, 55%, 65%, 75%, 80%, 85%, 90%, 95%, 96%, 97%, 98% or 99% amino acid sequence identity or similarity with the amino acid sequence of the heavy or light chain CDR1, CDR2, or CDR3 of an antibody as described herein. In another embodiment, an altered antibody may have an amino acid sequence having at least 25%, 35%, 45%, 55%, 65%, 75%, 80%, 85%, 90%, 95%, 96%, 97%, 98% or 99% amino acid sequence identity or similarity with the amino acid sequence of the heavy or light chain FR1, FR2, FR3 or FR4 of an antibody as described herein.

In certain embodiments, altered antibodies are generated by one or more amino acid alterations (e.g., substitutions, deletion and/or additions) introduced in one or more of the variable regions of the antibody. In another embodiment, the amino acid alterations are introduced in the framework regions. One or more alterations of framework region residues may result in an improvement in the binding affinity of the antibody for the antigen. This may be especially true when these changes are made to humanized antibodies wherein the framework region may be from a different species than the CDR regions. Examples of framework region residues to modify include those which non-covalently bind antigen directly (Amit et al., Science, 233:747-753 (1986)); interact with/effect the conformation of a CDR (Chothia et al., J. Mol. Biol., 196:901-917 (1987)); and/or participate in the VL-VH interface (U.S. Pat. Nos. 5,225,539 and 6,548,640). In one embodiment, from about one to about five framework residues may be altered. Sometimes, this may be sufficient to yield an antibody mutant suitable for use in preclinical trials, even where none of the hypervariable region residues have been altered. Normally, however, an altered antibody will comprise additional hypervariable region alteration(s).

One useful procedure for generating altered antibodies is called "alanine scanning mutagenesis" (Cunningham and Wells, Science, 244:1081-1085 (1989)). In this method, one or more of the hypervariable region residue(s) are replaced by alanine or polyalanine residue(s) to alter the interaction of the amino acids with the target antigen. Those hypervariable region residue(s) demonstrating functional sensitivity to the substitutions then are refined by introducing additional or other mutations at or for the sites of substitution. Thus, while the site for introducing an amino acid sequence variation is predetermined, the nature of the mutation per se need not be predetermined. The Ala-mutants produced this way are screened for their biological activity as described herein.

In certain embodiments the substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display (Hawkins et al., J. Mol. Biol., 254:889-896 (1992) and Lowman et al., Biochemistry, 30(45):10832-10837 (1991)). Briefly, several hypervariable region sites (e.g., 6-7 sites) are mutated to generate all possible amino acid substitutions at each site. The antibody mutants thus generated are displayed in a monovalent fashion from filamentous phage particles as fusions to the gene III product of M13 packaged within each particle. The phage-displayed mutants are then screened for their biological activity (e.g., binding affinity) as herein disclosed.

Mutations in antibody sequences may include substitutions, deletions, including internal deletions, additions, including additions yielding fusion proteins, or conservative substitutions of amino acid residues within and/or adjacent to the amino acid sequence, but that result in a "silent" change, in that the change produces a functionally-equivalent antibody. Conservative amino acid substitutions may be made on the basis of similarity in polarity, charge, solubility, hydrophobicity, hydrophilicity, and/or the amphipathic nature of the residues involved. For example, non-polar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. In addition, glycine and proline are residues that can influence chain orientation. Non-conservative substitutions will entail exchanging a member of one of these classes for a member of another class. Furthermore, if desired, non-classical amino acids or chemical amino acid analogs can be introduced as a substitution or addition into the antibody sequence. Non-classical amino acids include, but are not limited to, the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general.

In another embodiment, any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

Variant Fc Regions

It is known that variants of the Fc region (e.g., amino acid substitutions and/or additions and/or deletions) enhance or diminish effector function of the antibody (See e.g., U.S. Pat. Nos. 5,624,821; 5,885,573; 6,538,124; 7,317,091; 5,648,260; 6,538,124; WO 03/074679; WO 04/029207; WO 04/099249; WO 99/58572; US Publication No. 2006/0134105; 2004/0132101; 2006/0008883) and may alter the pharmacokinetic properties (e.g. half-life) of the antibody (see, U.S. Pat. Nos. 6,277,375 and 7,083,784). Thus, in certain embodiments, the antibodies of the invention comprise an altered Fc region (also referred to herein as "variant Fc region") in which one or more alterations have been made in the Fc region in order to change functional and/or pharmacokinetic properties of the antibodies. Such alterations may result in a decrease or increase of C1q binding and complement dependent cytotoxicity (CDC) or of FcγR binding, for IgG, and antibody-dependent cellular cytotoxicity (ADCC), or antibody dependent cell-mediated phagocytosis (ADCP). The present invention encompasses the antibodies described herein with variant Fc regions wherein changes have been made to fine tune the effector function, enhancing or diminishing, providing a desired effector function. Accordingly, the antibodies of the invention comprise a variant Fc region (i.e., Fc regions that have been altered as discussed below). Antibodies of the invention comprising a variant Fc region are also referred to here as "Fc variant antibodies." As used herein native refers to the unmodified parental sequence and the antibody comprising a native Fc region is herein referred to as a "native Fc antibody". Fc variant antibodies can be generated by numerous methods well known to one skilled in the art. Non-limiting examples include, isolating antibody coding regions (e.g., from hybridoma) and making one or more desired substitutions in the Fc region of the isolated antibody coding region. Alternatively, the antigen-binding portion (e.g., variable regions) of an antibody may be sub-cloned into a vector encoding a variant Fc region. In one embodiment, the variant Fc region exhibits a similar level of inducing effector function as compared to the native Fc region. In another embodiment, the variant Fc region exhibits a higher induction of effector function as compared to the native Fc. Some specific embodiments of variant Fc regions are detailed infra. Methods for measuring effector function are well known in the art.

The effector function of an antibody is modified through changes in the Fc region, including but not limited to, amino acid substitutions, amino acid additions, amino acid deletions and changes in post-translational modifications to Fc amino acids (e.g. glycosylation). The methods described below may be used to fine tune the effector function of a present antibody, a ratio of the binding properties of the Fc region for the FcR (e.g., affinity and specificity), resulting in a therapeutic antibody with the desired properties.

It is understood that the Fc region as used herein includes the polypeptides comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, Fc comprises immunoglobulin domains Cgamma2 and Cgamma3 (Cγ2 and Cγ3) and the hinge between Cgamma1 (Cγ1) and Cgamma2 (Cγ2). Although the boundaries of the Fc region may vary, the human IgG heavy chain Fc region is usually defined to comprise residues C226 or P230 to its carboxyl-terminus, wherein the numbering is according to the EU index as set forth in Kabat. Fc may refer to this region in isolation, or this region in the context of an antibody, antibody fragment, or Fc fusion protein. Polymorphisms have been observed at a number of different Fc positions, including but not limited to positions 270, 272, 312, 315, 356, and 358 as numbered by the EU index, and thus slight differences between the presented sequence and sequences in the prior art may exist.

In one embodiment, Fc variant antibodies exhibit altered binding affinity for one or more Fc receptors including, but not limited to FcRn, FcγRI (CD64) including isoforms FcγRIA, FcγRIB, and FcγRIC, FcγRII (CD32 including isoforms FcγRIIA, FcγRIIB, and FcγRIIC), and FcγRIII (CD16, including isoforms FcγRIIIA and FcγRIIIB) as compared to an native Fc antibody.

In one embodiment, an Fc variant antibody has enhanced binding to one or more Fc ligand relative to a native Fc antibody. In another embodiment, the Fc variant antibody exhibits increased or decreased affinity for an Fc ligand that is at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold, or is between 2 fold and 10 fold, or between 5 fold and 50 fold, or between 25 fold and 100 fold, or between 75 fold and 200 fold, or between 100 and 200 fold, more or less than a native Fc antibody. In another embodiment, Fc variant antibodies exhibit affinities for an Fc ligand that are at least 90%, at least 80%, at least 70%, at least 60%, at least 50%, at least 40%, at least 30%, at least 20%, at least 10%, or at least 5% more or less than an native Fc antibody. In certain embodiments, an Fc variant antibody has increased affinity for an Fc ligand. In other embodiments, an Fc variant antibody has decreased affinity for an Fc ligand.

In a specific embodiment, an Fc variant antibody has enhanced binding to the Fc receptor FcγRIIIA. In another specific embodiment, an Fc variant antibody has enhanced binding to the Fc receptor FcγRIIB. In a further specific embodiment, an Fc variant antibody has enhanced binding to both the Fc receptors FcγRIIIA and FcγRIIB. In certain embodiments, Fc variant antibodies that have enhanced binding to FcγRIIIA do not have a concomitant increase in binding the FcγRIIB receptor as compared to a native Fc antibody. In a specific embodiment, an Fc variant antibody has reduced binding to the Fc receptor FcγRIIIA. In a further specific embodiment, an Fc variant antibody has reduced binding to the Fc receptor FcγRIIB. In still another specific embodiment, an Fc variant antibody exhibiting altered affinity for FcγRIIIA and/or FcγRIIB has enhanced binding to the Fc receptor FcRn. In yet another specific embodiment, an Fc variant antibody exhibiting altered affinity for FcγRIIIA and/or FcγRIIB has altered binding to C1q relative to a native Fc antibody.

In one embodiment, Fc variant antibodies exhibit affinities for FcγRIIIA receptor that are at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold, or are between 2 fold and 10 fold, or between 5 fold and 50 fold, or between 25 fold and 100 fold, or between 75 fold and 200 fold, or between 100 and 200 fold, more or less than an native Fc antibody. In another embodiment, Fc variant antibodies exhibit affinities for FcγRIIIA that are at least 90%, at least 80%, at least 70%, at least 60%, at least 50%, at least 40%, at least 30%, at least 20%, at least 10%, or at least 5% more or less than an native Fc antibody.

In one embodiment, Fc variant antibodies exhibit affinities for FcγRIIB receptor that are at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold, or are between 2 fold and 10 fold, or between 5 fold and 50 fold, or between 25 fold and 100 fold, or between 75 fold and 200 fold, or between 100 and 200 fold, more or less than an native Fc antibody. In another embodiment, Fc variant antibodies exhibit affinities for FcγRIIB that are at least 90%, at least 80%, at least 70%, at least 60%, at least 50%, at least 40%, at least 30%, at least 20%, at least 10%, or at least 5% more or less than an native Fc antibody.

In one embodiment, Fc variant antibodies exhibit increased or decreased affinities to C1 q relative to a native Fc antibody. In another embodiment, Fc variant antibodies exhibit affinities for C1 q receptor that are at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold, or are between 2 fold and 10 fold, or between 5 fold and 50 fold, or between 25 fold and 100 fold, or between 75 fold and 200 fold, or between 100 and 200 fold, more or less than an native Fc antibody. In another embodiment, Fc variant antibodies exhibit affinities for C1q that are at least 90%, at least 80%, at least 70%, at least 60%, at least 50%, at least 40%, at least 30%, at least 20%, at least 10%, or at least 5% more or less than an native Fc antibody. In still another specific embodiment, an Fc variant antibody exhibiting altered affinity for Ciq has enhanced binding to the Fc receptor FcRn. In yet another specific embodiment, an Fc variant antibody exhibiting altered affinity for C1q has altered binding to FcγRIIIA and/or FcγRIIB relative to a native Fc antibody.

It is well known in the art that antibodies are capable of directing the attack and destruction through multiple processes collectively known in the art as antibody effector functions. One of these processes, known as "antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enables these cytotoxic effector cells to bind specifically to an antigen-bearing cells and subsequently kill the cells with cytotoxins. Specific high-affinity IgG antibodies directed to the surface of cells "arm" the cytotoxic cells and are required for such killing. Lysis of the cell is extracellular, requires direct cell-to-cell contact, and does not involve complement.

Another process encompassed by the term effector function is complement dependent cytotoxicity (hereinafter referred to as "CDC") which refers to a biochemical event of cell destruction by the complement system. The complement system is a complex system of proteins found in normal blood plasma that combines with antibodies to destroy pathogenic bacteria and other foreign cells.

Still another process encompassed by the term effector function is antibody dependent cell-mediated phagocytosis (ADCP) which refers to a cell-mediated reaction wherein nonspecific cytotoxic cells that express one or more effector ligands recognize bound antibody on a cell and subsequently cause phagocytosis of the cell.

It is contemplated that Fc variant antibodies are characterized by in vitro functional assays for determining one or more FcγR mediated effector cell functions. In certain embodiments, Fc variant antibodies have similar binding properties and effector cell functions in in vivo models (such as those described and disclosed herein) as those in in vitro based assays. However, the present invention does not exclude Fc variant antibodies that do not exhibit the desired phenotype in in vitro based assays but do exhibit the desired phenotype in vivo.

In certain embodiments, an antibody comprising an Fc variant has enhanced cytotoxicity or phagocytosis activity (e.g., ADCC, CDC and ADCP) relative to an antibody comprising a native Fc region. In a specific embodiment, an Fc variant antibody has cytotoxicity or phagocytosis activity that is at least 2 fold, or at least 3 fold, or at least 5 fold or at least 10 fold or at least 50 fold or at least 100 fold, or at least 200 fold, or is between 2 fold and 10 fold, or between 5 fold and 50 fold, or between 25 fold and 100 fold, or between 75 fold and 200 fold, or between 100 and 200 fold, greater than that of a native Fc antibody. Alternatively, an Fc variant antibody has reduced cytotoxicity or phagocytosis activity relative to a native Fc antibody. In a specific embodiment, an Fc variant antibody has cytotoxicity or phagocytosis activity that is at least 2 fold, or at least 3 fold, or at least 5 fold or at least 10 fold or at least 50 fold or at least 100 fold, or at least 200 fold, or is between 2 fold and 10 fold, or between 5 fold and 50 fold, or between 25 fold and 100 fold, or between 75 fold and 200 fold, or between 100 and 200 fold, lower than that of a native Fc antibody.

In certain embodiments, Fc variant antibodies exhibit decreased ADCC activities as compared to a native Fc antibody. In another embodiment, Fc variant antibodies exhibit ADCC activities that are at least 2 fold, or at least 3 fold, or at least 5 fold or at least 10 fold or at least 50 fold or at least 100 fold, or at least 200 fold, or is between 2 fold and 10 fold, or between 5 fold and 50 fold, or between 25 fold and 100 fold, or between 75 fold and 200 fold, or between 100 and 200 fold, less than that of a native Fc antibody. In still another embodiment, Fc variant antibodies exhibit ADCC activities that are reduced by at least 10%, or at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500%, relative to a native Fc antibody. In certain embodiments, Fc variant antibodies have no detectable ADCC activity. In specific embodiments, the reduction and/or ablatement of ADCC activity may be attributed to the reduced affinity Fc variant antibodies exhibit for Fc ligands and/or receptors.

In an alternative embodiment, Fc variant antibodies exhibit increased ADCC activities as compared to a native Fc antibody. In another embodiment, Fc variant antibodies exhibit ADCC activities that are at least 2 fold, or at least 3 fold, or at least 5 fold or at least 10 fold or at least 50 fold or at least 100 fold greater than that of a native Fc antibody. In still another embodiment, Fc variant antibodies exhibit ADCC activities that are increased by at least 10%, or at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500% relative to a native Fc antibody. In specific embodiments, the increased ADCC activity may be attributed to the increased affinity Fc variant antibodies exhibit for Fc ligands and/or receptors.

In a specific embodiment, an Fc variant antibody has enhanced binding to the Fc receptor FcγRIIIA and has enhanced ADCC activity relative to a native Fc antibody. In other embodiments, the Fc variant antibody has both enhanced ADCC activity and enhanced serum half-life relative to a native Fc antibody.

In another specific embodiment, an Fc variant antibody has reduced binding to the Fc receptor FcγRIIIA and has reduced ADCC activity relative to a native Fc antibody. In other embodiments, the Fc variant antibody has both reduced ADCC activity and enhanced serum half-life relative to a native Fc antibody.

In certain embodiments, the cytotoxicity is mediated by CDC wherein the Fc variant antibody has either enhanced or decreased CDC activity relative to a native Fc antibody. The complement activation pathway is initiated by the binding of the first component of the complement system (C1q) to a molecule, an antibody for example, complexed with a cognate antigen. To assess complement activation, a CDC assay, e.g. as described in Gazzano-Santoro et al., 1996, *J. Immunol. Methods,* 202:163, may be performed.

In one embodiment, antibodies of the invention exhibit increased CDC activity as compared to a native Fc antibody. In another embodiment, Fc variant antibodies exhibit CDC activity that is at least 2 fold, or at least 3 fold, or at least 5 fold or at least 10 fold or at least 50 fold or at least 100 fold, or at least 200 fold, or is between 2 fold and 10 fold, or between 5 fold and 50 fold, or between 25 fold and 100 fold, or between 75 fold and 200 fold, or between 100 and 200 fold more than that of an native Fc antibody. In still another embodiment, Fc variant antibodies exhibit CDC activity that is increased by at least 10%, or at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500% relative to a native Fc antibody. In specific embodiments, the increase of CDC activity may be attributed to the increased affinity Fc variant antibodies exhibit for C1q.

Antibodies of the invention may exhibit increased CDC activity as compared to a native Fc antibody by virtue of COMPLEGENT® Technology (Kyowa Hakko Kirin Co., Ltd.), which enhances one of the major mechanisms of action of an antibody, CDC. With an approach called isotype chimerism, in which portions of IgG3, an antibody's isotype, are introduced into corresponding regions of IgG1, the standard isotype for therapeutic antibodies, COMPLEGENT® Technology significantly enhances CDC activity beyond that of either IgG1 or IgG3, while retaining the desirable features of IgG1, such as ADCC, PK profile and Protein A binding. In addition, it can be used together with POTELLIGENT® Technology, creating an even superior therapeutic Mab (ACCRETAMAB®) with enhanced ADCC and CDC activities Fc variant antibody of the invention may have enhanced ADCC activity and enhanced serum half-life relative to a native Fc antibody.

Fc variant antibody of the invention may CDC activity and enhanced serum half life relative to a native Fc antibody.

Fc variant antibody of the invention may have enhanced ADCC activity, enhanced CDC activity and enhanced serum half-life relative to a native Fc antibody.

The serum half-life of proteins comprising Fc regions may be increased by increasing the binding affinity of the Fc region for FcRn. The term "antibody half-life" as used herein means a pharmacokinetic property of an antibody that is a measure of the mean survival time of antibody molecules following their administration. Antibody half-life can be expressed as the time required to eliminate 50 percent of a known quantity of immunoglobulin from the patient's body (or other mammal) or a specific compartment thereof, for example, as measured in serum, i.e., circulating half-life, or in other tissues. Half-life may vary from one immunoglobulin or class of immunoglobulin to another. In general, an increase in antibody half-life results in an increase in mean residence time (MRT) in circulation for the antibody administered.

The increase in half-life allows for the reduction in amount of drug given to a patient as well as reducing the frequency of administration. To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

Alternatively, antibodies of the invention with increased half-lives may be generated by modifying amino acid residues identified as involved in the interaction between the Fc and the FcRn receptor (see, for examples, U.S. Pat. Nos. 6,821,505 and 7,083,784; and WO 09/058492). In addition, the half-life of antibodies of the invention may be increased by conjugation to PEG or Albumin by techniques widely utilized in the art. In some embodiments antibodies comprising Fc variant regions of the invention have an increased half-life of about 5%, about 10%, about 15%, about 20%, about 25%, about 30%, about 35%, about 40%, about 45%, about 50%, about 60%, about 65%, about 70%, about 80%, about 85%, about 90%, about 95%, about 100%, about 125%, about 150% or more as compared to an antibody comprising a native Fc region. In some embodiments antibodies comprising Fc variant regions have an increased half-life of about 2 fold, about 3 fold, about 4 fold, about 5 fold, about 10 fold, about 20 fold, about 50 fold or more, or is between 2 fold and 10 fold, or between 5 fold and 25 fold, or between 15 fold and 50 fold, as compared to an antibody comprising a native Fc region.

In one embodiment, the present invention provides Fc variants, wherein the Fc region comprises a modification (e.g., amino acid substitutions, amino acid insertions, amino acid deletions) at one or more positions selected from the group consisting of 221, 225, 228, 234, 235, 236, 237, 238, 239, 240, 241, 243, 244, 245, 247, 250, 251, 252, 254, 255, 256, 257, 262, 263, 264, 265, 266, 267, 268, 269, 279, 280, 284, 292, 296, 297, 298, 299, 305, 308, 313, 316, 318, 320, 322, 325, 326, 327, 328, 329, 330, 331, 332, 333, 334, 339, 341, 343, 370, 373, 378, 392, 416, 419, 421, 428, 433, 434, 435, 436, 440, and 443 as numbered by the EU index as set forth in Kabat. Optionally, the Fc region may comprise a modification at additional and/or alternative positions known to one skilled in the art (see, e.g., U.S. Pat. Nos. 5,624,821; 6,277,375; 6,737,056; 7,083,784; 7,317,091; 7,217,797; 7,276,585; 7,355,008; 2002/0147311; 2004/0002587; 2005/0215768; 2007/0135620; 2007/0224188; 2008/0089892; WO 94/29351; and WO 99/58572). Additional, useful amino acid positions and specific substitutions are exemplified in Tables 2, and 6-10 of U.S. Pat. No. 6,737,056; the tables presented in FIG. 41 of US 2006/024298; the tables presented in FIGS. 5, 12, and 15 of US 2006/235208; the tables presented in FIGS. 8, 9 and 10 of US 2006/0173170 and the tables presented in FIGS. 8-10, 13 and 14 of WO 09/058492.

In a specific embodiment, the present invention provides an Fc variant, wherein the Fc region comprises at least one substitution selected from the group consisting of 221K, 221Y, 225E, 225K, 225W, 228P, 234D, 234E, 234N, 234Q, 234T, 234H, 234Y, 234I, 234V, 234F, 235A, 235D, 235R, 235W, 235P, 235S, 235N, 235Q, 235T, 235H, 235Y, 235I, 235V, 235E, 235F, 236E, 237L, 237M, 237P, 239D, 239E, 239N, 239Q, 239F, 239T, 239H, 239Y, 240I, 240A, 240T, 240M, 241W, 241L, 241Y, 241E, 241R. 243W, 243L 243Y, 243R, 243Q, 244H, 245A, 247L, 247V, 247G, 250E, 250Q, 251F, 252L, 252Y, 254S, 254T, 255L, 256E, 256F, 256M, 257C, 257M, 257N, 262I, 262A, 262T, 262E, 263I, 263A, 263T, 263M, 264L, 264I, 264W, 264T, 264R, 264F, 264M, 264Y, 264E, 265A, 265G, 265N, 265Q, 265Y, 265F, 265V, 265I, 265L, 265H, 265T, 266I, 266A, 266T, 266M, 267Q, 267L, 268E, 269H, 269Y, 269F, 269R, 270E, 280A, 284M, 292P, 292L, 296E, 296Q, 296D, 296N, 296S, 296T, 296L, 296I, 296H, 296G, 297S, 297D, 297E, 298A, 298H, 298I, 298T, 298F, 299I, 299L, 299A, 299S, 299V, 299H, 299F, 299E, 305I, 308F, 313F, 316D, 318A, 318S, 320A, 320S, 322A, 322S, 325Q, 325L, 325I, 325D, 325E, 325A, 325T, 325V, 325H, 326A, 326D, 326E, 326G, 326M, 326V, 327G, 327W, 327N, 327L, 328S, 328M, 328D, 328E, 328N, 328Q, 328F, 328I, 328V, 328T, 328H, 328A, 329F, 329H, 329Q, 330K, 330G, 330T, 330C, 330L, 330Y, 330V, 330I, 330F, 330R, 330H, 331G, 331A, 331L, 331M, 331F, 331W, 331K, 331Q, 331E, 331S, 331V, 331I, 331C, 331Y, 331H, 331R, 331N, 331D, 331T, 332D, 332S, 332W, 332F, 332E, 332N, 332Q, 332T, 332H, 332Y, 332A, 333A, 333D, 333G, 333Q, 333S, 333V, 334A, 334E, 334H, 334L, 334M, 334Q, 334V, 334Y, 339T, 370E, 370N, 378D, 392T, 396L, 416G, 419H, 421K, 428L, 428F, 433K, 433L, 434A, 424F, 434W, 434Y, 436H, 440Y and 443W as numbered by the EU index as set forth in Kabat. Optionally, the Fc region may comprise additional and/or alternative amino acid substitutions known to one skilled in the art including but not limited to those exemplified in Tables 2, and 6-10 of U.S. Pat. No. 6,737,056; the tables presented in FIG. 41 of US 2006/024298; the tables presented in FIGS. 5, 12, and 15 of US 2006/235208; the tables presented in FIGS. 8, 9 and 10 of US 2006/0173170 and the tables presented in FIGS. 8, 9 and 10 of WO 09/058492.

In a specific embodiment, the present invention provides an Fc variant antibody, wherein the Fc region comprises at least one modification (e.g., amino acid substitutions, amino acid insertions, amino acid deletions) at one or more positions selected from the group consisting of 228, 234, 235 and 331 as numbered by the EU index as set forth in Kabat. In one embodiment, the modification is at least one substitution selected from the group consisting of 228P, 234F, 235E, 235F, 235Y, and 331S as numbered by the EU index as set forth in Kabat.

In another specific embodiment, the present invention provides an Fc variant antibody, wherein the Fc region is an IgG4 Fc region and comprises at least one modification at one or more positions selected from the group consisting of 228 and 235 as numbered by the EU index as set forth in Kabat. In still another specific embodiment, the Fc region is an IgG4 Fc region and the non-naturally occurring amino acids are selected from the group consisting of 228P, 235E and 235Y as numbered by the EU index as set forth in Kabat.

In another specific embodiment, the present invention provides an Fc variant, wherein the Fc region comprises at least one non-naturally occurring amino acid at one or more positions selected from the group consisting of 239, 330 and 332 as numbered by the EU index as set forth in Kabat. In one embodiment, the modification is at least one substitution selected from the group consisting of 239D, 330L, 330Y, and 332E as numbered by the EU index as set forth in Kabat.

In a specific embodiment, the present invention provides an Fc variant antibody, wherein the Fc region comprises at least one non-naturally occurring amino acid at one or more positions selected from the group consisting of 252, 254, and 256 as numbered by the EU index as set forth in Kabat. In one embodiment, the modification is at least one substitution selected from the group consisting of 252Y, 254T and 256E as numbered by the EU index as set forth in Kabat. In particularly preferred antibodies of the invention, the modification is three substitutions 252Y, 254T and 256E as numbered by the EU index as set forth in Kabat (known as "YTE"), see U.S. Pat. No. 7,083,784.

In certain embodiments the effector functions elicited by IgG antibodies strongly depend on the carbohydrate moiety linked to the Fc region of the protein (Claudia Ferrara et al., 2006, Biotechnology and Bioengineering 93:851-861). Thus, glycosylation of the Fc region can be modified to increase or decrease effector function (see for examples, Umana et al., 1999, Nat. Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473; U.S. Pat. Nos. 6,602,684; 6,946,292; 7,064,191; 7,214,775; 7,393,683; 7,425,446; 7,504,256; U.S. Publication. Nos. 2003/0157108; 2003/0003097; 2009/0010921; Potillegent™ technology (Biowa, Inc. Princeton, N.J.); GlycoMAb™ glycosylation engineering technology (GLYCART biotechnology AG, Zurich, Switzerland)). Accordingly, in one embodiment the Fc regions of antibodies of the invention comprise altered glycosylation of amino acid residues. In another embodiment, the altered glycosylation of the amino acid residues results in lowered effector function. In another embodiment, the altered glycosylation of the amino acid residues results in increased effector function. In a specific embodiment, the Fc region has reduced fucosylation. In another embodiment, the Fc region is afucosylated (see for examples, U.S. Patent Application Publication No. 2005/0226867). In one aspect, these antibodies with increased effector function, specifically ADCC, as generated in host cells (e.g., CHO cells, *Lemna minor*) engineered to produce highly defucosylated antibody with over 100-fold higher ADCC compared to antibody produced by the parental cells (Mori et al., 2004, Biotechnol Bioeng 88:901-908; Cox et al., 2006, Nat Biotechnol., 24:1591-7).

Addition of sialic acid to the oligosaccharides on IgG molecules can enhance their anti-inflammatory activity and alters their cytotoxicity (Keneko et al., Science, 2006, 313: 670-673; Scallon et al., Mol. Immuno. 2007 March; 44(7): 1524-34). The studies referenced above demonstrate that IgG molecules with increased sialylation have anti-inflammatory properties whereas IgG molecules with reduced sialylation have increased immunostimulatory properties (e.g., increase ADCC activity). Therefore, an antibody can be modified with an appropriate sialylation profile for a particular therapeutic application (US Publication No. 2009/0004179 and International Publication No. WO 2007/005786).

In one embodiment, the Fc regions of antibodies of the invention comprise an altered sialylation profile compared to the native Fc region. In one embodiment, the Fc regions of antibodies of the invention comprise an increased sialylation profile compared to the native Fc region. In another embodiment, the Fc regions of antibodies of the invention comprise a decreased sialylation profile compared to the native Fc region.

In one embodiment, the Fc variants of the present invention may be combined with other known Fc variants such as those disclosed in Ghetie et al., 1997, Nat Biotech. 15:637-40; Duncan et al., 1988, Nature 332:563-564; Lund et al., 1991, J. Immunol 147:2657-2662; Lund et al., 1992, Mol Immunol 29:53-59; Alegre et al, 1994, Transplantation 57:1537-1543; Hutchins et al., 1995, *Proc Natl. Acad Sci USA* 92:11980-11984; Jefferis et al., 1995, Immunol Lett. 44:111-117; Lund et al., 1995, Faseb J 9:115-119; Jefferis et al., 1996, Immunol Lett 54:101-104; Lund et al., 1996, J Immunol 157:4963-4969; Armour et al., 1999, Eur J Immunol 29:2613-2624; Idusogie et al., 2000, J Immunol 164: 4178-4184; Reddy et al., 2000, J Immunol 164:1925-1933; Xu et al., 2000, Cell Immunol 200:16-26; Idusogie et al., 2001, J Immunol 166:2571-2575; Shields et al., 2001, J Biol Chem 276:6591-6604; Jefferis et al, 2002, Immunol Lett 82:57-65; Presta et al., 2002, Biochem Soc Trans 30:487-490); U.S. Pat. Nos. 5,624,821; 5,885,573; 5,677,425; 6,165,745; 6,277,375; 5,869,046; 6,121,022; 5,624,821; 5,648,260; 6,528,624; 6,194,551; 6,737,056; 7,122,637; 7,183,387; 7,332,581; 7,335,742; 7,371,826; 6,821,505; 6,180,377; 7,317,091; 7,355,008; 2004/0002587; and WO 99/58572. Other modifications and/or substitutions and/or additions and/or deletions of the Fc domain will be readily apparent to one skilled in the art.

Glycosylation

In addition to the ability of glycosylation to alter the effector function of antibodies, modified glycosylation in the variable region can alter the affinity of the antibody for antigen. In one embodiment, the glycosylation pattern in the variable region of the present antibodies is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861. One or more amino acid substitutions can also be made that result in elimination of a glycosylation site present in the Fc region (e.g., Asparagine 297 of IgG). Furthermore, aglycosylated antibodies may be produced in bacterial cells which lack the necessary glycosylation machinery.

Antibody Conjugates

In certain embodiments, the antibodies of the invention are conjugated or covalently attached to a substance using methods well known in the art. In one embodiment, the attached substance is a therapeutic agent, a detectable label (also referred to herein as a reporter molecule) or a solid support. Suitable substances for attachment to antibodies include, but are not limited to, an amino acid, a peptide, a protein, a polysaccharide, a nucleoside, a nucleotide, an oligonucleotide, a nucleic acid, a hapten, a drug, a hormone, a lipid, a lipid assembly, a synthetic polymer, a polymeric microparticle, a biological cell, a virus, a fluorophore, a chromophore, a dye, a toxin, a hapten, an enzyme, an antibody, an antibody fragment, a radioisotope, solid matrixes, semi-solid matrixes and combinations thereof. Methods for conjugation or covalently attaching another substance to an antibody are well known in the art.

In certain embodiments, the antibodies of the invention are conjugated to a solid support. Antibodies may be conjugated to a solid support as part of the screening and/or purification and/or manufacturing process. Alternatively antibodies of the invention may be conjugated to a solid support as part of a diagnostic method or composition. A solid support suitable for use in the present invention is typically substantially insoluble in liquid phases. A large number of supports are available and are known to one of ordinary skill in the art. Thus, solid supports include solid and semi-solid matrixes, such as aerogels and hydrogels, resins, beads, biochips (including thin film coated biochips), microfluidic chip, a silicon chip, multi-well plates (also referred to as microtitre plates or microplates), membranes, conducting and non-conducting metals, glass (including microscope slides) and magnetic supports. More specific examples of solid supports include silica gels, polymeric membranes, particles, derivatized plastic films, glass beads, cotton, plastic beads, alumina gels, polysaccharides such as Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose, polyvinylchloride, polypropylene, polyethylene (including poly(ethylene glycol)), nylon, latex bead, magnetic bead, paramagnetic bead, superparamagnetic bead, starch and the like.

In some embodiments, the solid support may include a reactive functional group, including, but not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, etc., for attaching the antibodies of the invention.

A suitable solid phase support can be selected on the basis of desired end use and suitability for various synthetic protocols. For example, where amide bond formation is desirable to attach the antibodies of the invention to the solid support, resins generally useful in peptide synthesis may be employed, such as polystyrene (e.g., PAM-resin obtained from Bachem Inc., Peninsula Laboratories, etc.), POLYHIPE™ resin (obtained from Aminotech, Canada), polyamide resin (obtained from Peninsula Laboratories), polystyrene resin grafted with polyethylene glycol (Tenta-Gel™, Rapp Polymere, Tubingen, Germany), polydimethylacrylamide resin (available from Milligen/Biosearch, California), or PEGA beads (obtained from Polymer Laboratories).

In certain embodiments, the antibodies of the invention are conjugated to labels for purposes of diagnostics and other assays wherein the antibody and/or its associated ligand may be detected. A label conjugated to an antibody and used in the present methods and compositions described herein, is any chemical moiety, organic or inorganic, that exhibits an absorption maximum at wavelengths greater than 280 nm, and retains its spectral properties when covalently attached to an antibody. Labels include, without limitation, a chromophore, a fluorophore, a fluorescent protein, a phosphorescent dye, a tandem dye, a particle, a hapten, an enzyme and a radioisotope.

In certain embodiments, the antibodies are conjugated to a fluorophore. As such, fluorophores used to label antibodies of the invention include, without limitation; a pyrene (including any of the corresponding derivative compounds disclosed in U.S. Pat. No. 5,132,432), an anthracene, a naphthalene, an acridine, a stilbene, an indole or benzindole, an oxazole or benzoxazole, a thiazole or benzothiazole, a 4-amino-7-nitrobenz-2-oxa-1, 3-diazole (NBD), a cyanine (including any corresponding compounds in U.S. Pat. Nos. 6,977,305 and 6,974,873), a carbocyanine (including any corresponding compounds in U.S. Ser. No. 09/557,275; U.S. Pat. Nos. 4,981,977; 5,268,486; 5,569,587; 5,569,766; 5,486,616; 5,627,027; 5,808,044; 5,877,310; 6,002,003; 6,004,536; 6,008,373; 6,043,025; 6,127,134; 6,130,094; 6,133,445; and publications WO 02/26891, WO 97/40104, WO 99/51702, WO 01/21624; EP 1 065 250 A1), a carbostyryl, a porphyrin, a salicylate, an anthranilate, an azulene, a perylene, a pyridine, a quinoline, a borapolyazaindacene (including any corresponding compounds disclosed in U.S. Pat. Nos. 4,774,339; 5,187,288; 5,248,782; 5,274,113; and 5,433,896), a xanthene (including any corresponding compounds disclosed in U.S. Pat. Nos. 6,162,931; 6,130,101; 6,229,055; 6,339,392; 5,451,343; 5,227,487; 5,442,045; 5,798,276; 5,846,737; 4,945,171; U.S. Ser. Nos. 09/129,015 and 09/922,333), an oxazine (including any corresponding compounds disclosed in U.S. Pat. No. 4,714,763) or a benzoxazine, a carbazine (including any corresponding compounds disclosed in U.S. Pat. No. 4,810,636), a phenalenone, a coumarin (including an corresponding compounds disclosed in U.S. Pat. Nos. 5,696,157; 5,459,276; 5,501,980 and 5,830,912), a benzofuran (including an corresponding compounds disclosed in U.S. Pat. Nos. 4,603,209 and 4,849,362) and benzphenalenone (including any corresponding compounds disclosed in U.S. Pat. No. 4,812,409) and derivatives thereof. As used herein, oxazines include resorufins (including any corresponding compounds disclosed in 5,242,805), aminooxazinones, diaminooxazines, and their benzo-substituted analogs.

In a specific embodiment, the fluorophores conjugated to the antibodies described herein include xanthene (rhodol, rhodamine, fluorescein and derivatives thereof) coumarin, cyanine, pyrene, oxazine and borapolyazaindacene. In other embodiments, such fluorophores are sulfonated xanthenes, fluorinated xanthenes, sulfonated coumarins, fluorinated coumarins and sulfonated cyanines. Also included are dyes sold under the tradenames, and generally known as, ALEXA FLUOR®, DyLight, CY® Dyes, BODIPY®, OREGON GREEN®, PACIFIC BLUE™, IRDYE®, FAM, FITC, and ROX™.

The choice of the fluorophore attached to the antibody will determine the absorption and fluorescence emission properties of the conjugated antibody. Physical properties of a fluorophore label that can be used for antibody and antibody bound ligands include, but are not limited to, spectral characteristics (absorption, emission and stokes shift), fluorescence intensity, lifetime, polarization and photo-bleaching rate, or combination thereof. All of these physical properties can be used to distinguish one fluorophore from another, and thereby allow for multiplexed analysis. In certain embodiments, the fluorophore has an absorption maximum at wavelengths greater than 480 nm. In other embodiments, the fluorophore absorbs at or near 488 nm to 514 nm (particularly suitable for excitation by the output of the argon-ion laser excitation source) or near 546 nm (particularly suitable for excitation by a mercury arc lamp). In other embodiment a fluorophore can emit in the NIR (near infra red region) for tissue or whole organism applications. Other desirable properties of the fluorescent label may include cell permeability and low toxicity, for example if labeling of the antibody is to be performed in a cell or an organism (e.g., a living animal).

In certain embodiments, an enzyme is a label and is conjugated to an antibody described herein. Enzymes are desirable labels because amplification of the detectable signal can be obtained resulting in increased assay sensitivity. The enzyme itself does not produce a detectable response but functions to break down a substrate when it is contacted by an appropriate substrate such that the converted substrate produces a fluorescent, colorimetric or luminescent signal. Enzymes amplify the detectable signal because one enzyme on a labeling reagent can result in multiple substrates being converted to a detectable signal. The enzyme substrate is selected to yield the preferred measurable product, e.g. colorimetric, fluorescent or chemiluminescence. Such substrates are extensively used in the art and are well known by one skilled in the art.

In one embodiment, colorimetric or fluorogenic substrate and enzyme combination uses oxidoreductases such as horseradish peroxidase and a substrate such as 3,3'-diaminobenzidine (DAB) and 3-amino-9-ethylcarbazole (AEC), which yield a distinguishing color (brown and red, respectively). Other colorimetric oxidoreductase substrates that yield detectable products include, but are not limited to: 2,2-azino-bis(3-ethylbenzothiazoline-6-sulfonic acid) (ABTS), o-phenylenediamine (OPD), 3,3',5,5'-tetramethylbenzidine (TMB), o-dianisidine, 5-aminosalicylic acid, 4-chloro-1-naphthol. Fluorogenic substrates include, but are not limited to, homovanillic acid or 4-hydroxy-3-methoxyphenylacetic acid, reduced phenoxazines and reduced benzothiazines, including Amplex® Red reagent and its variants (U.S. Pat. No. 4,384,042) and reduced dihydroxanthenes, including dihydrofluoresceins (U.S. Pat. No. 6,162,931) and dihydrorhodamines including dihydrorhodamine 123. Peroxidase substrates that are tyramides (U.S. Pat. Nos. 5,196,306; 5,583,001 and 5,731,158) represent a unique class of peroxidase substrates in that they can be intrinsically detectable before action of the enzyme but are "fixed in place" by the action of a peroxidase in the process described as tyramide signal amplification (TSA). These substrates are extensively utilized to label antigen in samples that are cells, tissues or arrays for their subsequent detection by microscopy, flow cytometry, optical scanning and fluorometry.

In another embodiment, a colorimetric (and in some cases fluorogenic) substrate and enzyme combination uses a phosphatase enzyme such as an acid phosphatase, an alkaline phosphatase or a recombinant version of such a phosphatase in combination with a colorimetric substrate such as 5-bromo-6-chloro-3-indolyl phosphate (BCIP), 6-chloro-3-indolyl phosphate, 5-bromo-6-chloro-3-indolyl phosphate, p-nitrophenyl phosphate, or o-nitrophenyl phosphate or with a fluorogenic substrate such as 4-methylumbelliferyl phosphate, 6,8-difluoro-7-hydroxy-4-methylcoumarinyl phosphate (DiFMUP, U.S. Pat. No. 5,830,912) fluorescein diphosphate, 3-O-methylfluorescein phosphate, resorufin phosphate, 9H-(1,3-dichloro-9,9-dimethylacridin-2-one-7-yl) phosphate (DDAO phosphate), or ELF 97, ELF 39 or related phosphates (U.S. Pat. Nos. 5,316,906 and 5,443,986).

Glycosidases, in particular beta-galactosidase, beta-glucuronidase and beta-glucosidase, are additional suitable enzymes. Appropriate colorimetric substrates include, but are not limited to, 5-bromo-4-chloro-3-indolyl beta-D-galactopyranoside (X-gal) and similar indolyl galactosides, glucosides, and glucuronides, o-nitrophenyl beta-D-galactopyranoside (ONPG) and p-nitrophenyl beta-D-galactopyranoside. In one embodiment, fluorogenic substrates include resorufin beta-D-galactopyranoside, fluorescein digalactoside (FDG), fluorescein diglucuronide and their structural variants (U.S. Pat. Nos. 5,208,148; 5,242,805; 5,362,628; 5,576,424 and 5,773,236), 4-methylumbelliferyl beta-D-galactopyranoside, carboxyumbelliferyl beta-D-galactopyranoside and fluorinated coumarin beta-D-galactopyranosides (U.S. Pat. No. 5,830,912).

Additional enzymes include, but are not limited to, hydrolases such as cholinesterases and peptidases, oxidases such as glucose oxidase and cytochrome oxidases, and reductases for which suitable substrates are known.

Enzymes and their appropriate substrates that produce chemiluminescence are preferred for some assays. These include, but are not limited to, natural and recombinant forms of luciferases and aequorins. Chemiluminescence-producing substrates for phosphatases, glycosidases and oxidases such as those containing stable dioxetanes, luminol, isoluminol and acridinium esters are additionally useful.

In another embodiment, haptens such as biotin, are also utilized as labels. Biotin is useful because it can function in an enzyme system to further amplify the detectable signal, and it can function as a tag to be used in affinity chromatography for isolation purposes. For detection purposes, an enzyme conjugate that has affinity for biotin is used, such as avidin-HRP. Subsequently a peroxidase substrate is added to produce a detectable signal.

Haptens also include hormones, naturally occurring and synthetic drugs, pollutants, allergens, affector molecules, growth factors, chemokines, cytokines, lymphokines, amino acids, peptides, chemical intermediates, nucleotides and the like.

In certain embodiments, fluorescent proteins may be conjugated to the antibodies as a label. Examples of fluorescent proteins include green fluorescent protein (GFP) and the phycobiliproteins and the derivatives thereof. The fluorescent proteins, especially phycobiliprotein, are particularly useful for creating tandem dye labeled labeling reagents. These tandem dyes comprise a fluorescent protein and a fluorophore for the purposes of obtaining a larger stokes shift wherein the emission spectra is farther shifted from the wavelength of the fluorescent protein's absorption spectra. This is particularly advantageous for detecting a low quantity of antigen in a sample wherein the emitted fluorescent light is maximally optimized, in other words little to none of the emitted light is reabsorbed by the fluorescent protein. For this to work, the fluorescent protein and fluorophore function as an energy transfer pair wherein the fluorescent protein emits at the wavelength that the fluorophore absorbs at and the fluorphore then emits at a wavelength farther from the fluorescent proteins than could have been obtained with only the fluorescent protein. A particularly useful combination is the phycobiliproteins disclosed in U.S. Pat. Nos. 4,520,110; 4,859,582; 5,055,556 and the sulforhodamine fluorophores disclosed in U.S. Pat. No. 5,798,276, or the sulfonated cyanine fluorophores disclosed in U.S. Pat. Nos. 6,977,305 and 6,974,873; or the sulfonated xanthene derivatives disclosed in U.S. Pat. No. 6,130,101 and those combinations disclosed in U.S. Pat. No. 4,542,104. Alternatively, the fluorophore functions as the energy donor and the fluorescent protein is the energy acceptor.

In certain embodiments, the label is a radioactive isotope. Examples of suitable radioactive materials include, but are not limited to, iodine ($^{121}$I, $^{123}$I, $^{125}$I, $^{131}$I), carbon ($^{14}$C), sulfur ($^{35}$S), tritium ($^{3}$H), indium ($^{111}$In, $^{112}$In, $^{113m}$In, $^{115m}$In), technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{135}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, and $^{97}$Ru.

Medical Treatments and Uses

The antibodies and binding fragments thereof of the invention and variants thereof may be used for the treatment of influenza A virus infection, for the prevention of influenza A virus infection and/or for the detection, diagnosis and/or prognosis of influenza A virus infection.

Methods of diagnosis may include contacting an antibody or an antibody fragment with a sample. Such samples may be tissue samples taken from, for example, nasal passages, sinus cavities, salivary glands, lung, liver, pancreas, kidney, ear, eye, placenta, alimentary tract, heart, ovaries, pituitary, adrenals, thyroid, brain or skin. The methods of detection, diagnosis, and/or prognosis may also include the detection of an antigen/antibody complex.

In one embodiment, the invention provides a method of treating a subject by administering to the subject an effective amount of an antibody or an binding fragment thereof, according to the invention, or a pharmaceutical composition that includes the antibody or binding fragment thereof. In one embodiment, the antibody or binding fragment thereof is substantially purified (i.e., substantially free from substances that limit its effect or produce undesired side-effects) . In one embodiment, the antibody or binding fragment thereof of the invention is administered post-exposure, or after the subject has been exposed to influenza A virus or is infected with influenza A virus. In another embodiment, the antibody or binding fragment thereof of the invention is administered pre-exposure, or to a subject that has not yet been exposed to influenza A virus or is not yet infected with influenza A virus. In one embodiment, the antibody or binding fragment thereof of the invention is administered to a subject that is sero-negative for one or more influenza A subtypes. In another embodiment, the antibody or binding fragment thereof of the invention is administered to a subject that is sero-positive for one or more influenza A subtypes. In one embodiment, the antibody or binding fragment thereof of the invention is administered to a subject within 1, 2, 3, 4, 5 days of infection or symptom onset. In another embodiment, the antibody or binding fragment thereof of the invention can be administered to a subject after 1, 2, 3, 4, 5, 6, or 7 days, and within 2, 3, 4, 5, 6, 7, 8, 9 or 10 days after infection or symptom onset.

In one embodiment, the method reduces influenza A virus infection in the subject. In another embodiment, the method prevents, reduces the risk or delays influenza A virus infection in the subject. In one embodiment, the subject is a mammal. In a more particular embodiment, the subject is human. In one embodiment, the subject includes, but is not limited to, one who is particularly at risk of or susceptible to influenza A virus infection, including, for example, an immunocompromised subject.

Treatment can be a single dose schedule or a multiple dose schedule and the antibody or binding fragment thereof of the invention can be used in passive immunization.

In one embodiment, the antibody or binding fragment thereof of the invention is administered to a subject in combination with one or more antiviral medications. In one embodiment, the antibody or binding fragment thereof of the invention is administered to a subject in combination with one or more small molecule antiviral medications. Small molecule antiviral medications include neuraminidase inhibitors such as oseltamivir (TAMIFLU®), zanamivir (RELENZA®) and adamantanes such as Amantadine and rimantadine.

In another embodiment, the invention provides a composition for use as a medicament for the prevention or treatment of an influenza A virus infection. In another embodiment, the invention provides the use of an antibody or binding fragment thereof of the invention and/or a protein comprising an epitope to which an antibody or binding fragment thereof of the invention binds in the manufacture of a medicament for treatment of a subject and/or diagnosis in a subject.

Antibodies and fragments thereof as described in the present invention may also be used in a kit for the diagnosis of influenza A virus infection. Further, epitopes capable of binding an antibody of the invention may be used in a kit for monitoring the efficacy of vaccination procedures by detecting the presence of protective anti-influenza A virus antibodies. Antibodies, antibody fragment, or variants and derivatives thereof, as described in the present invention may also be used in a kit for monitoring vaccine manufacture with the desired immunogenicity.

The invention also provides a method of preparing a pharmaceutical composition, which includes the step of admixing a monoclonal antibody with one or more pharmaceutically-acceptable carriers, wherein the antibody is a monoclonal antibody according to the invention described herein.

Various delivery systems are known and can be used to administer the antibody or binding fragment thereof of the invention, including, but not limited to, encapsulation in liposomes, microparticles, microcapsules, recombinant cells capable of expressing the antibody or antibody fragment, receptor-mediated endocytosis, construction of a nucleic acid as part of a retroviral or other vector, delivery of naked nucleotide acids by electroporation delivery technology (as described in Muthumani et al., PLoS One. 2013 Dec. 31; 8(12):e84234. doi: 10.1371/journal.pone.0084234. eCollection 2013) etc. Methods of introduction include, but are not limited to, intradermal, intramuscular, intraperitoneal, intravenous, subcutaneous, intranasal, epidural, and oral routes. The compositions may be administered by any convenient route, for example by infusion or bolus injection, by absorption through epithelial or mucutaneous linings (e.g., oral mucosa, rectal and intestinal mucosa, etc.) and may be administered together with other biologically active agents, including, but not limited to small molecule antiviral compositions. Administration can be systemic or local. Pulmonary administration can also be employed, e.g., by use of an inhaler or nebulizer, and formulation with an aerosolizing agent. In yet another embodiment, the composition can be delivered in a controlled release system.

The present invention also provides pharmaceutical compositions. Such compositions include a therapeutically effective amount of an antibody or binding fragment thereof of the invention, and a pharmaceutically acceptable carrier. The term "pharmaceutically acceptable" as used herein, means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. In one embodiment, the pharmaceutical composition contains a therapeutically effective amount of the antibody or binding fragment thereof, preferably in purified form, together with a suitable amount of carrier so as to provide the form for proper administration to the patient. The formulation should suit the mode of administration.

Typically, for antibody therapeutics, the dosage administered to a patient is between about 0.1 mg/kg to 100 mg/kg of the patient's body weight.

LIST OF FIGURES

Figure 10:
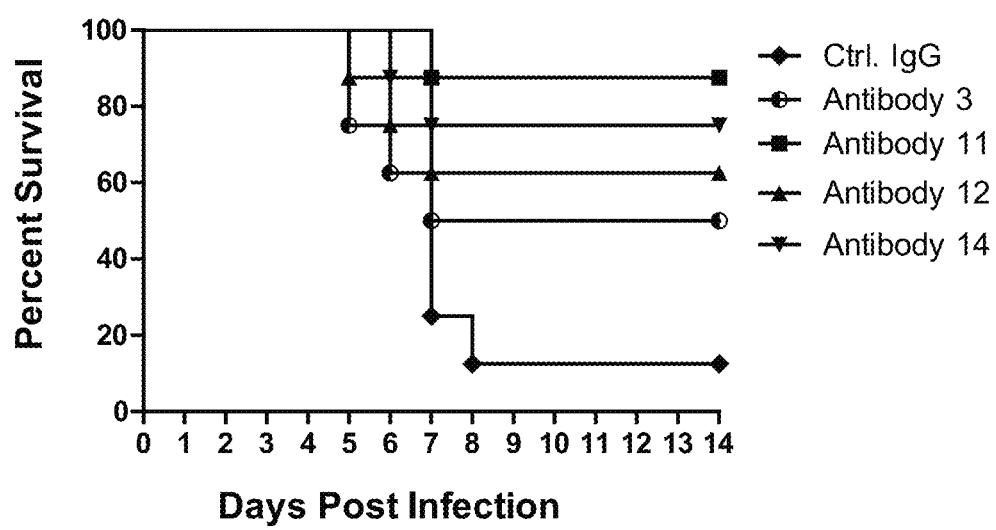

FIG. 10 shows immunoblots of uncleaved (HA0), recombinant H1 HA after digestion with trypsin for 5, 10 or 20 minutes. Digestion reactions contained either HA alone (input), or HA pre-treated with Fl6v4 (disclosed in WO2013/011347A1), Antibody 3, FE17.23 (globular head specific mAb) (Corti D et al., 2010, J Clin Invest 120) or non-relevant control antibody (Ctrl. IgG).

Figure 1A:
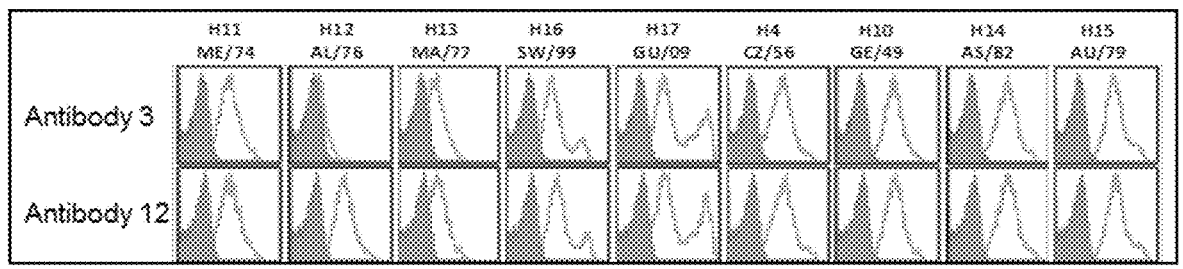
FIG. 1A shows the binding of Antibody 3 and Antibody 12 to surface expressed HA protein of subtypes H11, H12, H13, H16, H17, H4, H10, H14, and H15. Histograms depict the number of cells vs the florescence intensity of antibody binding to HA transfected cells in white or mock transfected cells in grey.
Figure 1B:
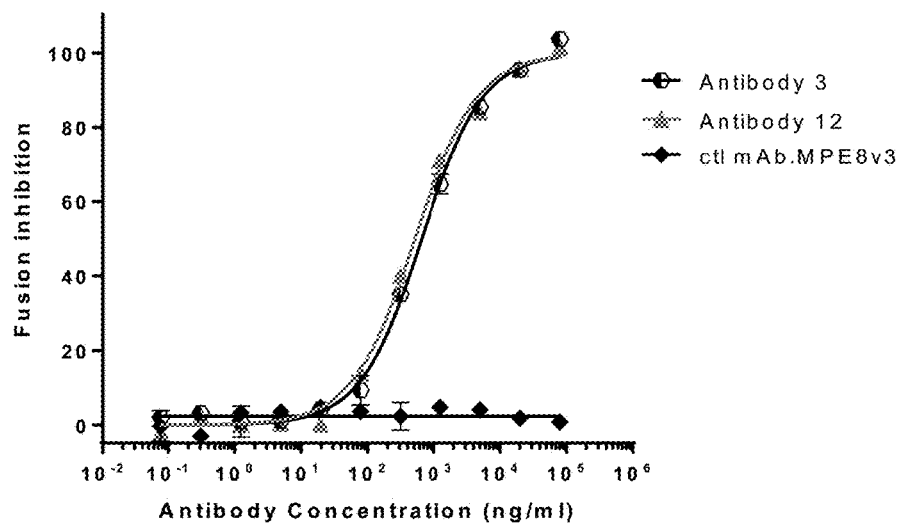
FIG. 1B shows the percent inhibition of low pH induced fusion of chicken red blood cells and A/Puerto Rico/8/34 in the presence of Antibody 3, Antibody 12, or MPE8v3 (non-relevant viral fusion protein antibody) (Corti D et al., 2013, Nature 501).
Figure 1C:
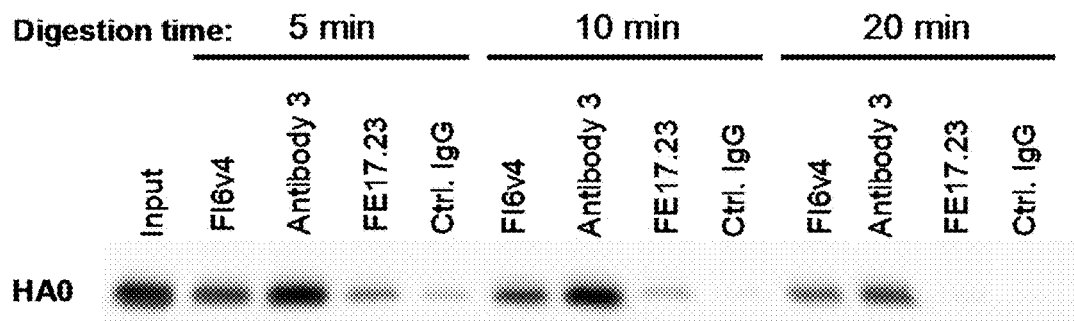
Figure 1D:
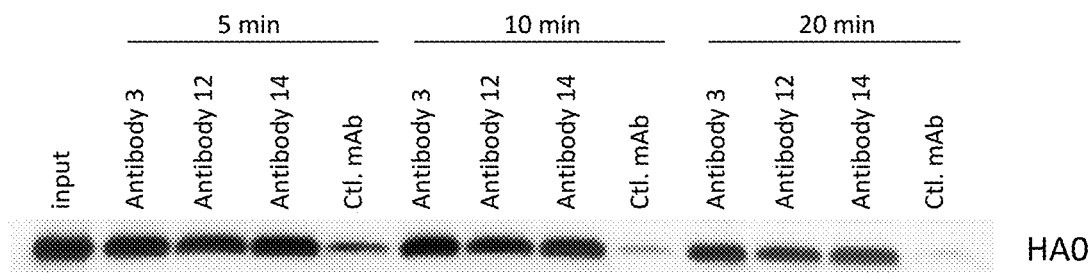

FIG. 1D shows immunoblots of uncleaved (HA0), recombinant H1 HA after digestion with trypsin of 5, 10 or 20 minutes. Digestion reactions contained either HA alone (input), or HA pre-treated with Antibody 3, Antibody 12, Antibody 14, or non-relevant control antibody (Ctrl. IgG).

Figure 2:
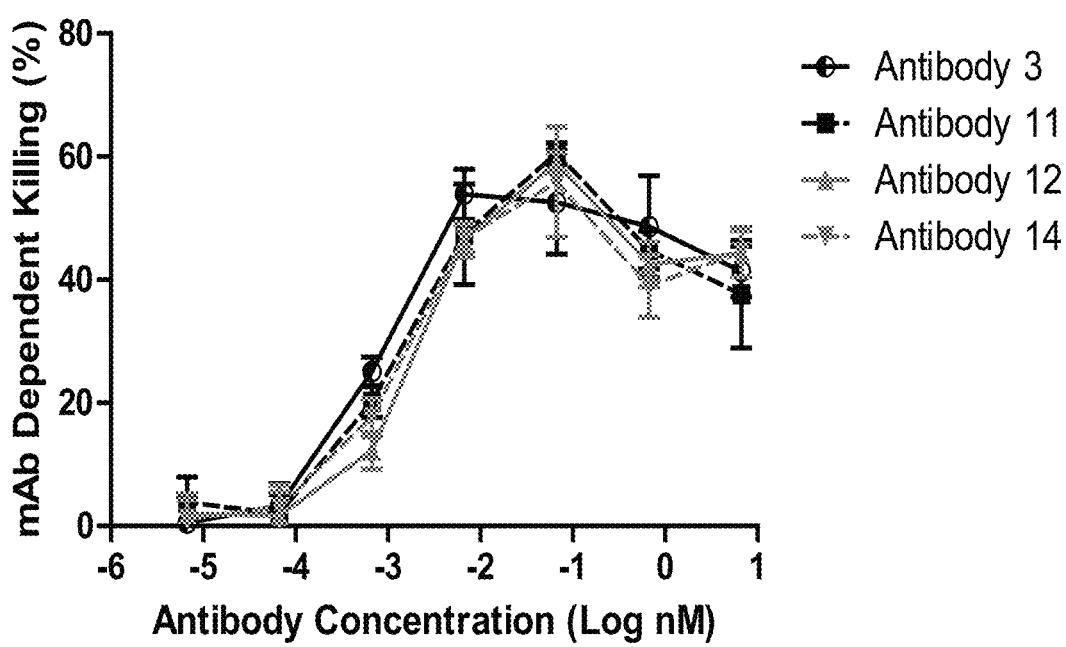

FIG. 2 shows the percentage of NK cell mediated killing of A/HK/8/68 infected MDCK cells in the presence of increasing amount of Antibody 3, Antibody 11, Antibody 12, and Antibody 14.

Figure 3:
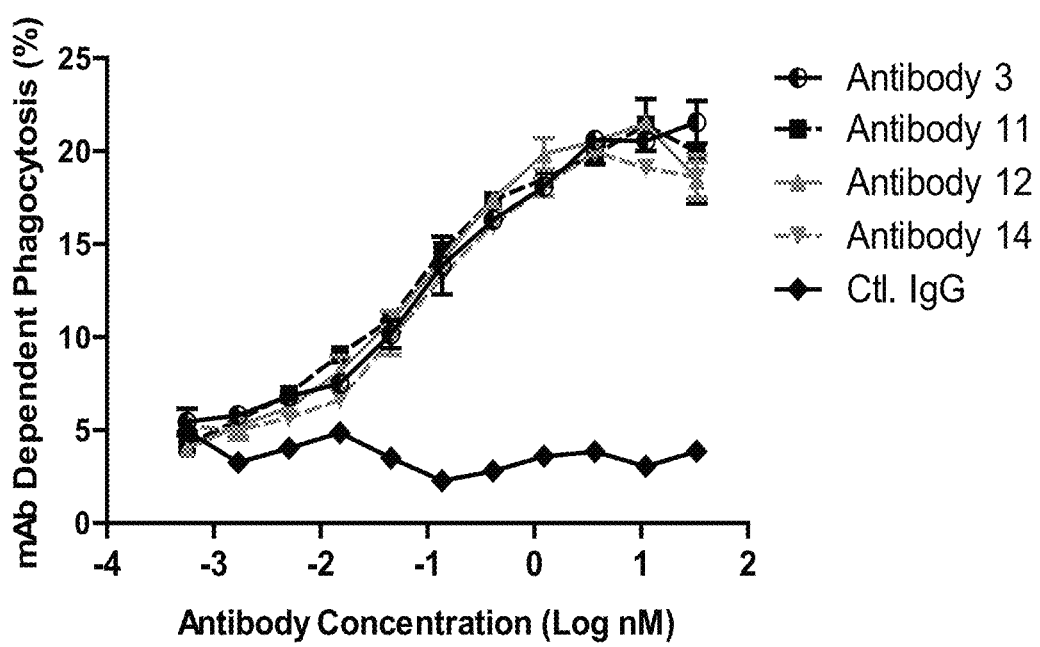

FIG. 3 shows the percentage of macrophages that phagocytosed A/HK/8/68 HA expressing MDCK target cells in the presence of increasing amount of Antibody 3, Antibody 11, Antibody 12, and Antibody 14, or non-relevant isotype control (Ctrl. IgG).

Figure 4:
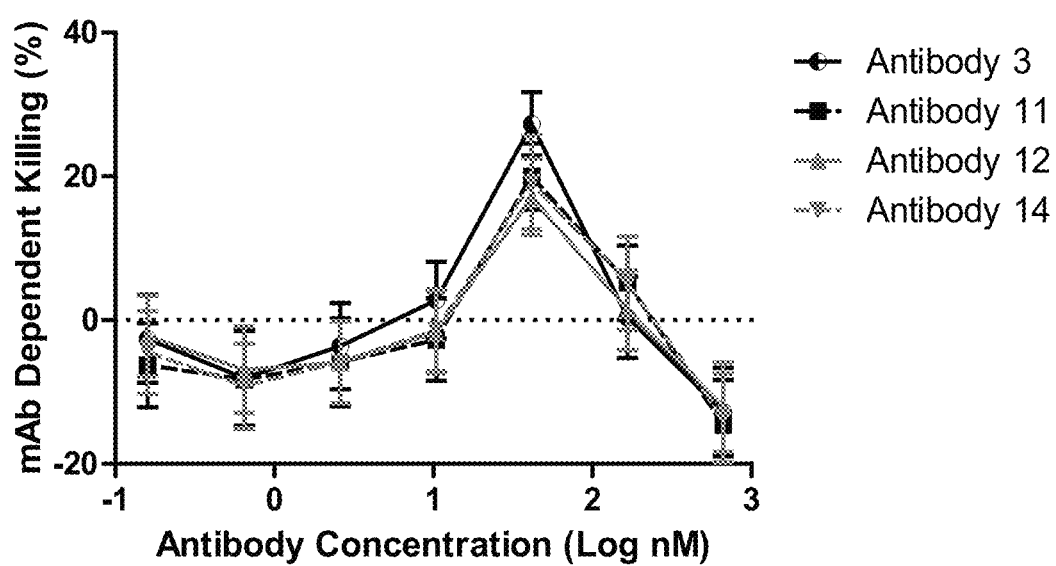

FIG. 4 shows the percentage of complement dependent killing of A/PR/8/34 infected MDCK cells in the presence of increasing amount of Antibody 3, Antibody 11, Antibody 12, and Antibody 14.

Figure 5:
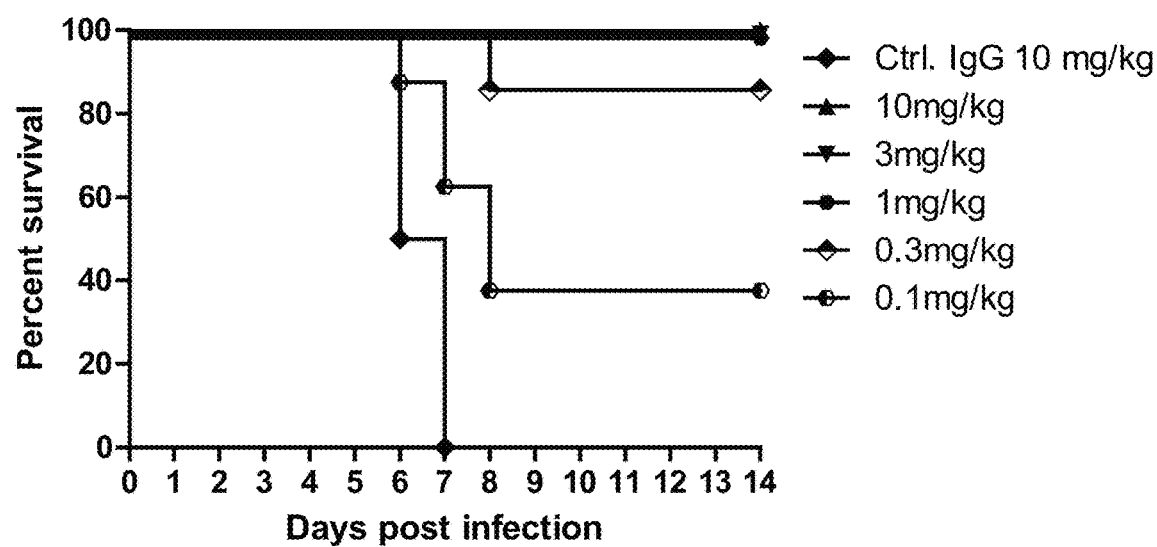

FIG. 5 shows the percentage of surviving animals in each group of a study when different concentrations of Antibody 3 or a non-relevant control antibody (Ctrl. IgG) were administered to mice 4 hours before infection with a lethal dose of H1N1 influenza virus.

Figure 6:
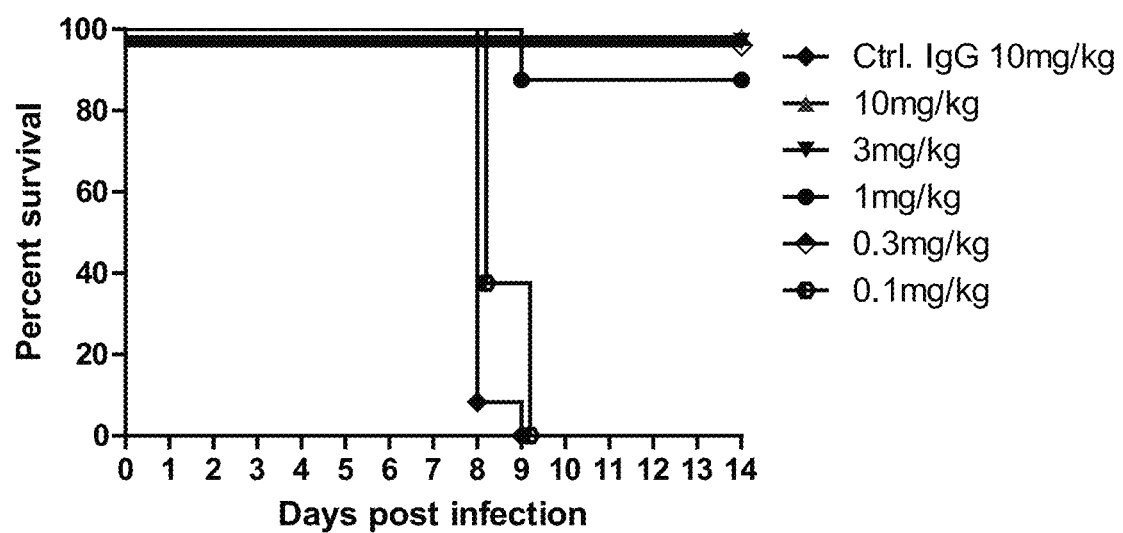

FIG. 6 shows the percentage of surviving animals in each group of a study in which different concentrations of Antibody 3 or a non-relevant control antibody (Ctrl. IgG) were administered to mice 4 hours before infection with a lethal dose of H3 influenza virus.

Figure 7:
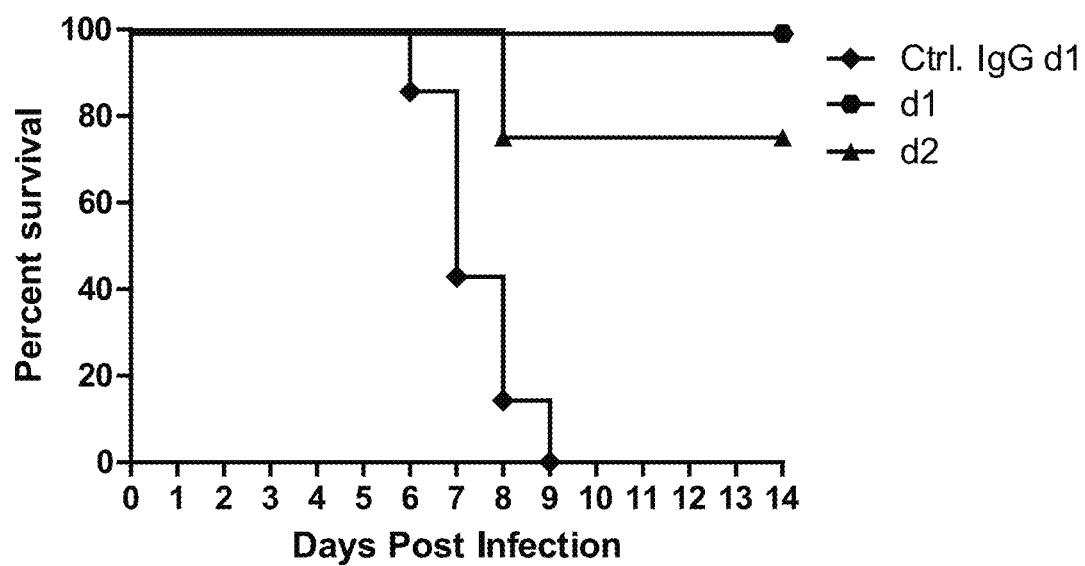

FIG. 7 shows the percentage of surviving animals in each group when mice were infected with a lethal dose of H1N1 influenza virus and treated at different time points (1 and 2 days post-infection) with 30 mg/kg of Antibody 3 or a non-relevant control antibody (Ctrl. IgG).

Figure 8:
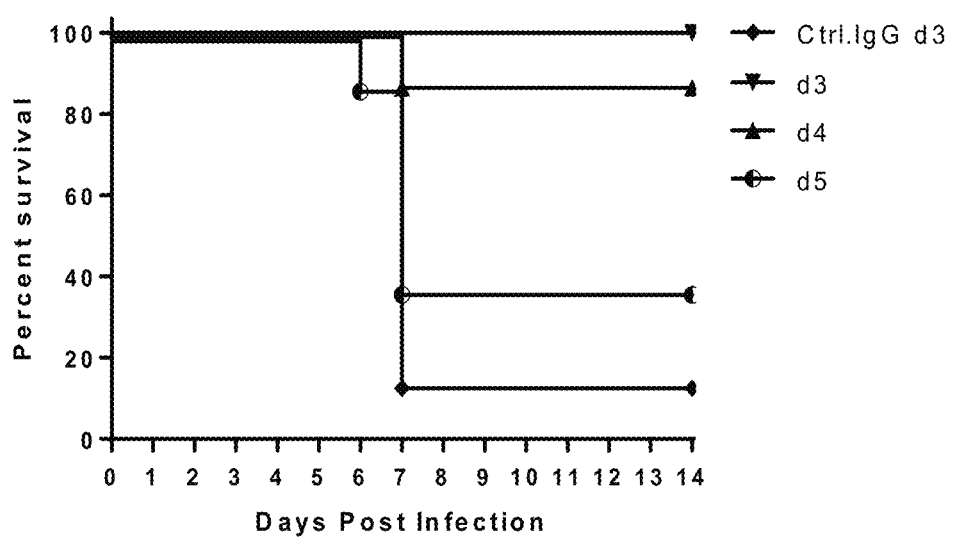

FIG. 8 shows the percentage of surviving animals in each group of a study in which mice were infected with a lethal dose of H3 influenza virus and treated at different time points (3, 4 and 5 days post-infection) with 30 mg/kg of Antibody 3 or a non-relevant control antibody (Ctrl. IgG).

Figure 9:
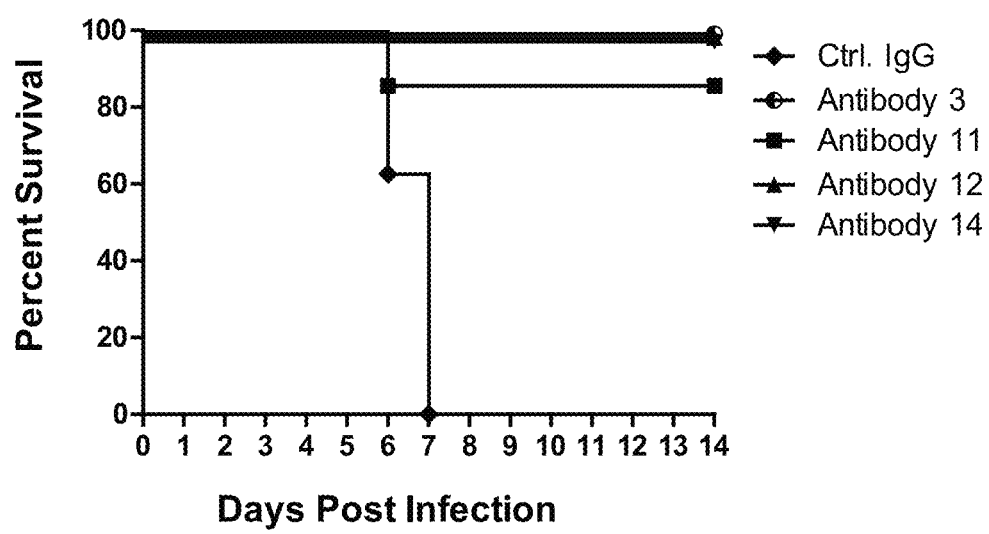

FIG. 9 shows the percentage of surviving animals in each group of a study in which mice were infected with a lethal dose of H1N1 influenza virus and treated at 1 day post infection with 2 mg/kg of Antibody 3, Antibody 11, Antibody 12, Antibody 14 or a non-relevant control antibody (Ctrl. IgG).

FIG. 10 shows the percentage of surviving animals in each group of a study in which mice were infected with a lethal dose of H3 influenza virus and treated at 2 day post infection with 3 mg/kg of Antibody 3, Antibody 11, Antibody 12, Antibody 14 or a non-relevant control antibody (Ctrl. IgG).

Figure 11:
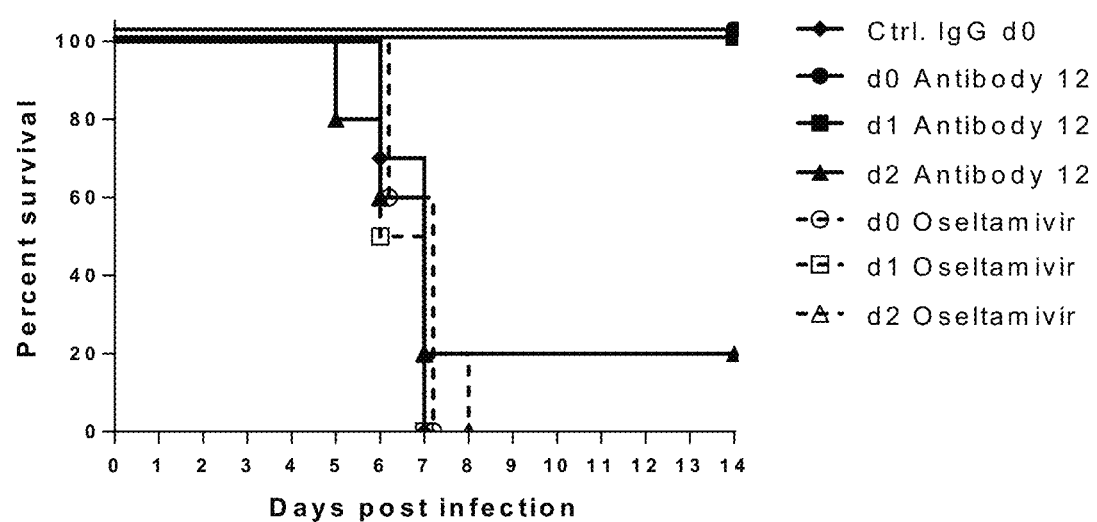

FIG. 11 shows the percentage of surviving animals in each group of a study in which mice were infected with a lethal dose of H1N1 influenza virus and treatment of 25 mg/kg BID oseltamivir for 5 days, 10 mg/kg of Antibody 12, or 10 mg/kg of non-relevant control antibody (Ctrl. IgG) was initiated at different time points (4 hr before, 1 day post, or 2 days post infection).

Figure 12:
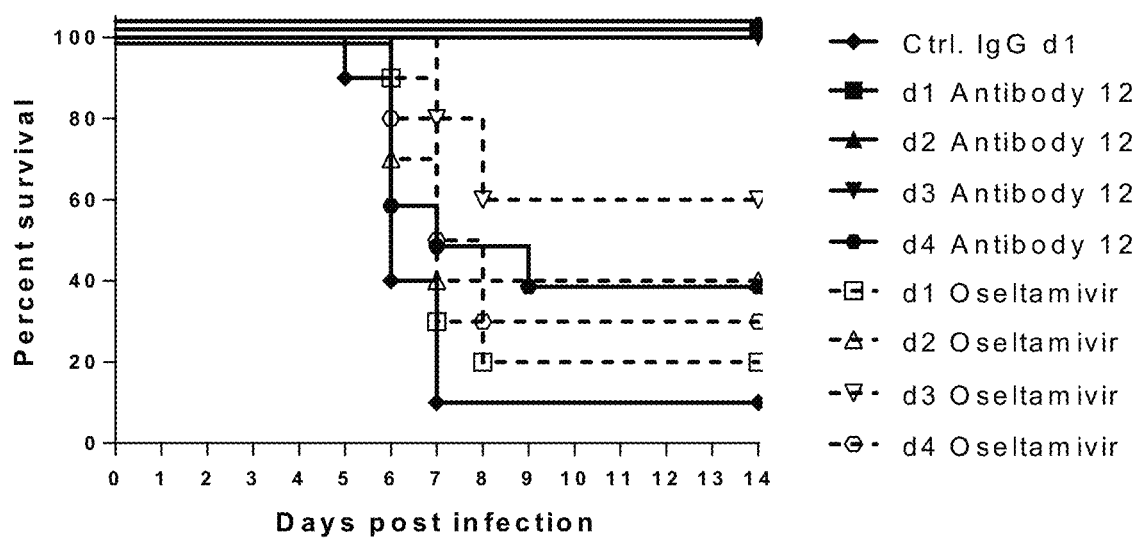

FIG. 12 shows the percentage of surviving animals in each group of a study in which mice were infected with a lethal dose of H3 influenza virus and treatment of 25 mg/kg oraloseltamivir twice daily (BID) for 5 days, or single dose 10 mg/kg of Antibody 12, or 10 mg/kg of a non-relevant control antibody (Ctrl. IgG) that was initiated at various time points (1, 2, 3 or 4 days post infection).

Figure 13:
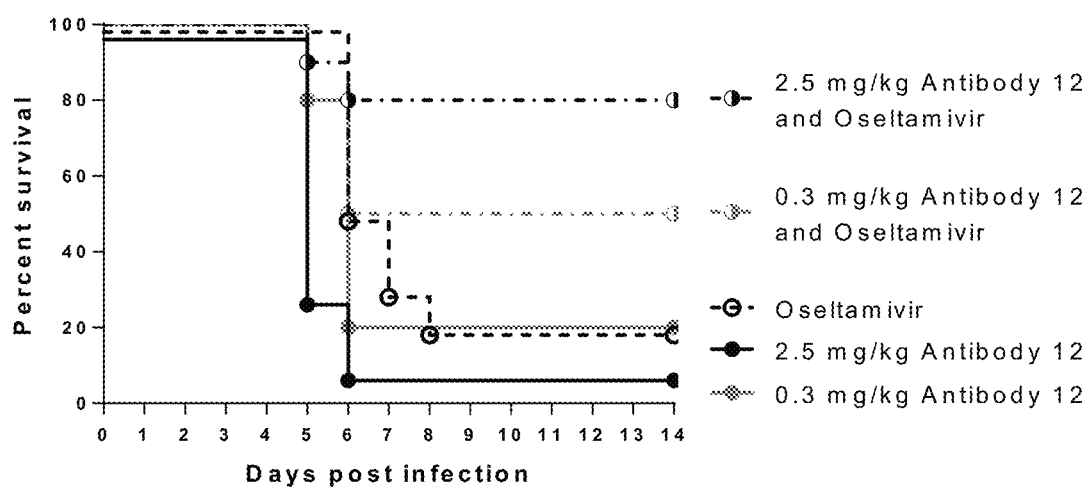

FIG. 13 shows the percentage of surviving animals in each group in a study that mice were infected with a lethal dose of H3 influenza virus and treated with Antibody 12 at 2.5 mg/kg or 0.3 mg/kg single dose, oseltamivir at 25 mg/kg BID for 5 days, or a combination of Antibody 12 at 2.5 mg/kg or 0.3 mg/kg and oseltamivir at 25 mg/kg BID for 5 days at 2 days post infection.

Figure 14:
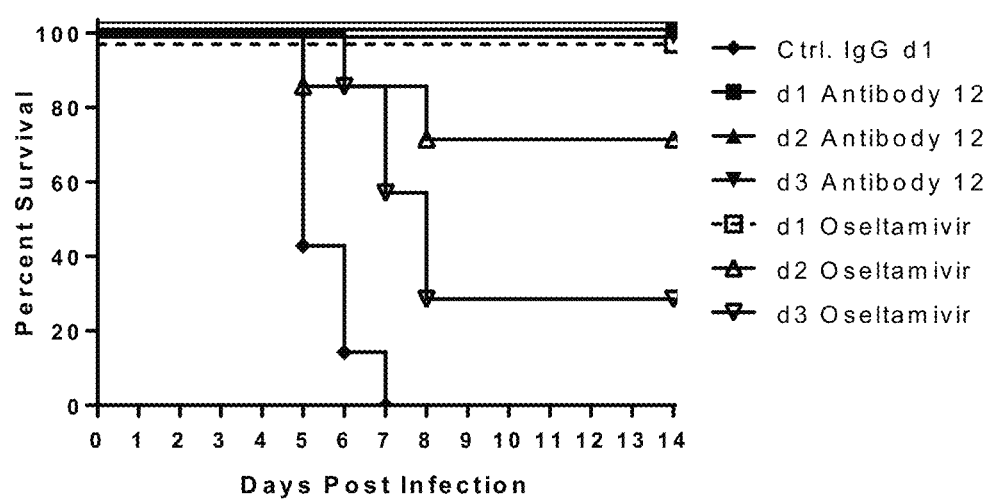

FIG. 14 shows the percentage of surviving ferrets in each group of a study after infection with a lethal dose of H5N1 influenza virus and treatment with 25 mg/kg single dose Antibody 12, 25 mg/kg BID oseltamivir for 5 days, or a non-relevant control antibody (Ctrl. IgG) at 1, 2, or 3 days post infection.

FIG. 15 shows an alignment of HA2 Protein of Influenza A Strains Used in MARM selection.

Figure 16:
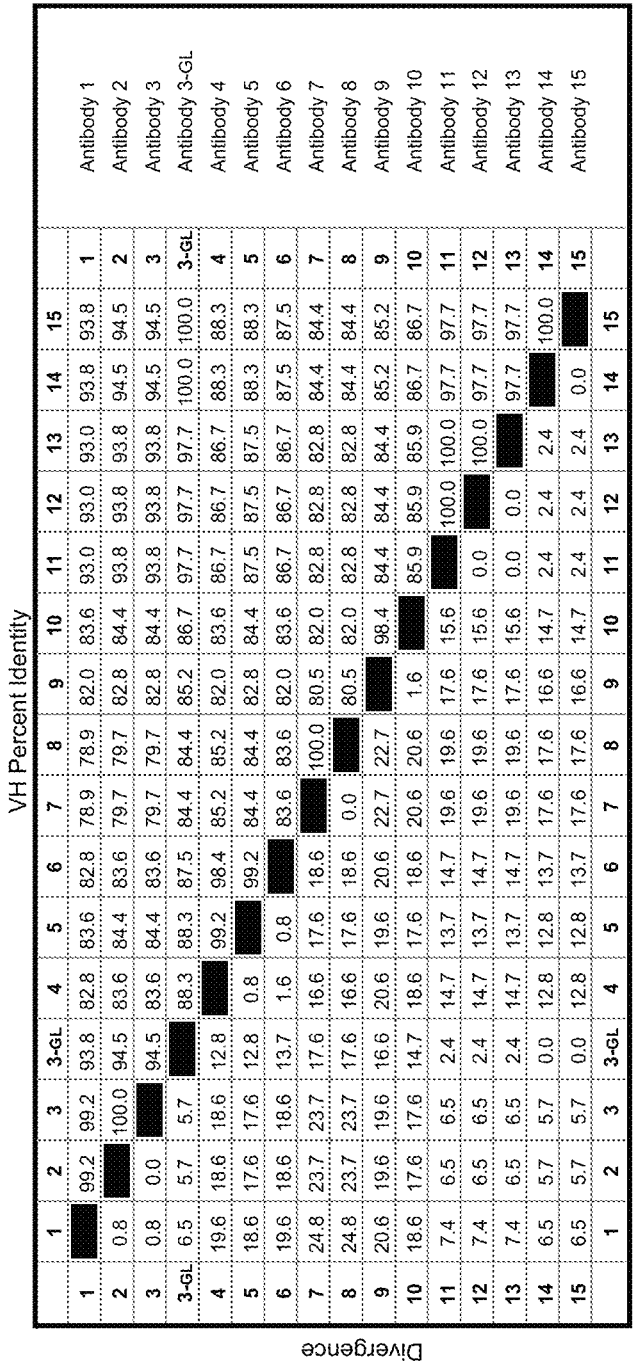

FIG. 16 shows the VH percent identity of anti-HA Antibodies 1-15 and Antibody 3-GL.

Figure 17:
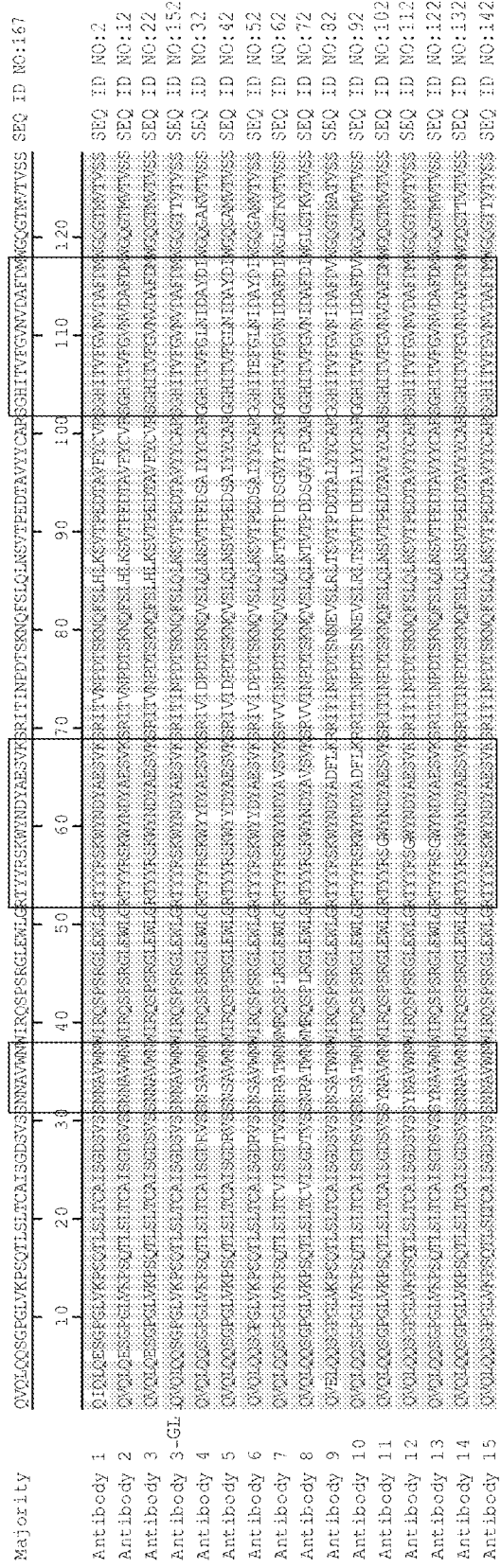

FIG. 17 shows the VH alignment of anti-HA Antibodies 1-15 and Antibody 3-GL.

FIG. 18 shows the VL percent identity of anti-HA Antibodies 1-15 and Antibody 3-GL.

Figure 19:
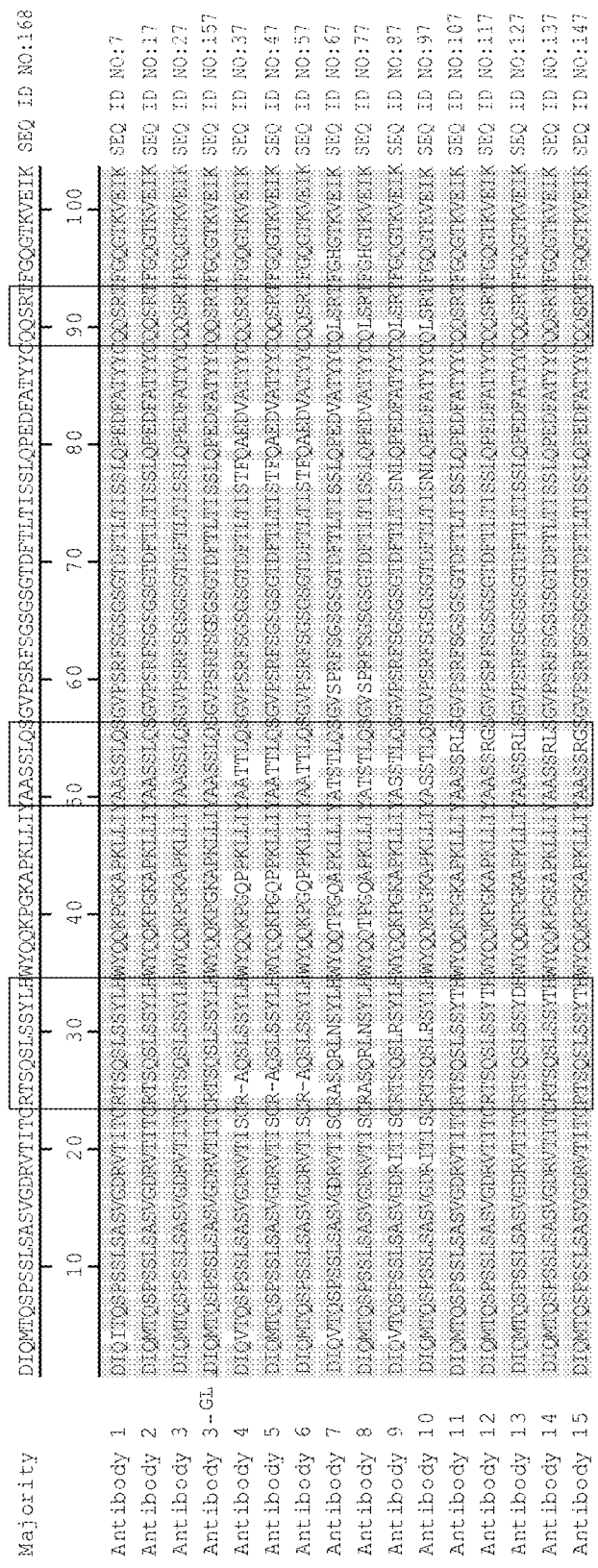

FIG. 19 shows the VL alignment of anti-HA Antibodies 1-15 and Antibody 3-GL.

EXAMPLES

Example 1. Construction and Optimization of Human Monoclonal Antibodies Isolated from Memory B Cells The CD22+ IgG+ B cells were sorted from cryopreserved peripheral blood mononuclear cells (PBMCs) of a donor selected for high titers of heterosubtypic antibodies and immortalized at 3 cells/well using Epstein Barr Virus (EBV) and CpG oligodeoxynucleotide 2006 and feeder cells. Culture supernatants containing antibodies were harvested after 14 days and screened by ELISA binding assay to determine the binding activity against H5 (A/Vietnam/1203/04) and H7 (A/NLD/03) hemagglutinin (HA), respectively. Four B cell clones (Antibody 1, Antibody 4, Antibody 7, and Antibody 9) were found to bind specifically to both HAs and were therefore collected. The VH and VL genes of these clones were sequenced and found to be clonally related according to the homology analysis performed on VH and VL V, D and J fragments using the Kabat database. Of note, the VH of Antibody 4 was found to have a degenerate nucleotide site in the HCDR3 encoding for either valine (encoded in Antibody 5) or glutamate (encoded in Antibody 6). The VH and VL genes of the four antibodies were cloned into IgG1 expression vectors (minor sequence modifications to facilitate cloning and or codon optimization resulted in the five antibodies; Antibody 3, Antibody 5, Antibody 6, Antibody 8 and Antibody 10; used in the following Examples) and recombinant antibodies were produced by transient transfection of mammalian cell lines derived from HEK or CHO cells. Supernatants from transfected cells were collected after 7-10 days of culture, and IgGs were affinity purified by Protein A chromatography, and dialyzed into PBS. Antibody 3 was further optimized to create variants in which non-germline encoded somatic mutations located in the framework regions were changed to the germline encoded amino acid, and the CDR regions were subjected to parsimonious mutagenesis. Full IgG constructs containing different mutations were expressed as described above and the crude supernatants were screened by ELISA to select clones that had increased binding activity to H3 and H1 HA proteins. ELISA was performed using a coating concentration of 0.15 pg/ml of rabbit anti-human IgG in order to capture and normalize IgG from the supernatants, and then 0.5 pg/ml of biotinylated HA subtype H1 (A/California/7/04 (H1N1)) or subtype H3 (A/Perth/16/09 (H3N2)) was added and incubated for one hour. Binding was detected by the addition of streptavidin-HRP (1:5000), and development absorbance was read at 450 nm. The beneficial single mutations conferring better binding were combined and cloned into a combinatorial library, which were expressed and screened by ELISA as described above. This library approach resulted in the creation of 5 additional Antibody 3 variants that were further characterized (Antibodies 11-15).

Example 2. Anti-HA Neutralizing Antibody (nAb) Binds to HA of Different Subtypes To test if the epitope of the anti-HA antibodies is conserved among HAs of different subtypes, a HA cross-reactivity ELISA binding assay was performed. A 384-well Maxisorb ELISA plate (Nunc) was coated overnight at 4° C. with 0.5 ug/ml recombinant HA (rHA), subtype H1 (A/California/7/09 (H1N1)), subtype H2 (A/Swine/MO/06 (H2N3)), subtype H3 (A/Perth/16/09 (H3N2)), subtype H5 (A/Vietnam/1203/04(H5N1)), subtype H6 (A/teal/HK/W312/97(H6N1)), subtype H7 (A/Netherlands/219/03 (H7N7)) and subtype H9 (A/chicken/HK/G9/97 (H9N2)) in PBS. The plate was washed with PBS containing 0.1% v/v Tween-20 to remove uncoated protein and subsequently blocking solution containing 1% (w/v) casein (Thermo Scientific) was added and incubated for 1 hr at room temperature. The blocking solution was discarded and 3-fold serially diluted anti-HA antibodies in blocking solution (Casein-PBS (Thermo Scientific) were added and incubated for 1 hr at room temperature. The plate was washed three times and bound antibodies were detected using a peroxidase-conjugated mouse anti-human IgG antibody (Jackson). The binding activity of antibody was calculated by either measuring the chemiluminescent signal after addition of Supersignal Pico substrate (Thermo Scientific) or by measuring the color change at 450 nm after incubation with Tetramethylbenzidine (TMB) one component substrate (KPL) followed by the addition of 2N sulfuric acid to stop the reaction.

TABLE 1

| | Binding to rHA by ELISA ($EC_{50}$, ug/ml) | | | | | | |
|---|---|---|---|---|---|---|---|
| | H1 A/CA/7/09 | H2 A/swine/MO/06 | H5 A/VN/1203/04 | H6 A/HK/W312/97 | H9 A/HK/G9/97 | H3 A/Perth/16/09 | H7 A/NLD/219/03 |
| Antibody 3 | 0.026 | 0.028 | 0.022 | 0.043 | 0.012 | 0.019 | 0.020 |
| Antibody 5 | 0.045 | 0.048 | 0.041 | 0.047 | >6 | 0.030 | 0.024 |
| Antibody 6 | 0.311 | 0.213 | 0.256 | 0.214 | >6 | 0.064 | 0.116 |

TABLE 1-continued

| | Binding to rHA by ELISA (EC$_{50}$, ug/ml) | | | | | | |
|---|---|---|---|---|---|---|---|
| | H1 A/CA/7/09 | H2 A/swine/MO/06 | H5 A/VN/1203/04 | H6 A/HK/W312/97 | H9 A/HK/G9/97 | H3 A/Perth/16/09 | H7 A/NLD/219/03 |
| Antibody 8 | 0.069 | 0.058 | 0.044 | 0.091 | >6 | 0.067 | 0.015 |
| Antibody 10 | 0.073 | 0.075 | 0.058 | 0.097 | 2.699 | 0.049 | 0.034 |

Table 1 shows that all anti-HA IgGs tested bound to recombinant HA of subtypes H1, H2, H3, H5, H6, H9 and H7. Recombinant HA of subtype H9 was recognized by Antibody 3 and Antibody 10, but not by Antibody 5, Antibody 6 and Antibody 8 at the highest concentration of antibody tested (6 ug/ml). This indicates that the epitopes of the majority of these anti-HA IgGs are conserved among HA molecules of different subtypes.

TABLE 2

| | Binding to rHA by ELISA (EC$_{50}$, ug/ml) | | | | | | |
|---|---|---|---|---|---|---|---|
| | H1 A/CA/7/09 | H2 A/swine/MO/06 | H5 A/VN/1203/04 | H6 A/HK/W312/97 | H9 A/HK/G9/97 | H3 A/Perth/16/09 | H7 A/NLD/219/03 |
| Antibody 3 | 0.045 | 0.095 | 0.099 | 0.072 | 0.171 | 0.129 | 0.258 |
| Antibody 11 | 0.085 | 0.126 | 0.168 | 0.129 | 0.164 | 0.176 | 0.553 |
| Antibody 12 | 0.059 | 0.088 | 0.084 | 0.083 | 0.098 | 0.028 | 0.061 |
| Antibody 13 | 0.050 | 0.062 | 0.080 | 0.097 | 0.161 | 0.023 | 0.049 |
| Antibody 14 | 0.048 | 0.079 | 0.061 | 0.073 | 0.095 | 0.030 | 0.064 |
| Antibody 15 | 0.028 | 0.042 | 0.035 | 0.043 | 0.065 | 0.032 | 0.035 |

Table 2 shows that all anti-HA IgGs variants tested bound to recombinant HA of group 1 subtypes H1, H2, H5, H6 and H9 with similar ECK values. All the variants bound to group 2 HA proteins (H3 and H7), however, Antibody 11 and Antibody 3 showed decreased activity with increased ECK values compared to the Antibodies 12-15.

To extend these binding results to include more diverse HA subtypes, we performed additional binding studies using a flow cytometry based binding to HA transfected cells. In this assay, HEK cells were transiently transfected with full-length wild type HA expressing plasmids of subtype H4 A/duck/Czechoslovakia/56 (H4N6)), subtype H10 (A/chicken/Germany/N49 (H10N7)), subtype H11 (A/duck/Memphis/546/74 (H11N9)), subtype H12 (A/duck/Alberta/60/76 (H12N5)), subtype H13 (A/gull/Maryland/704/77 (H13N6)), subtype H14 (A/mallard/Astrakhan/263/82 (H14N5)), subtype H15 (A/shearwater/West Australia/2576/79 (H15N9)), subtype H16 (A/black-headed gull/Sweden/2/99 (H16N3)), and subtype H17 (A/little yellow-shouldered bat/Guatemala/164/2009 (H17N10)). Forty-eight hours after transfection, cells were detached with trypsin, and incubated with 5 ug/ml of Antibody 3 or Antibody 12 on ice for 1 hour. After the hour incubation, the antibody bound to cell-surface expressed HA protein was then stained with a goat anti-human IgG Daylight 649 (Jackson ImmunoResearch), and which was detected by flow cytometry. FIG. 1A shows the shift in fluorescence intensity when antibody is bound to HA expressing cells (white) vs mock-transfected cells (grey) from each of the subtypes. Antibody 3 bound to all HAs tested with the exception of H12, while Antibody 12 bound to all HAs tested from both groups (group 1 H11, H12, H13, H16, and H17 and group 2 H4, H10, H14, and H15)

Example 3 Kinetic Characterization of the HA Binding to Antibody 3 and Antibody 5 IgG1 by Using Octet Affinity measurements were performed using a ForteBio Octet QK 384 Kinetic Analyzer (Menlo Park, Calif.) in 384 slanted-well plates. All reagents were diluted in Octet Kinetics Buffer (ForteBio). His-tagged HA of different subtypes: subtype H1 (A/California/7/04 (H1N1)) and subtype H3 (A/Perth/16/09 (H3N2)) were immobilized onto anti-His sensors at 10 µg/mL. Anti-HA mAb association/dissociation were then monitored in 2-fold dilutions from 100 nM, plus a zero mAb control.

Association and dissociation raw data were corrected for any drift in the zero mAb controls, and then exported to GraphPad Prism (San Diego, Calif.) for affinity curve fitting. Data were fitted using global association/dissociation fitting with an imposed limit of $>5\times10^{-6}$ sec$^{-1}$. As shown in Table 3, both antibodies have a very high affinity binding to H1 at pM level with a slow dissociation rate under limit of detection. Similar $K_{on}$, $K_{off}$ and Kd of both antibodies were observed with H3 trimer at sub-nM level.

TABLE 3

Kinetic Binding Analysis of Pan A mAbs on rHA by Octet

| | H1 A/CA/7/09 | | | H3 A/Perth/16/09 | | |
|---|---|---|---|---|---|---|
| | $K_{on}$ (e5 M$^{-1}$s$^{-1}$) | $K_{off}$ (e$^{-6}$ s$^{-1}$) | Kd (pM) | $K_{on}$ (e5 M$^{-1}$s$^{-1}$) | $K_{off}$ (e$^{-6}$s$^{-1}$) | Kd (pM) |
| Antibody 3 | 5.3 | <5 | 11 | 3.3 | 62 | 188 |
| Antibody 5 | 10 | <5 | 5 | 2.6 | 88 | 338 |

Example 4 In Vitro Cross-Reactive Neutralizing Activity of Anti-HA IgG1s Against Virus of Different Subtypes The microneutralization assay (MNA) was modified from a previously described accelerated viral inhibition assay using neuraminidase activity (NA) as a read-out (Hassantoufighi, A. et al. 2010, Vaccine 28:790). Briefly, MNA were performed on MDCK cells that were cultured in MEM medium (Invitrogen) supplemented with antibiotics, glutamine (complete MEM medium) and 10% (v/v) fetal bovine serum. 60 $TCID_{50}$ (50% tissue culture infectious doses) of virus was added to three-fold dilutions of antibody in a 384-well plate in complete MEM medium containing 0.75 ug/ml Trypsin (Worthington) in duplicate wells, after 30 minutes incubation at room temperature, $2 \times 10^4$ cells/well were added to the plate. After incubation at 33° C. 5% $CO_2$ incubator for approximately 40 hr, the NA activity was measured by adding a fluorescently-labeled substrate, methylumbelliferyl-N-acetyl neuraminic acid (MU-NANA) (Sigma) to each well and incubated at 37° C. for 1 hr. Virus replication represented by NA activity was quantified by reading fluorescence in Fluorometer Envison (PerkinElmer) using the following settings: excitation 355 nm, emission 460 nm; 10 flashes per well. The neutralization titer (50% inhibitory concentration [$IC_{50}$]) is expressed as the final antibody concentration that reduced the fluorescence signal by 50% compared to cell control wells. Table 4 and 5 showed anti-HA antibodies neutralized influenza A viruses of different subtypes tested below: H1-PR34 (A/Puerto Rico/8/34 (H1N1)); H1-PR34-OR (A/Puerto Rico/8/34 containing the NA 274Y (N2 numbering) mutation confering oseltamivir resistance (H1N1)); H1-FM47 (A/Fort Monmouth/1/47 (H1N1)); H1-NJ76 (A/New Jersey/8/76 (H1N1)); H1-Kaw86 (A/Kawasaki/9/86 (H1N1)); H1-TX91 (caA/Texas/36/91 (H1N1)): H1-BJ95 (ca A/Beijing/262/95 (H1N1)); H1-Ncal99 (ca A/New Caledonia/20/99 (H1N1)); H1-SD07 (ca A/South Dakota/6/07 (H1N1)); H1-CA09 (ca A/California/7/09 (H1N1)); H1-CA09-OR (ca A/California/7/09 containing the NA 274Y (N2 numbering) mutation confering oseltamivir resistance (H1N1)); H5-VN04 (ca A/Vietnam/1203/04 (H5N1)); H5-HK03 (ca A/Hong Kong/213/03 (H5N1)); H9-HK97 (ca A/chicken/Hong Kong/G9/97 (H9N2); H2-JP57 (ca A/Japan/57 (H2N2)); H2-M006 (ca A/swine/Missouri/06 (H2N3)); H6-HK97 (ca A/teal/Hong Kong/W312/97 (H6N1)); H6-AB85 (ca A/mallard/Alberta/89/85 (H6N2)); H3-HK68 (A/Hong Kong/8/68 (H3N2)); H3-Vic75 (A/Victoria/3/75 (H3N2)); H3-LA87 (A/Los Angeles/7/09 (H3N2)); H3-SD93 (A/Shan dong/9/93 (H3N2)); H3-WH95 (ca A/Wuhan/359/95 (H3N2)); H3-Syd97 (ca A/Sydney/5/97 (H3N2)); H3-WH95-OR (ca A/Wuhan/359/95 containing the NA 274Y (N2 numbering) mutation confering oseltamivir resistance (H3N2)); H3-Pa99 (ca A/Panama/2007/99 (H3N2)); H3-Wy03 (A/Wyoming/03/03 (H3N2)); H3-WI05 (A/Wisconsin/67/05 (H3N2)); H3-Perth09 (ca A/Perth/16/09 (H3N2)), H3-VC11 (A/Victoria/361/11 (H3N2)); H7-NLD03 (ca A/Netherlands/219/03 (H7N7)); H7-BC04 (ca A/Brit. Columbia/CN-6/04 (H7N3-LP); H7-ANU13 (ca A/Anhui/1/13 (H7N9).

TABLE 4

| | Virus | Neutralization of infectious viruses ($IC_{50}$ ug/ml) Anti-body 3 | Anti-body 5 | Anti-body 6 | Anti-body 8 | Anti-body 10 |
|---|---|---|---|---|---|---|
| Group 1 | H1-PR34 | 1.07 | 1.13 | 4.37 | 3.02 | 2.15 |
| | H1-FM47 | 0.92 | 0.86 | 3.04 | 1.37 | 1.11 |
| | H1-NJ76 | 1.41 | 1.64 | 2.60 | 2.26 | 0.15 |
| | H1-Kaw86 | 0.58 | 1.01 | 3.51 | 2.11 | 1.62 |
| | H1-TX91 | 0.60 | 0.76 | 2.20 | 0.70 | 0.48 |
| | H1-BJ95 | 3.41 | 5.06 | 20.86 | 10.60 | 4.46 |
| | H1-Ncal99 | 0.79 | 0.85 | 3.00 | 2.06 | 1.26 |
| | H1-SD07 | 0.97 | 1.61 | 6.27 | 2.62 | 1.37 |
| | H1-CA09 | 2.19 | 2.52 | 5.56 | 4.50 | 1.62 |
| | H2-MO06 | 2.27 | 2.38 | 2.90 | 2.62 | 1.04 |
| | H5-VM04 | 2.11 | 2.60 | 8.87 | 3.90 | 2.21 |
| | H5-HK03 | 4.64 | 1.18 | 10.45 | 1.82 | 1.60 |
| | H6-HK97 | 1.77 | 2.27 | 3.23 | 2.97 | 1.05 |
| | H9-HK97 | 1.79 | 2.43 | 16.47 | 26.39 | 1.76 |
| Group 2 | H3-HK68 | 0.68 | 0.39 | 2.04 | 2.82 | 0.85 |
| | H3-Vic75 | 0.75 | 0.57 | 1.09 | 3.83 | 0.91 |
| | H3-LA87 | 4.19 | 3.54 | 12.60 | >50 | 4.59 |
| | H3-SD93 | 9.39 | 6.92 | 19.50 | >50 | 11.65 |
| | H3-WH95 | 3.96 | 3.72 | 10.54 | >50 | 8.70 |
| | H3-Syd97 | 3.75 | 3.03 | 6.54 | >50 | 9.29 |
| | H3-Pa99 | 17.74 | 16.74 | 25.82 | >50 | 18.71 |
| | H3-Wy03 | 0.63 | 0.77 | 4.70 | >50 | 1.52 |
| | H3-WI05 | 2.44 | 2.83 | 6.76 | >50 | 4.46 |
| | H3-Perth09 | 1.49 | 2.22 | 5.03 | >50 | 2.56 |
| | H7-NLD03 | 4.78 | 4.14 | >50 | 12.75 | 3.80 |
| | H7-BC04 | 4.72 | 5.35 | >50 | 14.69 | 3.59 |

Table 4 shows that anti-HA antibodies neutralize all group 1 influenza A viruses tested. All anti-HA antibodies except Antibody 8 demonstrated neutralizing activity against all H3 influenza A viruses tested and all anti-HA antibodies except Antibody 6 exhibited neutralizing activity against H7-NLD03 (ca A/Netherlands/219/03 (H7N7)); H7-BC04 (ca A/Brit. Columbia/CN-6/04 (H7N3-LP).

TABLE 5

| | Virus | Neutralization of infectious viruses ($IC_{50}$ ug/ml) Antibody 3 | Antibody 11 | Antibody 12 | Antibody 13 | Antibody 14 | Antibody 15 |
|---|---|---|---|---|---|---|---|
| Group 1 | H1-PR34 | 2.17 | 0.88 | 1.07 | 1.30 | 1.25 | 1.47 |
| | H1-PR34-OR | 1.39 | 0.73 | 0.69 | 0.88 | 0.83 | 0.90 |
| | H1-FM47 | 1.04 | 0.43 | 0.28 | 0.50 | 0.44 | 0.35 |
| | H1-NJ76 | 0.57 | 0.13 | 0.12 | 0.12 | 0.11 | 0.25 |
| | H1-Kaw86 | 1.01 | 0.53 | 0.28 | 0.41 | 0.35 | 0.48 |
| | H1-TX91 | 0.92 | 0.11 | 0.12 | 0.09 | 0.09 | 0.13 |
| | H1-BJ95 | 2.98 | 1.01 | 1.31 | 1.86 | 2.09 | 1.81 |
| | H1-Ncal99 | 1.16 | 0.66 | 0.61 | 0.77 | 0.67 | 0.79 |
| | H1-SD07 | 2.04 | 0.98 | 0.78 | 1.35 | 1.05 | 0.81 |
| | H1-CA09 | 2.07 | 0.90 | 0.98 | 1.23 | 1.07 | 1.17 |
| | H1-CA09-OR | 2.10 | 0.87 | 0.84 | 1.05 | 1.23 | 1.35 |
| | H1-BS10 | 2.16 | 1.15 | 1.25 | 1.23 | 1.93 | 1.89 |
| | H2-JP57 | 0.46 | 0.31 | 0.35 | 0.47 | 0.67 | 0.33 |
| | H2-MO06 | 1.09 | 0.60 | 0.53 | 0.57 | 0.65 | 0.83 |
| | H5-VM04 | 1.19 | 0.57 | 0.31 | 0.56 | 0.33 | 0.28 |

TABLE 5-continued

| | Virus | Antibody 3 | Antibody 11 | Antibody 12 | Antibody 13 | Antibody 14 | Antibody 15 |
|---|---|---|---|---|---|---|---|
| | Neutralization of infectious viruses (IC$_{50}$ ug/ml) | | | | | | |
| | H5-HK03 | 0.71 | 0.21 | 0.17 | 0.17 | 0.21 | 0.05 |
| | H6-AB85 | 0.69 | 0.24 | 0.32 | 0.29 | 0.26 | 0.19 |
| | H6-HK97 | 0.63 | 0.40 | 0.45 | 0.55 | 0.26 | 0.33 |
| | H9-HK97 | 1.18 | 0.36 | 0.31 | 0.29 | 0.44 | 0.35 |
| Group 2 | H3-HK68 | 1.37 | 0.46 | 0.42 | 0.44 | 0.65 | 0.50 |
| | H3-Vic75 | 1.12 | 0.46 | 0.32 | 0.43 | 0.44 | 0.35 |
| | H3-LA87 | 2.04 | 0.80 | 0.82 | 1.00 | 0.83 | 0.83 |
| | H3-SD93 | 3.57 | 1.11 | 1.32 | 1.56 | 1.57 | 1.43 |
| | H3-WH95 | 5.63 | 2.45 | 2.09 | 2.77 | 2.77 | 3.32 |
| | H3-WH95-OR | 7.70 | 2.26 | 2.34 | 3.01 | 3.09 | 3.48 |
| | H3-Syd97 | 6.50 | 1.53 | 1.56 | 2.18 | 1.82 | 1.79 |
| | H3-Pa99 | 9.00 | 2.18 | 2.04 | 2.62 | 4.36 | 3.39 |
| | H3-WI05 | 2.62 | 1.07 | 1.09 | 1.19 | 1.19 | 1.30 |
| | H3-Perth09 | 1.30 | 0.17 | 0.25 | 0.28 | 0.47 | 0.50 |
| | H3-VC11 | 3.40 | 0.85 | 0.83 | 1.03 | 1.15 | 1.29 |
| | H7-NLD03 | 4.74 | 0.94 | 0.83 | 2.45 | 1.16 | 1.30 |
| | H7-BC04 | 2.95 | 0.71 | 0.78 | 0.96 | 0.86 | 1.25 |
| | H7-ANU13 | 4.26 | nd | 2.56 | nd | 2.12 | nd |

Table 5 shows that the Antibody variants (Antibodies 11-15) are more effective than parental Antibody 3 in neutralizing all group 1 and group 2 influenza A viruses tested with decreased $IC_{50}$ values. In addition, antibodies also neutralized 3 viruses which have a mutation engineered into the NA protein conferring oseltamivir resistance (OR).

Example 5. Neutralizing Activity of Anti-HA IgGs Against Swine Origin H3N2 Viruses The neutralizing activity of anti-HA Antibody 3 and variants (Antibodies 11-15) against newly emerged swine-origin H3N2 viruses (A/Minnesota/11/2010 and A/Indiana/10/2011) was measured in a microneutralization assay as described in Example 4. Antibody Fl6v4 (described in WO2013/011347A1) was used as a control antibody. As shown in Table 6 from two independent experiments, Antibody 3 and the antibody variants (Antibodies 11-15) were more effective than Fl6v4 in neutralizing swine-origin A/Indiana/10/2011 H3N2 virus. Antibody 3 and the antibody variants potently neutralized swine-origin A/Minnesota/11/2010 H3N2 virus whereas Fl6v4 failed to neutralize at the highest concentration (50 ug/ml) of antibody tested.

TABLE 6

| H3N2 virus | Neutralizing activity ($IC_{50}$ ug/ml) FI6 v4 | Antibody 3 | Antibody 11 | Antibody 12 | Antibody 13 | Antibody 14 | Antibody 15 |
|---|---|---|---|---|---|---|---|
| swine-origin | >50 | 2.2 | 1.6 | 1.1 | 1.6 | 1.4 | 0.9 |
| A/Minnesota/ 11/2010 | >50 | 4.2 | 1.5 | 1.2 | 1.4 | 2.3 | 2.7 |
| swine-origin | 13.7 | 3.1 | 2.8 | 2.5 | 2.2 | 3.3 | 5.5 |
| A/Indiana/ 10/2011 | 29.3 | 3.7 | 2.1 | 1.8 | 3.9 | 2.9 | 3.9 |

Example 6. Anti-HA Neutralizing Antibody Inhibits Influenza Fusion and Protease-Mediated HA0 Cleavage To test for the antibody mediated fusion inhibition, a low pH induced red blood cell fusion assay was performed through a modified protocol described previously (Wang T. T. et al., 2010 PLoS Pathog. 6). In brief, A/Puerto Rico/8/34 virus ($10\times10^6$ TCID50) was incubated with human red blood cells (2% final red cell concentration) on ice for 10 minutes. Dilutions of Antibody 3, Antibody 12, and a non-relevant antibody MPE8v3 were incubated with virus for 30 minutes at RT. The red blood cells were then added to the virus-antibody mixture for 30 minutes at 37° C. and finally sodium acetate buffer (0.5 M pH 5.0) was added for additional 45 minutes at 37° C. Samples were centrifuged for 6 minutes at 400×g and incubated for additional 45 minutes at RT and then centrifuged again for 6 minutes at 400×g to pellet red blood cells. Supernatants were then transferred to an ELISA plate to determine the amount of released NADPH by measuring absorbance at 540 nm (FIG. 1B). The result showed that Antibody 3 and Antibody 12 potently inhibited viral fusion whereas the MPE8v3, a human monoclonal antibody against the fusion protein of a paramyxovirus (Corti et al., 2013 Nature 501), was not able to inhibit the low pH induced fusion.

To test for antibody mediated blockade of the HA maturation, recombinant HA of A/New Caledonia/20/99 (H1N1) was incubated for 40 minutes with Antibody 3, Fl6v4, FE17.23 or an isotope control antibody at molar ratio of 15:1 (mAb:HA). The antibody-HA mixture was then exposed to 2.5 ug/ml of TPCK-treated trypsin and incubated for 5, 10 and 20 minutes at 37° C. The samples were separated on a polyacrylamide gel and then transferred to nitrocellulose membrane for Western blot analysis using a biotinylated human mAb (F032) (Humabs) that recognizes HA2 and HA0 of influenza A strains (FIG. 1C). The result showed that Antibody 3 was more potent than Fl6v4 in blocking the protease-mediated HA0 cleavage. In contrast, FE17.23, a human monoclonal antibody that recognizes the HA globular head and control antibody were not able to inhibit protease-mediated HA0 cleavage. In a separate experiment we compared the protease cleavage inhibition of Antibody 12 and Antibody 14 in comparison to Antibody 3 using the same conditions described above (FIG. 1D). The results showed that Antibody 12, Antibody 13, had a similar ability to block the protease cleavage as Antibody 3.

Example 7. Anti-HA Antibodies Exhibit Fc-Effector Function

Antibodies have the potential to clear virus infected cells through Fc-effector function such as antibody dependent cellular cytotoxicity (ADCC), antibody dependent cellular phagocytosis (ADCP), and complement dependent killing (CDC). To confirm the anti-HA antibodies exhibited ADCC activity; we tested their ability to kill virus infected cells in the presence of human natural killer (NK) cells. The ADCC assay was performed on MDCK cells infected with A/Hong Kong/8/68 at an MOI of 20. Infected cells were incubated with a dilution series of antibody, and then incubated with purified NK cells that were negatively selected from human PBMC (Miltenyi), at an effector to target ratio of 6:1. The infected cells, antibody, and NK cells mixtures were incubated for 4 hours, and cell killing was measured by LDH release (Roche). FIG. 2 shows that all four anti-HA stalk antibodies exhibited dose dependent killing of infected MDCK cells.

To measure the ability of the anti-HA antibodies to mediate phagocytosis, we used MDCK cells stably transfected with the HA derived from A/Hong Kong/8/68 as target cells. Human monocytes were isolated from PBMCs, and cultured for 7 days in the presence of M-CSF to differentiate into macrophages. The human macrophages and HA-expressing target cells were fluorescently labelled violet and green, respectively (CellTrace Violet or CSFE, Invitrogen). Labelled effector and target cells were incubated at a 6:1 ratio in the presence of a dilution series of antibody for 2 hours, and then analyzed by flow cytometry. The percent phagocytosis was measured as the percent of violet stained macrophages that also were positive for the green target cells (double positive). FIG. 3 shows that all the anti-HA antibodies showed similar levels of ADCP, as expected the nonspecific control antibody showed no phagocytosis.

To measure the ability of the anti-HA antibodies to work with complement to mediate the killing of infected cells, we performed CDC assay. In this this assay, MDCK cells were infected with A/Puerto Rico/8/34 at an MOI of 2, incubated with a dilution series of antibody, and complement derived from a rabbit (Cedarlane) at an effector to target ratio of 1:18. Cell killing was measured by LDH release (Roche). FIG. 4 shows that all the anti-HA antibodies showed the ability to mediate cell killing in the presence of complement.

Example 8. Prophylactic and Therapeutic Effect of Anti-HA Antibodies

The protective efficacy of human neutralizing antibody (nAbs) against influenza virus infection was evaluated in six-to-eight weeks' old BALB/c (Harlan Laboratories) mouse model. Mice were treated with different doses of nAb either before or after lethal viral challenge.

Prophylactic activity (FIGS. 5 & 6) Mice in groups of 8 were administered with Antibody 3 as a single intraperitoneal injection (IP) at doses of 0.1, 0.3, 1, 3 and 10 mg/kg, or with a human isotype non-relevant control IgG at 10 mg/kg in 100 µl volumes. Four hours after dosing, mice were inoculated intranasally with 7 times the fifty percent mouse lethal dose (7 $MLD_{50}$) of A/California/7/09 (H1N1) (H1-CA09) or 7:1 A/PR/8:A/HK/8/68 HA (H3N1) (H3-HK68) reassortant in a 50 µl volume. Mice were weighed on the day or one day before virus challenge and monitored daily for 14 days for weight loss and survival (mice with body weight loss 25% were euthanized). Antibody 3 conferred protection in a dose-dependent manner. IP injection of 1 mg/kg or greater of Antibody 3 provided complete protection in animals challenged with H1-CA09 (FIG. 5) and H3-HK68 (FIG. 6). A lower antibody dose (0.3 mg/kg) was also highly protective with 90% protection. As expected, none of the mice that received the isotype control mAb at 10 mg/kg survived lethal challenge of infection.

Therapeutic activity (FIGS. 7 & 8) Mice were inoculated with 3 $MLD_{50}$ of H1-CA09 and injected with Antibody 3 at 24 and 48 hours post infection (h.p.i.) (FIG. 7) or with 5 $MLD_{50}$ of H3-HK68 at 72, 96 and 120 h.p.i. (FIG. 8). IP treatment with 30 mg/kg of Antibody 3 at 24 and 48 h.p.i protected 75-100% of mice challenged with H1-CA09, and at 72 and 96h.p.i protected 87.5-100% of mice challenged with H3-HK68. Treatment with same dose of non-relevant isotype control antibody at 0 or 24 h.p.i in H1 and H3 models failed to protect mice from lethal challenge with a survival rate of 0 or 12.5%, respectively.

Therapeutic activity of Antibody 3 variants (FIGS. 9 & 10) Mice were inoculated with 3 $MLD_{50}$ of H1-CA09 and injected with antibodies 24 h.p.i. (FIG. 9) or inoculated with 7 $MLD_{50}$ H3-HK68 and injected with antibodies 48 h.p.i. (FIG. 10). IP treatment with 2 mg/kg of Antibody 3 and variant mAbs (Antibody 11, Antibody 12, and Antibody 14) protected 87.5-100% of mice challenged with H1-CA09, and 3 mg/kg dose of the different nAbs protected 50-87.5% of mice challenged with H3-HK68 As expected, treatment with same dose of non-relevant isotype control antibody at 24 or 48 h.p.i in H1 and H3 models failed to protect mice with a survival rate of 0 or 12.5%, respectively.

Example 9. Therapeutic Effect of Anti-HA Antibodies and Small Molecule Inhibitor Oseltamivir To directly compare the protective efficacy of anti-HA nAbs to small molecule neuraminidase (NA) inhibitor, oseltamivir, and the effect of combination therapy, we used the influenza murine model of infection described in Example 8.

Therapeutic comparison of anti-HA nAbs and oseltamivir (FIGS. 11 & 12) Mice were inoculated with 3 $MLD_{50}$ of H1-CA09 and treated with 10 mg/kg of Antibody 12 or 25 mg/kg BID for 5 days of oseltamivir initiated either at 4 hrs prior, 1 day, or 2 days post infection (FIG. 11). Treatment with Antibody 12 prior to and 1 day post infection protected 100% of mice challenged with H1-CA09, whereas all animals treated with oseltamivir succumbed to the infection. All animals treated with the same dose of non-relevant isotype control 4 hours prior to infection died with a survival rate of 0%. Additionally, mice were inoculated with 7 $MLD_{50}$ of H3-HK68 then treated with 10 mg/kg of Antibody 12 or 25 mg/kg BID for 5 days of oseltamivir initiated either at 1, 2, 3, or 4 days post infection (FIG. 12). Animals treated with Antibody 12 at 1, 2, or 3 days post infection showed a survival rate of 100%, whereas treatment with oseltamivir at these same time points showed only a 60%-20% survival rate. As expected, mice treated with same dose of non-relevant isotype control antibody 1 day post infection succumbed to the infection with a survival rate of 10%.

Therapeutic combination of anti-HA nAbs and oseltamivir (FIG. 13) To assess the additive effect of the combination of anti-HA mAb with oseltamivir, mice were inoculated with 7 $MLD_{50}$ of H3-HK68 and treated with a suboptimal concentration of Antibody 12 (2.5 or 0.3 mg/kg), oseltamivir at 25 mg/kg BID for 5 days, or a combination of Antibody 12 (2.5 or 0.3 mg/kg) and oseltamivir at 25 mg/kg BID for 5 days, at day 3 post infection (FIG. 13). Treatment with either Antibody 12 or oseltamivir alone protected only 10-20% of the animals whereas treatment with the 2.5 mg/kg of Antibody 12 in combination with oseltamivir protected 80%, and 0.3 mg/kg of Antibody 12 in combination with oseltamivir protected 50% of the animals.

Example 10. Therapeutic Effect of Anti-HA Antibodies and Small Molecule Inhibitor Against H5N1 Influenza Infection in the Ferret The protective efficacy of anti-HA nAbs and oseltamivir against a highly pathogenic influenza virus infection was evaluated in five-to-six months' old influenza sero-negative ferrets (Triple F Farms). All ferrets were challenged intranasally with 1 $LD_{90}$ of ANN/1203/04 (H5N1) highly pathogenic avian influenza virus in 1.0 mL (approximately 0.5 mL/nare), and then treated with either a single dose of Antibody 12 at 25 mg/kg or oseltamivir at 25 mg/kg BID for 5 days initiated at 1, 2, or 3 days post infection. Percent survival was calculated for each group (n=7) (FIG. 14). Ferrets treated with Antibody 12 initiated at 1, 2, and 3 days post infection, as well as those treated with oseltamivir 1 day post infection were protected, having a 100% survival rate. However, when oseltamivir treatment was initiated at 2 and 3 days post infection, ferrets only had 71% survival (mean day of death of 12) and 29% survival (mean day of death 9), respectively. As expected animals treated with 25 mg/kg of a non-relevant isotype control antibody at 1 day post infection failed to live with a 0% survival rate.

Example 11. Epitope Identification by Selection of Monoclonal Antibody Resistant Mutants (MARMs)

Antibody resistant mutants were isolated using two different methods from three H3N2 viruses. A/Aichi/2/68 (Aichi/68) H3N2 was incubated with high concentrations of Antibody 12 ($125 \times IC_{50}$) for 1 hour before the mixture of virus and antibody was adsorbed to MDCK cells at 30,000 TCID50 per well in 10×96-well plates and cultured in the presence of Antibody 12 ($10 \times IC_{50}$). 3 putative Antibody 12 HK2/68 MARMs exhibiting the cytopathic effect (CPE) on the infected cells up to 3 days after infection were isolated. The HA gene were amplified by RT-PCR and subsequently sequenced. Sequence analysis revealed 2 nonsynonymous substitutions compared with the parental sequence (Table 7). These two nucleotide changes respectively code for single amino acid substitutions from isoleucine (I) to arginine (R); and from aspartic acid (D) to tyrosine (Y) at amino acid position 18 and 19 in the highly conserved stalk region of HA2. Alternatively, serial passage of influenza H3N2 viruses, A/Wisconsin/67/2005 (W105), and ca A/Panama/2007/1999 (Pa99) were propagated in the presence of increasing concentrations of Antibody 12 from $2-5 \times IC_{50}$ up to $100 \times IC_{50}$. Potential escape mutants were subcloned by limited dilution and their cognate HA genes were subjected to sequence analysis. The single amino acid changes from D to Y at position 19 and from Glutamine(Q) to R at position 42 in HA2 was identified. In addition, double mutations were observed with amino acid substitution from Histine (H) to Q at position 156 in HA1 in combination with D19Y, or from D to asparagine (N) at position 19 in combination with amino acid change from 1 to N at residue 45 in HA2; or from alanine (A) to threonine (T) at position 196 in HA1 in combination with Q42R (Table 7). Similarly, when Pa99 was serially passaged in the presence of Antibody 12 concentrations up to $100 \times IC_{50}$, single amino acid substitution was selected at HA2 residue 42 (Q42R) and 45 (I45T) (Table 7). The representative MARM variants shown in Table 7 were used in a microneutralization assay to further evaluate the phenotypic susceptibility of these MARMs to neutralization by Antibody 12. The results showed that the in vitro-selected W105 MARMs containing mutations D19Y, H156Q/D19Y, D19N/I45N, Q42R or A196T/Q42R; Pa99 MARMs containing Q42R or I45T, and Aichi/68 MARMs harboring mutations D19Y or I18R were less susceptible to antibody neutralization, with increases in calculated $IC_{50}$ values ranging from >8-fold for Pa99 resistant clones to >180-fold for W105 resistant variants when compared with their parental wild type strains, respectively (Table 8). To assess the effect of these amino acid substitutions on the susceptibility to neutralization by Antibody 12, recombinant A/Hong Kong/1-5/68 (rHK68) H3 variants encoding individual mutations were generated and evaluated using a microneutralization assay. As shown in Table 9, the H3 rHK68_I18R and rHK68_D19Y variants exhibited resistance to Antibody 12 at the highest concentration tested (~200 µg/mL) and conferred >130-fold reduction in susceptibility to Antibody 12 neutralization compared with wild type rHK68 virus. The single amino acid changes Q42R in rHK68 resulted in modest about 8-fold reductions in susceptibility to neutralization by Antibody 12. However, amino acid substitutions (K156Q, A196T, I45N or I45T) identified in the HA proteins of selected MARMs did not alter the susceptibility of recombinant HK68 viruses encoding such substitutions to Antibody 12 in microneutralization assay. These results suggest that Antibody 12 recognizes conformational epitopes in a highly conserved stalk region of HA2 and amino acids at positions 18, 19 42 or 45 are key contact residues.

TABLE 7

Amino acid substitutions identified in the H3 HA of Antibody 12 resistant mutants

| H3N2 Virus | Nucleotide change | Amino acid change in HA | Location in HA subunits |
|---|---|---|---|
| A/Wisconsin/67/2005 | G1090T | D19Y | HA2 |
|  | C156A, G1090T | H156Q, D19Y | HA1, HA2 |
|  | A1160G | Q42R | HA2 |
|  | G634A, A1160G | A196T, Q42R | HA1 ,HA2 |
|  | G1090A, T1169A | D19N, I45N | HA2, HA2 |
| ca A/Panama/2007/99 | A1160G | Q42R | HA2 |
|  | T1169C | I45T | HA2 |
| A/Aichi/2/68 | G1090T | D19Y | HA2 |
|  | T1088G | I18R | HA2 |

TABLE 8

Susceptibility of H3 resistant variants to Antibody 12 neutralization (Neut)

| Parental H3N2 virus | Amino acid changes in HA of MARMs tested | Avg. Neut. (µg/ml) | Fold changes relative to wild type virus |
|---|---|---|---|
| A/Wisconsin/67/2005 | wild type | 1.09 | |
| | D19Y | >200 | >180 |
| | Q42R | >200 | >180 |
| | H156Q/D19Y | >200 | >180 |
| | D19N/I45N | >200 | >180 |
| | A196T/Q42R | >200 | >180 |
| ca A/Panama/2007/99 | wild type | 6.68 | |
| | Q42R | >600 | >90 |
| | I45T | 54.51 | 8.16 |
| A/Aichi/2/68 | wild type | 3.98 | |
| | D19Y | >50 | >12 |
| | I18R | >50 | >12 |

TABLE 9

Susceptibility of rHK68 H3 variants to Antibody 12 Neutralization (Neut)

| reassortant virus_mutation | Avg. Neut. (µg/ml) | Fold changes relative to wild type virus |
|---|---|---|
| rHK68 wild type | 1.42 | 1 |
| rHK68_H8R | >200 | >130 |
| rHK68_D19N | 3.04 | 2.01 |
| rHK68_D19Y | >200 | >130 |
| rHK68_Q42R | 11.13 | 7.82 |
| rHK68_I45N | 1.94 | 1.28 |
| rHK68_I45T | 3.38 | 2.23 |
| rHK68_K156Q | 3.33 | 2.34 |
| rHK68_A196T | 4.06 | 2.85 |

INFLUENZA A REFERENCES

Corti, D., et al. 2010. Heterosubtypic neutralizing antibodies are produced by individuals immunized with a seasonal influenza vaccine. J Clin Invest 120:1663-1673.

Corti, D., et al. 2011. A neutralizing antibody selected from plasma cells that binds to group 1 and group 2 influenza A hemagglutinins. Science 333:850-856.

Corti D., et al. 2013. Cross-neutralization of four paramyxoviruses by a human monoclonal antibody. Nature 501 (7467):439-43.

Ekiert, D. C. et al. 2009. Antibody recognition of a highly conserved influenza virus epitope. Science 324: 246-251.

Ekiert, D. C. et al 0.2011. A highly conserved neutralizing epitope on group 2 influenza A viruses. Science 333:843-850.

Ekiert, D. C., et al. 2012. Cross-neutralization of influenza A viruses mediated by a single antibody loop. Nature 489: 526-532.

Krause, J. C., et al. 2011. A broadly Neutralizing human monoclonal antibody that recognizes a conserved, novel epitope on the globular head of the influenza H1N1 virus hemagglutinin. J. Virol. 85:10905-10908.

Lee, P. S., et al. 2012. Heterosubtypic antibody recognition of the influenza virus hemagglutinin receptor binding site enhanced by avidity. Proc Natl Acad Sci USA. 109: 17040-17045

Li G. M. et al 2012. Pandemic H1N1 influenza vaccine induces a recall response in humans that favors broadly cross-reactive memory B cells. Proc Natl Acad Sci USA. 109:9047-9052.

Nakamura G. et al 2013. An in vivo human-plasmablast enrichment technique allows rapid identification of therapeutic influenza a antibodies. Cell host microbe 14:93-103

Sui, J., et al. 2009. Structure and functional bases for broad-spectrum neutralization of avian and human influenza A viruses. Nat Struct Mol Biol 16: 265-273.

Throsby, M., et al. 2008. Heterosubtypic neutralizing monoclonal antibodies cross-protective against H5N1 and H1N1 recovered from human IgM+ memory B cells. PLoS One 3: e3492

Wang T. T., et al., 2010. Broadly protective monoclonal antibodies against H3 influenza viruses following sequential immunization with different hemagglutinins. PLoS Pathog. 6(2):e1000796.

Whittle, J. R. R., et al. 2011. Broadly neutralizing human antibody that recognizes the receptor-binding pocket of influenza virus hemagglutinin. Proc Natl Acad Sci USA. 108:14216-14221.

Wrammert, J., et al. 2011. Broadly cross-reactive antibodies dominate the human B cell response against 2009 pandemic H1N1 influenza virus infection. J Exp Med. 208: 181-193.

```
                        Sequence Listing Information

Antibody 1 (original cDNA)
SEQ ID NO: 1
cagatacagctgcaggagtcgggtccaggactggtgaagccctcgcagaccctctcactcacctgtgccat
ctccggggacagtgtctctagcaacaatgctgtttggaactggatcaggcagtccccatcgagaggccttga
gtggctgggaaggacatactacagtccaagtggtataatgattatgcagaatctgtgaaaagtcgaataa
ccgtcaatccagacacatccaagaaccagttctccctgcacctgaagtctgtgactcccgaggacacggct
gtgttttactgtgtacgatctggccacattacggttttttggagtgaatgttgacgcttttgatatgtggggccaagg
gacaatggtcaccgtctcttcag SEQ ID NO: 2
QIQLQESGPGLVKPSQTLSLTCAISGDSVSSNNAVWNWIRQSPSRGLEWLG
RTYYRSKWYNDYAESVKSRITVNPDTSKNQFSLHLKSVTPEDTAVFYCVRS
GHITVFGVNVDAFDMWGQGTMVTVSS

SEQ ID NO: 3 HCDR1 SNNAVWN

SEQ ID NO: 4 HCDR2 RTYYRSKWYNDYAESVKS

SEQ ID NO: 5 HCDR3 SGHITVFGVNVDAFDM

SEQ ID NO: 6
gacatccagatcacccagtcgccatcctccctgtctgcatctgtaggagacagagtaaccatcacttgccgg
```

| Sequence Listing Information |
|---|
| acaagtcagagccttagtagctatttacattggtatcagcagaaaccagggaaagcccctaagctcctgatc<br>tatgctgcatccagtttgcaaagtggggtcccatcaaggttcagtggcagtggatctgggacagatttcactct<br>caccatcagtagtctgcaacctgaagattttgcaacttactactgtcaacagagtcggacgttcggccaagg<br>gaccaaggtggaaatcaaa<br><br>SEQ ID NO: 7<br>DIQITQSPSSLSASVGDRVTITCRTSQSLSSYLHWYQQKPGKAPKLLIYAASS<br>LQSGVPSRFSGSGSGTDFTLTISSLQPEDFATYYCQQSRTFGQGTKVEIK<br><br>SEQ ID NO: 8 LCDR1 RTSQSLSSYLH<br><br>SEQ ID NO: 9 LCDR2 AASSLQS<br><br>SEQ ID NO: 10 LCDR3 QQSRT<br><br>Antibody 2 (expressed form of Antibody 1)<br>SEQ ID NO: 11<br>caggtacagctgcaggagtcgggtccaggactggtgaagccctcgcagaccctctcactcacctgtgccat<br>ctccggggacagtgtctctagcaacaatgctgtttggaactggatcaggcagtcccatcgagaggccttga<br>gtggctgggaaggacatactacaggtccaagtggtataatgattatgcagaatctgtgaaaagtcgaataa<br>ccgtcaatccagacacatccaagaaccagttctccctgcacctgaagtctgtgactcccgaggacacggct<br>gtgttttactgtgtacgatctggccacattacggttttggagtgaatgttgacgcttttgatatgtggggccaagg<br>gacaatggtcaccgtctcttcag<br><br>SEQ ID NO: 12<br>QVQLQESGPGLVKPSQTLSLTCAISGDSVSSNNAVWNWIRQSPSRGLEWL<br>GRTYYRSKWYNDYAESVKSRITVNPDTSKNQFSLHLKSVTPEDTAVFYCVR<br>SGHITVFGVNVDAFDMWGQGTMVTVSS<br><br>SEQ ID NO: 13 HCDR1 SNNAVWN<br><br>SEQ ID NO: 14 HCDR2 RTYYRSKWYNDYAESVKS<br><br>SEQ ID NO: 15 HCDR3 SGHITVFGVNVDAFDM<br><br>SEQ ID NO: 16<br>gacatccagatgacccagtcgccatcctccctgtctgcatctgtaggagacagagtaaccatcacttgccgg<br>acaagtcagagccttagtagctatttacattggtatcagcagaaaccagggaaagcccctaagctcctgatc<br>tatgctgcatccagtttgcaaagtggggtcccatcaaggttcagtggcagtggatctgggacagatttcactct<br>caccatcagtagtctgcaacctgaagattttgcaacttactactgtcaacagagtcggacgttcggccaagg<br>gaccaaggtggaaatcaaa<br><br>SEQ ID NO: 17<br>DIQMTQSPSSLSASVGDRVTITCRTSQSLSSYLHWYQQKPGKAPKLLIYAAS<br>SLQSGVPSRFSGSGSGTDFTLTISSLQPEDFATYYCQQSRTFGQGTKVEIK<br><br>SEQ ID NO: 18 LCDR1 RTSQSLSSYLH<br><br>SEQ ID NO: 19 LCDR2 AASSLQS<br><br>SEQ ID NO: 20 LCDR3 QQSRT<br><br>Antibody 3 (codon optimized Antibody 2)<br>SEQ ID NO: 21<br>caggtccagctgcaggagagcggccccggactggtcaagccttcacagacactgagcctgacatgcgcc<br>attagcggagatagcgtgagctccaacaatgccgtgtggaactggatcaggcagtctccaagtcgaggac<br>tggagtggctgggacgaacatactatagatccaagtggtacaatgactatgctgaatcagtgaaaagccg<br>aattactgtcaaccccgatacctccaagaatcagttctctctgcacctgaaaagtgtgacccctgaggacac<br>agccgtgttctactgcgtcagaagcggccatatcaccgtctttggcgtcaatgtggatgctttcgatatgtggg<br>ggcaggggactatggtcaccgtgtcaagc<br><br>SEQ ID NO: 22<br>QVQLQESGPGLVKPSQTLSLTCAISGDSVSSNNAVWNWIRQSPSRGLEWL<br>GRTYYRSKWYNDYAESVKSRITVNPDTSKNQFSLHLKSVTPEDTAVFYCVR<br>SGHITVFGVNVDAFDMWGQGTMVTVSS<br><br>SEQ ID NO: 23 HCDR1 SNNAVWN<br><br>SEQ ID NO: 24 HCDR2 RTYYRSKWYNDYAESVKS<br><br>SEQ ID NO: 25 HCDR3 SGHITVFGVNVDAFDM<br><br>SEQ ID NO: 26<br>gatattcagatgacccagagcccttccagcctgtccgcttcagtgggggatcgagtgaccattacctgccga<br>accagccagagcctgagctcctacctgcactggtatcagcagaagcccggcaaagcccctaagctgctg<br>atctacgccgcttcagtctgcagtccggagtgccaagccggttctccggatctggagtggaaccgactttta<br>ccctgacaatttcaagcctgcagcccgaggatttcgctacatactactgtcagcagagcagaacttcgggc | agggcactaaggtggagatcaaa

SEQ ID NO: 27
DIQMTQSPSSLSASVGDRVTITCRTSQSLSSYLHWYQQKPGKAPKLLIYAAS
SLQSGVPSRFSGSGSGTDFTLTISSLQPEDFATYYCQQSRTFGQGTKVEIK

SEQ ID NO: 28 LCDR1 RTSQSLSSYLH

SEQ ID NO: 29 LCDR2 AASSLQS

SEQ ID NO: 30 LCDR3 QQSRT

Antibody 4 (original cDNA) degenerate nucleotide in HCDR3, t or a
SEQ ID NO: 31
caggtccagctgcagcagtcaggtccaggactggtgaagccctcgcagaccctctcactcacctgtgccat
ctccggggacagagtctctagcaacagtgctgtttggaactggatcaggcagtcccatcgagaggcctcg
agtggctgggaaggacatattacaggtccaaatggtattatgattatgcagaatctgtgaaaagtcgaatagt
tatcgacccagacacatccaagaaccaggtctccctgcagttgaattctgtgactcccgaggactcggctat
atattactgtgcaagaggtggccacattacggtgtttgggctgaatattgacgcttatgatatttggggccaag
gggcaaaggtcaccgtgtcttcag SEQ ID NO: 32
QVQLQQSGPGLVKPSQTLSLTCAISGDRVSSNSAVWNWIRQSPSRGLEWL
GRTYYRSKWYYDYAESVKSRIVIDPDTSKNQVSLQLNSVTPEDSAIYYCARG
GHITVFGLNIDAYDIWGQGAKVTVSS

SEQ ID NO: 33 HCDR1 SNSAVWN

SEQ ID NO: 34 HCDR2 RTYYRSKWYYDYAESVKS

SEQ ID NO: 35 HCDR3 GGHITVFGLNIDAYDI

SEQ ID NO: 36
gacatccaggtgacccagtctccgtcctccctgtctgcatctgtaggagacagagtcaccatctcttgccggg
cacagagccttagcagctacttacattggtatcagcagaaaccagggcaaccccctaaactcctgatctat
gctgcaaccactttgcaaagtggggtcccatcacggttcagtggtagtggatctgggacagatttcactctca
ccatcagtactttccaagctgaagatgttgccacttactattgtcaacgagtcggacgttcggccaagggac
caaggttgaaatcaaac SEQ ID NO: 37
DIQVTQSPSSLSASVGDRVTISCRAQSLSSYLHWYQQKPGQPPKLLIYAATT
LQSGVPSRFSGSGSGTDFTLTISTFQAEDVATYYCQQSRTFGQGTKVEIK

SEQ ID NO: 38 LCDR1 RAQSLSSYLH

SEQ ID NO: 39 LCDR2 AATTLQS

SEQ ID NO: 40 LCDR3 QQSRT

Antibody 5 (expressed form of Antibody 4 HCDR3 V)
SEQ ID NO: 41
caggtacagctgcagcagtcaggtccaggactggtgaagccctcgcagaccctctcactcacctgtgccat
ctccggggacagagtctctagcaacagtgctgtttggaactggatcaggcagtcccatcgagaggcctcg
agtggctgggaaggacatattacaggtccaaatggtattatgattatgcagaatctgtgaaaagtcgaatagt
tatcgacccagacacatccaagaaccaggtctccctgcagttgaattctgtgactcccgaggactcggctat
atattactgtgcaagaggtggccacattacggtgtttgggctgaatattgacgcttatgatatttggggccaag
gggcaatggtcaccgtctcttcag SEQ ID NO: 42
QVQLQQSGPGLVKPSQTLSLTCAISGDRVSSNSAVWNWIRQSPSRGLEWL
GRTYYRSKWYYDYAESVKSRIVIDPDTSKNQVSLQLNSVTPEDSAIYYCARG
GHITVFGLNIDAYDIWGQGAMVTVSS

SEQ ID NO: 43 HCDR1 SNSAVWN

SEQ ID NO: 44 HCDR2 RTYYRSKWYYDYAESVKS

SEQ ID NO: 45 HCDR3 GGHITVFGLNIDAYDI

SEQ ID NO: 46
gacatccagatgacccagtctccgtcctccctgtctgcatctgtaggagacagagtcaccatctcttgccggg
cacagagccttagcagctacttacattggtatcagcagaaaccagggcaaccccctaaactcctgatctat
gctgcaaccactttgcaaagtggggtcccatcacggttcagtggtagtggatctgggacagatttcactctca
ccatcagtactttccaagctgaagatgttgccacttactattgtcaacagagtcggacgttcggccaagggac
caaggtggagatcaaac

SEQ ID NO: 47

DIQMTQSPSSLSASVGDRVTISCRAQSLSSYLHWYQQKPGQPPKLLIYAATT
LQSGVPSRFSGSGSGTDFTLTISTFQAEDVATYYCQQSRTFGQGTKVEIK

SEQ ID NO: 48 LCDR1 RAQSLSSYLH

SEQ ID NO: 49 LCDR2 AATTLQS

SEQ ID NO: 50 LCDR3 QQSRT

Antibody 6 (expressed form of Antibody 4 HCDR3 E)
SEQ ID NO: 51
caggtacagctgcagcagtcaggtccaggactggtgaagccctcgcagaccctctcactcacctgtgccat
ctccggggacagagtctctagcaacagtgctgtttggaactggatcaggcagtcccatcgagaggcctcg
agtggctgggaaggacatattacaggtccaaatggtattatgattatgcagaatctgtgaaaagtcgaatagt
tatcgacccagacacatccaagaaccaggtctccctgcagttgaattctgtgactcccgaggactcggctat
atattactgtgcaagaggtggccacattacggagtttgggctgaatattgacgcttatgatatttggggccaag
gggcaatggtcaccgtctcttcag SEQ ID NO: 52
QVQLQQSGPGLVKPSQTLSLTCAISGDRVSSNSAVWNWIRQSPSRGLEWL
GRTYYRSKWYYDYAESVKSRIVIDPDTSKNQVSLQLNSVTPEDSAIYYCARG
GHITEFGLNIDAYDIWGQGAMVTVSS

SEQ ID NO: 53 HCDR1 SNSAVWN

SEQ ID NO: 54 HCDR2 RTYYRSKWYYDYAESVKS

SEQ ID NO: 55 HCDR3 GGHITEFGLNIDAYDI

SEQ ID NO: 56
gacatccagatgacccagtctccgtcctccctgtctgcatctgtaggagacagagtcaccatctcttgccggg
cacagagccttagcagctacttacattggtatcagcagaaaccagggcaaccccctaaactcctgatctat
gctgcaaccactttgcaaagtggggtcccatcacggttcagtggtagtggatctgggacagatttcactctca
ccatcagtactttccaagctgaagatgttgccacttactattgtcaacagagtcggacgttcggccaagggac
caaggtggagatcaaac SEQ ID NO: 57
DIQMTQSPSSLSASVGDRVTISCRAQSLSSYLHWYQQKPGQPPKLLIYAATT
LQSGVPSRFSGSGSGTDFTLTISTFQAEDVATYYCQQSRTFGQGTKVEIK

SEQ ID NO: 58 LCDR1 RAQSLSSYLH

SEQ ID NO: 59 LCDR2 AATTLQS

SEQ ID NO: 60 LCDR3 QQSRT

Antibody 7 (original cDNA)
SEQ ID NO: 61
caggtacagctgcagcagtcaggtccaggactggtgaagccctcgcagaccctctccctcacctgtgtcat
ctccggagacactgtctctagcaacagagctacttggaattggatgaggcagtcccattgagaggccttga
gtggctgggaaggacatactacaggtccaagtggtataatgattacgcagtttctgtgaaaagtcgagtagt
catcaacccagacacatccaagaaccaagtctccctgcagttgaacactgtgactcccgatgactcgggtg
tatacttttgtgcaagaggtggccacatcacggtctttggagtgaatattgacgcttttgacatctggggcctcg
ggacaaaggtcaccgtctcttcag SEQ ID NO: 62
QVQLQQSGPGLVKPSQTLSLTCVISGDTVSSNRATWNWMRQSPLRGLEWL
GRTYYRSKWYNDYAVSVKSRVVINPDTSKNQVSLQLNTVTPDDSGVYFCAR
GGHITVFGVNIDAFDIWGLGTKVTVSS

SEQ ID NO: 63 HCDR1 SNRATWN

SEQ ID NO: 64 HCDR2 RTYYRSKWYNDYAVSVKS

SEQ ID NO: 65 HCDR3 GGHITVFGVNIDAFDI

SEQ ID NO: 66
gacatccaggtgacccagtctccatcctccctgtctgcatctgtaggagacagagttaccatctcttgccggg
caagtcagagacttaatagttatctacattggtatcagcagacaccagggcaagcccgaagctgctgatct
atgcaacgtccactttgcaaagtggggtctcaccaagattcagtggcagtggatctgggacagatttcactct
caccatcagcagtctccaacctgaagatgttgcaacttactactgtcaattgagtcggacgttcggccacgg
gaccaaggttgaaatcaaac SEQ ID NO: 67
DIQVTQSPSSLSASVGDRVTISCRASQRLNSYLHWYQQTPGQAPKLLIYATS
TLQSGVSPRFSGSGSGTDFTLTISSLQPEDVATYYCQLSRTFGHGTKVEIK

| Sequence Listing Information |
| --- |

SEQ ID NO: 68 LCDR1 RASQRLNSYLH

SEQ ID NO: 69 LCDR2 ATSTLQS

SEQ ID NO: 70 LCDR3 QLSRT

Antibody 8 (expressed form of Antibody 7)
SEQ ID NO: 71
caggtacagctgcagcagtcaggtccaggactggtgaagccctcgcagaccctctccctcacctgtgtcat
ctccggagacactgtctctagcaacagagctacttggaattggatgaggcagtccccattgagaggccttga
gtggctgggaaggacatactacaggtccaagtggtataatgattacgcagtttctgtgaaaagtcgagtagt
catcaacccagacacatccaagaaccaagtctccctgcagttgaacactgtgactcccgatgactcgggtg
tatacttttgtgcaagaggtggccacatcacggtctttggagtgaatattgacgcttttgacatctgggcctcg
ggacaaaggtcaccgtctcttcag SEQ ID NO: 72
QVQLQQSGPGLVKPSQTLSLTCVISGDTVSSNRATWNWMRQSPLRGLEWL
GRTYYRSKWYNDYAVSVKSRVVINPDTSKNQVSLQLNTVTPDDSGVYFCAR
GGHITVFGVNIDAFDIWGLGTKVTVSS

SEQ ID NO: 73 HCDR1 SNRATWN

SEQ ID NO: 74 HCDR2 RTYYRSKWYNDYAVSVKS

SEQ ID NO: 75 HCDR3 GGHITVFGVNIDAFDI

SEQ ID NO: 76
gacatccagatgacccagtctccatcctccctgtctgcatctgtaggagacagagttaccatctcttgccggg
caagtcagagacttaatagttatctacattggtatcagcagacaccagggcaagcccgaagctgctgatct
atgcaacgtccactttgcaaagtgggtctcaccaagattcagtggcagtggatctgggacagatttcactct
caccatcagcagtctccaacctgaagatgttgcaacttactactgtcaattgagtcggacgttcggccacgg
gaccaaggtggaaatcaaac SEQ ID NO: 77
DIQMTQSPSSLSASVGDRVTISCRASQRLNSYLHWYQQTPGQAPKLLIYATS
TLQSGVSPRFSGSGSGTDFTLTISSLQPEDVATYYCQLSRTFGHGTKVEIK

SEQ ID NO: 78 LCDR1 RASQRLNSYLH

SEQ ID NO: 79 LCDR2 ATSTLQS

SEQ ID NO: 80 LCDR3 QLSRT

Antibody 9 (original cDNA)
SEQ ID NO: 81
caagtagagctgcagcagtcaggtccaggactggtgaagccctcgcagaccctctcactcacctgtgccat
ctccggggacagtgtctctagcaacagtgctacttggaactggatcaggcagtccccatcgagaggccttg
agtggctgggaaggacatactacaggtccaagtggtataatgattatgcagattttctgaaaaggcgaataa
ccatcaatccagacacatccaacaacgaggtctccctgcggctgacctctgtgactcccgacgacacggct
ttgtattactgtgcaagaggtggccacattacggtgtttggagtgaatattgacgcctttgacgtctggggccaa
gggacaatggccaccgtctcttcag SEQ ID NO: 82
QVELQQSGPGLVKPSQTLSLTCAISGDSVSSNSATWNWIRQSPSRGLEWL
GRTYYRSKWYNDYADFLKRRITINPDTSNNEVSLRLTSVTPDDTALYYCARG
GHITVFGVNIDAFDVWGQGTMATVSS

SEQ ID NO: 83 HCDR1 SNSATWN

SEQ ID NO: 84 HCDR2 RTYYRSKWYNDYADFLKR

SEQ ID NO: 85 HCDR3 GGHITVFGVNIDAFDV

SEQ ID NO: 86
gacatccaggtgacccagtctccatcctccctgtctgcatctgtaggagacagaatcaccatctcttgccgga
caagtcagagccttaggagctatttacattggtatcagcaaaaaccagggaaagcccctaagctcctgatct
atgcttcatccactttacaaagtggggtcccatcaaggttcagtggcagtggatctgggacagatttcactctc
accatcagcaatctccaacctgaagattttgcaacttactactgtcaactgagtcggacgttcggccaaggg
accaaggttgaaatcaaac SEQ ID NO: 87
DIQVTQSPSSLSASVGDRITISCRTSQSLRSYLHWYQQKPGKAPKLLIYASST
LQSGVPSRFSGSGSGTDFTLTISNLQPEDFATYYCQLSRTFGQGTKVEIK

SEQ ID NO: 88 LCDR1 RTSQSLRSYLH

SEQ ID NO: 89 LCDR2 ASSTLQS

SEQ ID NO: 90 LCDR3 QLSRT

Antibody 10 (expressed form of Antibody 9)
SEQ ID NO: 91
caggtacagctgcagcagtcaggtccaggactggtgaagccctcgcagaccctctcactcacctgtgccat
ctccggggacagtgtctctagcaacagtgctacttggaactggatcaggcagtccccatcgagaggccttg
agtggctgggaaggacatactacaggtccaagtggtataatgattatgcagattttctgaaaaggcgaataa
ccatcaatccagacacatccaacaacgaggtctccctgcggctgacctctgtgactcccgacgacacggct
ttgtattactgtgcaagaggtggccacattacggtgtttggagtgaatattgacgcctttgacgtctggggccaa
gggacaatggtcaccgtctcttcag SEQ ID NO: 92
QVQLQQSGPGLVKPSQTLSLTCAISGDSVSSNSATWNWIRQSPSRGLEWL
GRTYYRSKWYNDYADFLKRRITINPDTSNNEVSLRLTSVTPDDTALYYCARG
GHITVFGVNIDAFDVWGQGTMVTVSS

SEQ ID NO: 93 HCDR1 SNSATWN

SEQ ID NO: 94 HCDR2 RTYYRSKWYNDYADFLKR

SEQ ID NO: 95 HCDR3 GGHITVFGVNIDAFDV

SEQ ID NO: 96
gacatccagatgacccagtctccatcctccctgtctgcatctgtaggagacagaatcaccatctcttgccgga
caagtcagagcctaggagctatttacattggtatcagcaaaaaccagggaaagcccctaagctcctgatct
atgcttcatccactttacaaagtggggtcccatcaaggttcagtggcagtggatctgggacagatttcactctc
accatcagcaatctccaacctgaagattttgcaacttactactgtcaactgagtcggacgttcggccaaggg
accaaggtggagatcaaac SEQ ID NO: 97
DIQMTQSPSSLSASVGDRITISCRTSQSLRSYLHWYQQKPGKAPKLLIYASS
TLQSGVPSRFSGSGSGTDFTLTISNLQPEDFATYYCQLSRTFGQGTKVEIK

SEQ ID NO: 98 LCDR1 RTSQSLRSYLH

SEQ ID NO: 99 LCDR2 ASSTLQS

SEQ ID NO: 100 LCDR3 QLSRT

Antibody 11
SEQ ID NO: 101
caggtccagctgcagcagagcggccccggactggtcaagccttcacagacactgagcctgacatgcgcc
attagcggagatagcgtgagctcctacaatgccgtgtggaactggatcaggcagtctccaagtcgaggact
ggagtggctgggacgaacatactatagatccgggtggtacaatgactatgctgaatcagtgaaaagccga
attactatcaaccccgatacctccaagaatcagttctctctgcagctgaacagtgtgacccctgaggacaca
gccgtgtactactgcgccagaagcggccatatcaccgtctttggcgtcaatgtggatgctttcgatatgtgggg
gcaggggactatggtcaccgtgtcaagc SEQ ID NO: 102
QVQLQQSGPGLVKPSQTLSLTCAISGDSVSSYNAVWNWIRQSPSRGLEWL
GRTYYRSGWYNDYAESVKSRITINPDTSKNQFSLQLNSVTPEDTAVYYCAR
SGHITVFGVNVDAFDMWGQGTMVTVSS

SEQ ID NO: 103 HCDR1 SYNAVWN

SEQ ID NO: 104 HCDR2 RTYYRSGWYNDYAESVKS

SEQ ID NO: 105 HCDR3 SGHITVFGVNVDAFDM

SEQ ID NO: 106
gatattcagatgacccagagcccttccagcctgtccgcttcagtggggatcgagtgaccattacctgccga
accagccagagcctgagctcctacacgcactggtatcagcagaagcccggcaaagcccctaagctgctg
atctacgccgcttctagtcggctgtccggagtgccaagccggttctccggatctggagtggaaccgacttta
ccctgacaatttcaagcctgcagcccgaggatttcgctacatactactgtcagcagagcagaactttcgggc
agggcactaaggtggagatcaaa SEQ ID NO: 107
DIQMTQSPSSLSASVGDRVTITCRTSQSLSSYTHWYQQKPGKAPKLLIYAAS
SRLSGVPSRFSGSGSGTDFTLTISSLQPEDFATYYCQQSRTFGQGTKVE1K

SEQ ID NO: 108 LCDR1 RTSQSLSSYTH

SEQ ID NO: 109 LCDR2 AASSRLS

SEQ ID NO: 110 LCDR3 QQSRT

-continued

Sequence Listing Information

Antibody 12
SEQ ID NO: 111
caggtccagctgcagcagagcggccccggactggtcaagccttcacagacactgagcctgacatgcgcc
attagcggagatagcgtgagctcctacaatgccgtgtggaactggatcaggcagtctccaagtcgaggact
ggagtggctgggacgaacatactatagatccggtggtacaatgactatgctgaatcagtgaaaagccga
attactatcaaccccgatacctccaagaatcagttctctctgcagctgaacagtgtgaccctgaggacaca
gccgtgtactactgcgccagaagcggccatatcaccgtctttggcgtcaatgtggatgctttcgatatgtgggg
gcaggggactatggtcaccgtgtcaagc SEQ ID NO: 112
QVQLQQSGPGLVKPSQTLSLTCAISGDSVSSYNAVWNWIRQSPSRGLEWL
GRTYYRSGWYNDYAESVKSRITINPDTSKNQFSLQLNSVTPEDTAVYYCAR
SGHITVFGVNVDAFDMWGQGTMVTVSS

SEQ ID NO: 113 HCDR1 SYNAVWN

SEQ ID NO: 114 HCDR2 RTYYRSGWYNDYAESVKS

SEQ ID NO: 115 HCDR3 SGHITVFGVNVDAFDM

SEQ ID NO: 116
gatattcagatgacccagagcccttccagcctgtccgcttcagtgggggatcgagtgaccattacctgccga
accagccagagcctgagctcctacacgcactggtatcagcagaagcccggcaaagcccctaagctgctg
atctacgccgcttctagtcgggggtccggagtgccaagccggttctccggatctgggagtggaaccgactttt
accctgacaatttcaagcctgcagcccgaggatttcgctacatactactgtcagcagagcagaactttcggg
cagggcactaaggtggagatcaaa SEQ ID NO: 117
DIQMTQSPSSLSASVGDRVTITCRTSQSLSSYTHWYQQKPGKAPKLLIYAAS
SRGSGVPSRFSGSGSGTDFTLTISSLQPEDFATYYCQQSRTFGQGTKVEIK

SEQ ID NO: 118 LCDR1 RTSQSLSSYTH

SEQ ID NO: 119 LCDR2 AASSRGS

SEQ ID NO: 120 LCDR3 QQSRT

Antibody 13
SEQ ID NO: 121
caggtccagctgcagcagagcggccccggactggtcaagccttcacagacactgagcctgacatgcgcc
attagcggagatagcgtgagctcctacaatgccgtgtggaactggatcaggcagtctccaagtcgaggact
ggagtggctgggacgaacatactatagatccggtggtacaatgactatgctgaatcagtgaaaagccga
attactatcaaccccgatacctccaagaatcagttctctctgcagctgaacagtgtgaccctgaggacaca
gccgtgtactactgcgccagaagcggccatatcaccgtctttggcgtcaatgtggatgctttcgatatgtgggg
gcaggggactatggtcaccgtgtcaagc SEQ ID NO: 122
QVQLQQSGPGLVKPSQTLSLTCAISGDSVSSYNAVWNWIRQSPSRGLEWL
GRTYYRSGWYNDYAESVKSRITINPDTSKNQFSLQLNSVTPEDTAVYYCAR
SGHITVFGVNVDAFDMWGQGTMVTVSS

SEQ ID NO: 123 HCDR1 SYNAVWN

SEQ ID NO: 124 HCDR2 RTYYRSGWYNDYAESVKS

SEQ ID NO: 125 HCDR3 SGHITVFGVNVDAFDM

SEQ ID NO: 126
gatattcagatgacccagagcccttccagcctgtccgcttcagtgggggatcgagtgaccattacctgccga
accagccagagcctgagctcctacgaccactggtatcagcagaagcccggcaaagcccctaagctgctg
atctacgccgcttctagtcggctgtccggagtgccaagccggttctccggatctgggagtggaaccgacttta
ccctgacaatttcaagcctgcagcccgaggatttcgctacatactactgtcagcagagcagaactttcgggc
agggcactaaggtggagatcaaa SEQ ID NO: 127
DIQMTQSPSSLSASVGDRVTITCRTSQSLSSYDHWYQQKPGKAPKLLIYAAS
SRLSGVPSRFSGSGSGTDFTLTISSLQPEDFATYYCQQSRTFGQGTKVE1K

SEQ ID NO: 128 LCDR1 RTSQSLSSYDH

SEQ ID NO: 129 LCDR2 AASSRLS

SEQ ID NO: 130 LCDR3 QQSRT

Antibody 14
SEQ ID NO: 131
caggtccagctgcagcagagcggccccggactggtcaagccttcacagacactgagcctgacatgcgcc attagcggagatagcgtgagctccaacaatgccgtgtggaactggatcaggcagtctccaagtcgaggac
tggagtggctgggacgaacatactatagatccaagtggtacaatgactatgctgaatcagtgaaaagccg
aattactatcaaccccgatacctccaagaatcagttctctctgcagctgaacagtgtgaccctgaggacac
agccgtgtactactgcgccagaagcggccatatcaccgtctttggcgtcaatgtggatgctttcgatatgtggg
ggcaggggaccacagtcaccgtctcctca SEQ ID NO: 132
QVQLQQSGPGLVKPSQTLSLTCAISGDSVSSNNAVWNWIRQSPSRGLEWL
GRTYYRSKWYNDYAESVKSRITINPDTSKNQFSLQLNSVTPEDTAVYYCAR
SGHITVFGVNVDAFDMWGQGTTVTVSS

SEQ ID NO: 133 HCDR1 SNNAVWN

SEQ ID NO: 134 HCDR2 RTYYRSKWYNDYAESVKS

SEQ ID NO: 135 HCDR3 SGHITVFGVNVDAFDM

SEQ ID NO: 136
gatattcagatgacccagagcccttccagcctgtccgcttcagtgggggatcgagtgaccattacctgccga
accagccagagcctgagctcctacacgcactggtatcagcagaagcccggcaaagcccctaagctgctg
atctacgccgcttctagtcggctgtccggagtgccaagccggttctccggatctgggagtggaaccgactttta
ccctgacaatttcaagcctgcagcccgaggatttcgctacatactactgtcagcagagcagaactttcgggc
agggcactaaggtggagatcaaa SEQ ID NO: 137
DIQMTQSPSSLSASVGDRVTITCRTSQSLSSYTHWYQQKPGKAPKLLIYAAS
SRLSGVPSRFSGSGSGTDFTLTISSLQPEDFATYYCQQSRTFGQGTKVE1K

SEQ ID NO: 138 LCDR1 RTSQSLSSYTH

SEQ ID NO: 139 LCDR2 AASSRLS

SEQ ID NO: 140 LCDR3 QQSRT

Antibody 15
SEQ ID NO: 141
caggtccagctgcagcagagcggccccggactggtcaagccttcacagacactgagcctgacatgcgcc
attagcggagatagcgtgagctccaacaatgccgtgtggaactggatcaggcagtctccaagtcgaggac
tggagtggctgggacgaacatactatagatccaagtggtacaatgactatgctgaatcagtgaaaagccg
aattactatcaaccccgatacctccaagaatcagttctctctgcagctgaacagtgtgaccctgaggacac
agccgtgtactactgcgccagaagcggccatatcaccgtctttggcgtcaatgtggatgctttcgatatgtggg
ggcaggggaccacagtcaccgtctcctca SEQ ID NO: 142
QVQLQQSGPGLVKPSQTLSLTCAISGDSVSSNNAVWNWIRQSPSRGLEWL
GRTYYRSKWYNDYAESVKSRITINPDTSKNQFSLQLNSVTPEDTAVYYCAR
SGHITVFGVNVDAFDMWGQGTTVTVSS

SEQ ID NO: 143 HCDR1 SNNAVWN

SEQ ID NO: 144 HCDR2 RTYYRSKWYNDYAESVKS

SEQ ID NO: 145 HCDR3 SGHITVFGVNVDAFDM

SEQ ID NO: 146
gatattcagatgacccagagcccttccagcctgtccgcttcagtgggggatcgagtgaccattacctgccga
accagccagagcctgagytcctacacgcactggtatcagcagaagcccggcaaagcccctaagctgctg
atctacgccgcttctagtcggggtccggagtgccaagccggttctccggatctgggagtggaaccgactttt
accctgacaatttcaagcctgcagcccgaggatttcgctacatactactgtcagcagagcagaactttcggg
cagggcactaaggtggagatcaaa SEQ ID NO: 147
DIQMTQSPSSLSASVGDRVTITCRTSQSLSSYTHWYQQKPGKAPKLLIYAAS
SRGSGVPSRFSGSGSGTDFTLTISSLQPEDFATYYCQQSRTFGQGTKVEIK

SEQ ID NO: 148 LCDR1 RTSQSLSSYTH

SEQ ID NO: 149 LCDR2 AASSRGS

SEQ ID NO: 150 LCDR3 QQSRT

Antibody 3-GL
SEQ ID NO: 151
caggtccagctgcagcagagcggccccggactggtcaagccttcacagacactgagcctgacatgcgcc
attagcggagatagcgtgagctccaacaatgccgtgtggaactggatcaggcagtctccaagtcgaggac
tggagtggctgggacgaacatactatagatccaagtggtacaatgactatgctgaatcagtgaaaagccg
aattactatcaaccccgatacctccaagaatcagttctctctgcagctgaacagtgtgaccctgaggacac

| Sequence Listing Information |
|---|
| agccgtgtactactgcgccagaagcggccatatcaccgtctttggcgtcaatgtggatgctttcgatatgtggg<br>ggcaggggaccacagtcaccgtctcctca<br><br>SEQ ID NO: 152<br>QVQLQQSGPGLVKPSQTLSLTCAISGDSVSSNNAVWNWIRQSPSRGLEWL<br>GRTYYRSKWYNDYAESVKSRITINPDTSKNQFSLQLNSVTPEDTAVYYCAR<br>SGHITVFGVNVDAFDMWGQGTTVTVSS<br><br>SEQ ID NO: 153 HCDR1 SNNAVWN<br><br>SEQ ID NO: 154 HCDR2 RTYYRSKWYNDYAESVKS<br><br>SEQ ID NO: 155 HCDR3 SGHITVFGVNVDAFDM<br><br>SEQ ID NO: 156<br>gatattcagatgacccagagcccttccagcctgtccgcttcagtgggggatcgagtgaccattacctgccga<br>accagccagagcctgagctcctacctgcactggtatcagcagaagcccggcaaagcccctaagctgctg<br>atctacgccgcttctagtctgcagtccggagtgccaagccggttctccggatctggggagtggaaccgactttta<br>ccctgacaatttcaagcctgcagcccgaggatttcgctacatactactgtcagcagagcagaactttcgggc<br>agggcactaaggtggagatcaaa<br><br>SEQ ID NO: 157<br>DIQMTQSPSSLSASVGDRVTITCRTSQSLSSYLHWYQQKPGKAPKLLIYAAS<br>SLQSGVPSRFSGSGSGTDFTLTISSLQPEDFATYYCQQSRTFGQGTKVEIK<br><br>SEQ ID NO: 158 LCDR1 RTSQSLSSYLH<br><br>SEQ ID NO: 159 LCDR2 AASSLQS<br><br>SEQ ID NO: 160 LCDR3 QQSRT |

The invention claimed is:

1. An isolated antibody or a binding fragment thereof that is capable of binding to influenza A virus hemagglutinin and neutralizing at least one group 1 subtype and at least 1 group 2 subtype of influenza A virus, wherein the antibody or fragment thereof includes a set of six CDRs: HCDR1, HCDR2, HCDR3, LCDR1, LCDR2, LCDR3 in which the set of six CDRs comprises the HCDR1 of SEQ ID NO.: 103, the HCDR2 of SEQ ID NO.: 104, the HCDR3 of SEQ ID NO.: 105, the LCDR1 of SEQ ID NO.: 108, the LCDR2 of SEQ ID NO.: 109 and the LCDR3 of SEQ ID NO.: 110.

2. The antibody or binding fragment according to claim 1, wherein the antibody or binding fragment is capable of neutralizing one or more influenza A virus group 1 subtype selected from: H1, H2, H5, H6, H8, H9, H11, H12, H13, H16 and variants thereof; and one or more influenza A virus group 2 subtypes selected from: H3, H4, H7, H10, H14 and H15 and variants thereof.

3. The antibody or binding fragment thereof according to claim 1, wherein the antibody or binding fragment is capable of neutralizing group 1 subtypes: H1, H2, H5, H6 and H9 and group 2 subtypes H3 and H7; or wherein the antibody or binding fragment is capable of neutralizing group 1 subtypes: H1, H2, H5 and H6 and group 2 subtypes H3 and H7.

4. The antibody or binding fragment thereof according to claim 1 comprising a VH having at least 75% identity and/or a VL having at least 75% identity to a VH and/or VL comprising the VH of SEQ ID NO.: 102 and the VL of SEQ ID NO.: 107.

5. The antibody or binding fragment thereof according to claim 1 comprising a VH and a VL comprising the VH of SEQ ID NO.: 102 and the VL of SEQ ID NO.: 107.

6. The antibody or binding fragment thereof according to claim 1, wherein the antibody or binding fragment is selected from the group consisting of: an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual-specific antibody, and a bispecific antibody.

7. The antibody or binding fragment thereof according to claim 1, wherein the VH comprises human germline framework VH6-1, the VL comprises human germline framework VK1-39, and combination thereof.

8. The antibody or binding fragment thereof according to claim 1, comprising an Fc region.

9. The antibody or binding fragment thereof according to claim 1, wherein the antibody is an IgG1, IgG2 or IgG4 or fragment thereof.

10. An isolated nucleic acid encoding an antibody or binding fragment thereof according to claim 1.

11. A vector comprising an isolated nucleic acid according to claim 10.

12. A host cell comprising the isolated nucleic acid according to claim 10.

13. A composition comprising an antibody or binding fragment thereof according to claim 1 and a pharmaceutically acceptable carrier.

14. A composition comprising an antibody or binding fragment thereof according to claim 1, 25 mM His and 0.15M NaCl at pH 6.0.

15. The antibody or binding fragment thereof according to claim 9, wherein the Fc region is a variant Fc region, wherein the antibody or binding fragment thereof has an enhanced serum half-life relative to a native Fc antibody.

16. The isolated antibody or binding fragment thereof according to claim 15, wherein the variant Fc region comprises at least one substitution selected from 221K, 221Y, 225E, 225K, 225W, 228P, 234D, 234E, 234N, 234Q, 234T, 234H, 234Y, 234I, 234V, 234F, 235A, 235D, 235R, 235W, 235P, 235S, 235N, 235Q, 235T, 235H, 235Y, 235I, 235V, 235E, 235F, 236E, 237L, 237M, 237P, 239D, 239E, 239N, 239Q, 239F, 239T, 239H, 239Y, 240I, 240A, 240T, 240M, 241W, 241L, 241Y, 241E, 241R, 243W, 243L, 243Y, 243R, 243Q, 244H, 245A, 247L, 247V, 247G, 250E, 250Q, 251F, 252L, 252Y, 254S, 254T, 255L, 256E, 256F, 256M, 257C, 257M, 257N, 262I, 262A, 262T, 262E, 263I, 263A, 263T, 263M, 264L, 264I, 264W, 264T, 264R, 264F, 264M, 264Y, 264E, 265A, 265G, 265N, 265Q, 265Y, 265F, 265V, 265I, 265L, 265H, 265T, 266I, 266A, 266T, 266M, 267Q, 267L, 268E, 269H, 269Y, 269F, 269R, 270E, 280A, 284M, 292P, 292L, 296E, 296Q, 296D, 296N, 296S, 296T, 296L, 296I, 296H, 296G, 297S, 297D, 297E, 298A, 298H, 298I, 298T, 298F, 299I, 299L, 299A, 299S, 299V, 299H, 299F, 299E, 305I, 308F, 313F, 316D, 318A, 318S, 320A, 320S, 322A, 322S, 325Q, 325L, 325I, 325D, 325E, 325A, 325T, 325V, 325H, 326A, 326D, 326E, 326G, 326M, 326V, 327G, 327W, 327N, 327L, 328S, 328M, 328D, 328E, 328N, 328Q, 328F, 328I, 328V, 328T, 328H, 328A, 329F, 329H, 329Q, 330K, 330G, 330T, 330C, 330L, 330Y, 330V, 330I, 330F, 330R, 330H, 331G, 331A, 331L, 331M, 331F, 331W, 331K, 331Q, 331E, 331S, 331V, 331I, 331C, 331Y, 331H, 331R, 331N, 331D, 331T, 332D, 332S, 332W, 332F, 332E, 332N, 332Q, 332T, 332H, 332Y, 332A, 333A, 333D, 333G, 333Q, 333S, 333V, 334A, 334E, 334H, 334L, 334M, 334Q, 334V, 334Y, 339T, 370E, 370N, 378D, 392T, 396L, 416G, 419H, 421K, 428L, 428F, 433K, 433L, 434A, 434W, 434Y, 436H, 440Y and 443W as numbered by the EU index as set forth in Kabat.

17. The isolated antibody or binding fragment thereof according to claim 16, wherein the variant Fc region comprises at least one substitution selected from 252Y, 254T, 256E as numbered by the EU index as set forth in Kabat.

18. The isolated antibody or binding fragment thereof according to claim 17, wherein the variant Fc region comprises 252Y, 254T, 256E as numbered by the EU index as set forth in Kabat.

19. The isolated antibody or binding fragment thereof according to claim 8, wherein the Fc region is a variant Fc region that comprises at least one substitution selected from 252Y, 254T, 256E as numbered by the EU index as set forth in Kabat.

20. The isolated antibody or binding fragment thereof according to claim 8, wherein the Fc region is a variant Fc region that comprises 252Y, 254T, and 256E as numbered by the EU index as set forth in Kabat.

* * * * *

SEQUENCE LISTING

<160> NUMBER OF SEQ ID NOS: 172

<210> SEQ ID NO 1
<211> LENGTH: 385
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
cagatacagc tgcaggagtc gggtccagga ctggtgaagc cctcgcagac cctctcactc      60
acctgtgcca tctccgggga cagtgtctct agcaacaatg ctgtttggaa ctggatcagg     120
cagtccccat cgagaggcct tgagtggctg gaaggacat actacaggtc caagtggtat      180
aatgattatg cagaatctgt gaaaagtcga ataaccgtca atccagacac atccaagaac    240
cagttctccc tgcacctgaa gtctgtgact cccgaggaca cggctgtgtt ttactgtgta    300
cgatctggcc acattacggt ttttggagtg aatgttgacg cttttgatat gtggggccaa    360
gggacaatgg tcaccgtctc ttcag                                            385

<210> SEQ ID NO 2
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Ile Gln Leu Gln Glu Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Asn Ala Val Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Glu Ser Val Lys Ser Arg Ile Thr Val Asn Pro Asp Thr Ser Lys Asn
65                  70                  75                  80

Gln Phe Ser Leu His Leu Lys Ser Val Thr Pro Glu Asp Thr Ala Val
                85                  90                  95

Phe Tyr Cys Val Arg Ser Gly His Ile Thr Val Phe Gly Val Asn Val
            100                 105                 110

Asp Ala Phe Asp Met Trp Gly Gln Gly Thr Met Val Thr Val Ser Ser
        115                 120                 125

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Asn Asn Ala Val Trp Asn
1               5

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Thr Tyr Tyr Arg Ser Lys Trp Tyr Asn Asp Tyr Ala Glu Ser Val
1               5                   10                  15

Lys Ser

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Gly His Ile Thr Val Phe Gly Val Asn Val Asp Ala Phe Asp Met
1               5                   10                  15

<210> SEQ ID NO 6
<211> LENGTH: 309
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
gacatccaga tcacccagtc gccatcctcc ctgtctgcat ctgtaggaga cagagtaacc     60
atcacttgcc ggacaagtca gagccttagt agctatttac attggtatca gcagaaacca    120

```
gggaaagccc ctaagctcct gatctatgct gcatccagtt tgcaaagtgg ggtcccatca    180
aggttcagtg gcagtggatc tgggacagat ttcactctca ccatcagtag tctgcaacct    240
gaagattttg caacttacta ctgtcaacag agtcggacgt tcggccaagg gaccaaggtg    300
gaaatcaaa                                                            309
```

<210> SEQ ID NO 7
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Ile Gln Ile Thr Gln Ser Pro Ser Ser Leu Ser Ala Ser Val Gly
1               5                   10                  15

Asp Arg Val Thr Ile Thr Cys Arg Thr Ser Gln Ser Leu Ser Ser Tyr
            20                  25                  30

Leu His Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Arg Thr Phe Gly Gln
                85                  90                  95

Gly Thr Lys Val Glu Ile Lys
            100

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Thr Ser Gln Ser Leu Ser Ser Tyr Leu His
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Ala Ser Ser Leu Gln Ser
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

```
Gln Gln Ser Arg Thr
1               5
```

<210> SEQ ID NO 11
<211> LENGTH: 385
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
caggtacagc tgcaggagtc gggtccagga ctggtgaagc cctcgcagac cctctcactc      60
acctgtgcca tctccgggga cagtgtctct agcaacaatg ctgtttggaa ctggatcagg     120
cagtccccat cgagaggcct tgagtggctg ggaaggacat actacaggtc caagtggtat     180
aatgattatg cagaatctgt gaaaagtcga ataaccgtca atccagacac atccaagaac     240
cagttctccc tgcacctgaa gtctgtgact cccgaggaca cggctgtgtt ttactgtgta     300
cgatctggcc acattacggt ttttggagtg aatgttgacg cttttgatat gtggggccaa     360
gggacaatgg tcaccgtctc ttcag                                           385
```

<210> SEQ ID NO 12
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Gln Val Gln Leu Gln Glu Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Asn Ala Val Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Glu Ser Val Lys Ser Arg Ile Thr Val Asn Pro Asp Thr Ser Lys Asn
65                  70                  75                  80

Gln Phe Ser Leu His Leu Lys Ser Val Thr Pro Glu Asp Thr Ala Val
                85                  90                  95

Phe Tyr Cys Val Arg Ser Gly His Ile Thr Val Phe Gly Val Asn Val
            100                 105                 110

Asp Ala Phe Asp Met Trp Gly Gln Gly Thr Met Val Thr Val Ser Ser
        115                 120                 125
```

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

```
Ser Asn Asn Ala Val Trp Asn
1               5
```

```
<210> SEQ ID NO 14
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Thr Tyr Tyr Arg Ser Lys Trp Tyr Asn Asp Tyr Ala Glu Ser Val
1               5                   10                  15

Lys Ser

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Gly His Ile Thr Val Phe Gly Val Asn Val Asp Ala Phe Asp Met
1               5                   10                  15

<210> SEQ ID NO 16
<211> LENGTH: 309
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
gacatccaga tgacccagtc gccatcctcc ctgtctgcat ctgtaggaga cagagtaacc       60
atcacttgcc ggacaagtca gagccttagt agctatttac attggtatca gcagaaacca      120
gggaaagccc ctaagctcct gatctatgct gcatccagtt tgcaaagtgg ggtcccatca      180
aggttcagtg gcagtggatc tgggacagat ttcactctca ccatcagtag tctgcaacct      240
gaagattttg caacttacta ctgtcaacag agtcggacgt tcggccaagg gaccaaggtg      300
gaaatcaaa                                                              309

<210> SEQ ID NO 17
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Ser Leu Ser Ser Tyr
                20                  25                  30

Leu His Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Arg Thr Phe Gly Gln
```

Gly Thr Lys Val Glu Ile Lys
            100

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Thr Ser Gln Ser Leu Ser Ser Tyr Leu His
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Ala Ser Ser Leu Gln Ser
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Gln Ser Arg Thr
1               5

<210> SEQ ID NO 21
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
caggtccagc tgcaggagag cggccccgga ctggtcaagc cttcacagac actgagcctg      60
acatgcgcca ttagcggaga tagcgtgagc tccaacaatg ccgtgtggaa ctggatcagg     120
cagtctccaa gtcgaggact ggagtggctg ggacgaacat actatagatc caagtggtac     180
aatgactatg ctgaatcagt gaaaagccga attactgtca accccgatac ctccaagaat     240
cagttctctc tgcacctgaa aagtgtgacc cctgaggaca cagccgtgtt ctactgcgtc     300
agaagcggcc atatcaccgt ctttggcgtc aatgtggatg cttcgatat gtggggcag     360 gggactatgg tcaccgtgtc aagc                                            384

<210> SEQ ID NO 22
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

Gln Val Gln Leu Gln Glu Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Asn Ala Val Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Glu Ser Val Lys Ser Arg Ile Thr Val Asn Pro Asp Thr Ser Lys Asn
65                  70                  75                  80

Gln Phe Ser Leu His Leu Lys Ser Val Thr Pro Glu Asp Thr Ala Val
                85                  90                  95

Phe Tyr Cys Val Arg Ser Gly His Ile Thr Val Phe Gly Val Asn Val
            100                 105                 110

Asp Ala Phe Asp Met Trp Gly Gln Gly Thr Met Val Thr Val Ser Ser
        115                 120                 125

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Asn Asn Ala Val Trp Asn
1               5

<210> SEQ ID NO 24
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Thr Tyr Tyr Arg Ser Lys Trp Tyr Asn Asp Tyr Ala Glu Ser Val
1               5                   10                  15

Lys Ser

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Gly His Ile Thr Val Phe Gly Val Asn Val Asp Ala Phe Asp Met
1               5                   10                  15

<210> SEQ ID NO 26
<211> LENGTH: 309
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 26

```
gatattcaga tgacccagag cccttccagc ctgtccgctt cagtggggga tcgagtgacc    60
attacctgcc gaaccagcca gagcctgagc tcctacctgc actggtatca gcagaagccc   120
ggcaaagccc ctaagctgct gatctacgcc gcttctagtc tgcagtccgg agtgccaagc   180
cggttctccg gatctgggag tggaaccgac tttacccctg caatttcaag cctgcagccc   240
gaggatttcg ctacatacta ctgtcagcag agcagaactt cgggcaggg cactaaggtg   300 gagatcaaa                                                          309
```

<210> SEQ ID NO 27
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

```
Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Ser Leu Ser Ser Tyr
            20                  25                  30

Leu His Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Arg Thr Phe Gly Gln
                85                  90                  95

Gly Thr Lys Val Glu Ile Lys
            100
```

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Arg Thr Ser Gln Ser Leu Ser Ser Tyr Leu His
1               5                   10
```

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

```
Ala Ala Ser Ser Leu Gln Ser
1               5
```

<210> SEQ ID NO 30
<211> LENGTH: 5

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Gln Ser Arg Thr
1               5

<210> SEQ ID NO 31
<211> LENGTH: 385
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
caggtccagc tgcagcagtc aggtccagga ctggtgaagc cctcgcagac cctctcactc      60
acctgtgcca tctccgggga cagagtctct agcaacagtg ctgtttggaa ctggatcagg     120
cagtccccat cgagaggcct cgagtggctg ggaaggacat attacaggtc caaatggtat     180
tatgattatg cagaatctgt gaaaagtcga atagttatcg acccagacac atccaagaac     240
caggtctccc tgcagttgaa ttctgtgact cccgaggact cggctatata ttactgtgca     300
agaggtggcc acattacggt gtttgggctg aatattgacg cttatgatat ttggggccaa     360
ggggcaaagg tcaccgtgtc ttcag                                           385

<210> SEQ ID NO 32
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Arg Val Ser Ser Asn
                20                  25                  30

Ser Ala Val Trp Asn Trp Ile Arg Gln Ser Pro Ser Arg Gly Leu Glu
            35                  40                  45

Trp Leu Gly Arg Thr Tyr Tyr Arg Ser Lys Trp Tyr Tyr Asp Tyr Ala
        50                  55                  60

Glu Ser Val Lys Ser Arg Ile Val Ile Asp Pro Asp Thr Ser Lys Asn
65                  70                  75                  80

Gln Val Ser Leu Gln Leu Asn Ser Val Thr Pro Glu Asp Ser Ala Ile
                85                  90                  95

Tyr Tyr Cys Ala Arg Gly Gly His Ile Thr Val Phe Gly Leu Asn Ile
            100                 105                 110

Asp Ala Tyr Asp Ile Trp Gly Gln Gly Ala Lys Val Thr Val Ser Ser
        115                 120                 125

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 33

Ser Asn Ser Ala Val Trp Asn
1               5

<210> SEQ ID NO 34
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Thr Tyr Tyr Arg Ser Lys Trp Tyr Tyr Asp Tyr Ala Glu Ser Val
1               5                   10                  15

Lys Ser

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Gly His Ile Thr Val Phe Gly Leu Asn Ile Asp Ala Tyr Asp Ile
1               5                   10                  15

<210> SEQ ID NO 36
<211> LENGTH: 307
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
gacatccagg tgacccagtc tccgtcctcc ctgtctgcat ctgtaggaga cagagtcacc      60
atctcttgcc gggcacagag ccttagcagc tacttacatt ggtatcagca gaaaccaggg    120
caacccccta aactcctgat ctatgctgca accactttgc aaagtggggt cccatcacgg    180
ttcagtggta gtggatctgg gacagatttc actctcacca tcagtacttt ccaagctgaa    240
gatgttgcca cttactattg tcaacagagt cggacgttcg gccaagggac caaggttgaa    300
atcaaac                                                              307

<210> SEQ ID NO 37
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Asp Ile Gln Val Thr Gln Ser Pro Ser Ser Leu Ser Ala Ser Val Gly
1               5                   10                  15

Asp Arg Val Thr Ile Ser Cys Arg Ala Gln Ser Leu Ser Ser Tyr Leu
                20                  25                  30

His Trp Tyr Gln Gln Lys Pro Gly Gln Pro Pro Lys Leu Leu Ile Tyr
            35                  40                  45
```

```
Ala Ala Thr Thr Leu Gln Ser Gly Val Pro Ser Arg Phe Ser Gly Ser
        50                  55                  60

Gly Ser Gly Thr Asp Phe Thr Leu Thr Ile Ser Thr Phe Gln Ala Glu
65                  70                  75                  80

Asp Val Ala Thr Tyr Tyr Cys Gln Gln Ser Arg Thr Phe Gly Gln Gly
                85                  90                  95

Thr Lys Val Glu Ile Lys
            100
```

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

```
Arg Ala Gln Ser Leu Ser Ser Tyr Leu His
1               5                   10
```

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

```
Ala Ala Thr Thr Leu Gln Ser
1               5
```

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

```
Gln Gln Ser Arg Thr
1               5
```

<210> SEQ ID NO 41
<211> LENGTH: 385
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

```
caggtacagc tgcagcagtc aggtccagga ctggtgaagc cctcgcagac cctctcactc      60
acctgtgcca tctccgggga cagagtctct agcaacagtg ctgtttggaa ctggatcagg     120
cagtccccat cgagaggcct cgagtggctg gaaggacat attacaggtc caaatggtat      180
tatgattatg cagaatctgt gaaaagtcga atagttatcg acccagacac atccaagaac    240
caggtctccc tgcagttgaa ttctgtgact cccgaggact cggctatata ttactgtgca    300
agaggtggcc acattacggt gtttgggctg aatattgacg cttatgatat ttggggccaa    360
ggggcaatgg tcaccgtctc ttcag                                           385
```

<210> SEQ ID NO 42
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Arg Val Ser Ser Asn
            20                  25                  30

Ser Ala Val Trp Asn Trp Ile Arg Gln Ser Pro Ser Arg Gly Leu Glu
        35                  40                  45

Trp Leu Gly Arg Thr Tyr Tyr Arg Ser Lys Trp Tyr Tyr Asp Tyr Ala
    50                  55                  60

Glu Ser Val Lys Ser Arg Ile Val Ile Asp Pro Asp Thr Ser Lys Asn
65                  70                  75                  80

Gln Val Ser Leu Gln Leu Asn Ser Val Thr Pro Glu Asp Ser Ala Ile
                85                  90                  95

Tyr Tyr Cys Ala Arg Gly Gly His Ile Thr Val Phe Gly Leu Asn Ile
            100                 105                 110

Asp Ala Tyr Asp Ile Trp Gly Gln Gly Ala Met Val Thr Val Ser Ser
        115                 120                 125

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ser Asn Ser Ala Val Trp Asn
1               5

<210> SEQ ID NO 44
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Thr Tyr Tyr Arg Ser Lys Trp Tyr Tyr Asp Tyr Ala Glu Ser Val
1               5                   10                  15

Lys Ser

<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Gly His Ile Thr Val Phe Gly Leu Asn Ile Asp Ala Tyr Asp Ile
1               5                   10                  15

<210> SEQ ID NO 46
<211> LENGTH: 307
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46

```
gacatccaga tgacccagtc tccgtcctcc ctgtctgcat ctgtaggaga cagagtcacc    60
atctcttgcc gggcacagag ccttagcagc tacttacatt ggtatcagca gaaaccaggg   120 caaccccta  aactcctgat ctatgctgca accactttgc aaagtggggt cccatcacgg   180
ttcagtggta gtggatctgg gacagatttc actctcacca tcagtacttt ccaagctgaa   240
gatgttgcca cttactattg tcaacagagt cggacgttcg gccaagggac caaggtggag   300
atcaaac                                                             307
```

<210> SEQ ID NO 47
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Asp Ile Gln Met Thr Gln Ser Pro Ser Ser Leu Ser Ala Ser Val Gly
1               5                   10                  15

Asp Arg Val Thr Ile Ser Cys Arg Ala Gln Ser Leu Ser Ser Tyr Leu
            20                  25                  30

His Trp Tyr Gln Gln Lys Pro Gly Gln Pro Pro Lys Leu Leu Ile Tyr
        35                  40                  45

Ala Ala Thr Thr Leu Gln Ser Gly Val Pro Ser Arg Phe Ser Gly Ser
    50                  55                  60

Gly Ser Gly Thr Asp Phe Thr Leu Thr Ile Ser Thr Phe Gln Ala Glu
65                  70                  75                  80

Asp Val Ala Thr Tyr Tyr Cys Gln Gln Ser Arg Thr Phe Gly Gln Gly
                85                  90                  95

Thr Lys Val Glu Ile Lys
            100

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg Ala Gln Ser Leu Ser Ser Tyr Leu His
1               5                   10

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Ala Thr Thr Leu Gln Ser
1               5

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Gln Ser Arg Thr
1               5

<210> SEQ ID NO 51
<211> LENGTH: 385
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
caggtacagc tgcagcagtc aggtccagga ctggtgaagc cctcgcagac cctctcactc      60
acctgtgcca tctccgggga cagagtctct agcaacagtg ctgtttggaa ctggatcagg     120
cagtccccat cgagaggcct cgagtggctg gaaggacat attacaggtc caaatggtat     180
tatgattatg cagaatctgt gaaaagtcga atagttatcg acccagacac atccaagaac     240
caggtctccc tgcagttgaa ttctgtgact cccgaggact cggctatata ttactgtgca     300
agaggtggcc acattacgga gtttgggctg aatattgacg cttatgatat ttggggccaa     360
ggggcaatgg tcaccgtctc ttcag                                           385

<210> SEQ ID NO 52
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Arg Val Ser Ser Asn
            20                  25                  30

Ser Ala Val Trp Asn Trp Ile Arg Gln Ser Pro Ser Arg Gly Leu Glu
        35                  40                  45

Trp Leu Gly Arg Thr Tyr Tyr Arg Ser Lys Trp Tyr Tyr Asp Tyr Ala
    50                  55                  60

Glu Ser Val Lys Ser Arg Ile Val Ile Asp Pro Asp Thr Ser Lys Asn
65                  70                  75                  80

Gln Val Ser Leu Gln Leu Asn Ser Val Thr Pro Glu Asp Ser Ala Ile
                85                  90                  95

Tyr Tyr Cys Ala Arg Gly Gly His Ile Thr Glu Phe Gly Leu Asn Ile
            100                 105                 110

Asp Ala Tyr Asp Ile Trp Gly Gln Gly Ala Met Val Thr Val Ser Ser
        115                 120                 125

-continued

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ser Asn Ser Ala Val Trp Asn
1               5

<210> SEQ ID NO 54
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Arg Thr Tyr Tyr Arg Ser Lys Trp Tyr Tyr Asp Tyr Ala Glu Ser Val
1               5                   10                  15

Lys Ser

<210> SEQ ID NO 55
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Gly His Ile Thr Glu Phe Gly Leu Asn Ile Asp Ala Tyr Asp Ile
1               5                   10                  15

<210> SEQ ID NO 56
<211> LENGTH: 307
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
gacatccaga tgacccagtc tccgtcctcc ctgtctgcat ctgtaggaga cagagtcacc      60
atctcttgcc gggcacagag ccttagcagc tacttacatt ggtatcagca gaaaccaggg    120 caaccccta aactcctgat ctatgctgca accactttgc aaagtggggt cccatcacgg    180
ttcagtggta gtggatctgg gacagatttc actctcacca tcagtacttt ccaagctgaa    240
gatgttgcca cttactattg tcaacagagt cggacgttcg gccaagggac caaggtggag    300
atcaaac                                                              307

<210> SEQ ID NO 57
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Asp Ile Gln Met Thr Gln Ser Pro Ser Ser Leu Ser Ala Ser Val Gly
1               5                   10                  15

```
Asp Arg Val Thr Ile Ser Cys Arg Ala Gln Ser Leu Ser Ser Tyr Leu
            20                  25                  30

His Trp Tyr Gln Gln Lys Pro Gly Gln Pro Pro Lys Leu Leu Ile Tyr
        35                  40                  45

Ala Ala Thr Thr Leu Gln Ser Gly Val Pro Ser Arg Phe Ser Gly Ser
50                  55                  60

Gly Ser Gly Thr Asp Phe Thr Leu Thr Ile Ser Thr Phe Gln Ala Glu
65                  70                  75                  80

Asp Val Ala Thr Tyr Tyr Cys Gln Gln Ser Arg Thr Phe Gly Gln Gly
                85                  90                  95

Thr Lys Val Glu Ile Lys
            100
```

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

```
Arg Ala Gln Ser Leu Ser Ser Tyr Leu His
1               5                   10
```

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

```
Ala Ala Thr Thr Leu Gln Ser
1               5
```

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

```
Gln Gln Ser Arg Thr
1               5
```

<210> SEQ ID NO 61
<211> LENGTH: 385
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61

```
caggtacagc tgcagcagtc aggtccagga ctggtgaagc cctcgcagac cctctccctc     60
acctgtgtca tctccggaga cactgtctct agcaacagag ctacttggaa ttggatgagg    120
cagtccccat tgagaggcct tgagtggctg ggaaggacat actacaggtc caagtggtat    180
aatgattacg cagtttctgt gaaaagtcga gtagtcatca acccagacac atccaagaac    240
```

```
caagtctccc tgcagttgaa cactgtgact cccgatgact cgggtgtata cttttgtgca    300
agaggtggcc acatcacggt ctttggagtg aatattgacg cttttgacat ctggggcctc    360
gggacaaagg tcaccgtctc ttcag                                          385
```

```
<210> SEQ ID NO 62
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Val Gln Leu Gln Gln Ser Gly Pro Gly Leu Val Lys Pro Ser Gln
1               5                   10                  15

Thr Leu Ser Leu Thr Cys Val Ile Ser Gly Asp Thr Val Ser Ser Asn
            20                  25                  30

Arg Ala Thr Trp Asn Trp Met Arg Gln Ser Pro Leu Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Val Val Ile Asn Pro Asp Thr Ser Lys Asn
65                  70                  75                  80

Gln Val Ser Leu Gln Leu Asn Thr Val Thr Pro Asp Asp Ser Gly Val
                85                  90                  95

Tyr Phe Cys Ala Arg Gly Gly His Ile Thr Val Phe Gly Val Asn Ile
            100                 105                 110

Asp Ala Phe Asp Ile Trp Gly Leu Gly Thr Lys Val Thr Val Ser Ser
        115                 120                 125

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ser Asn Arg Ala Thr Trp Asn
1               5

<210> SEQ ID NO 64
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Thr Tyr Tyr Arg Ser Lys Trp Tyr Asn Asp Tyr Ala Val Ser Val
1               5                   10                  15

Lys Ser

<210> SEQ ID NO 65
<211> LENGTH: 16
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 65

Gly Gly His Ile Thr Val Phe Gly Val Asn Ile Asp Ala Phe Asp Ile
1               5                   10                  15

<210> SEQ ID NO 66
<211> LENGTH: 310
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66

```
gacatccagg tgacccagtc tccatcctcc ctgtctgcat ctgtaggaga cagagttacc      60
atctcttgcc gggcaagtca gagacttaat agttatctac attggtatca gcagacacca     120
gggcaagccc cgaagctgct gatctatgca acgtccactt tgcaaagtgg ggtctcacca     180
agattcagtg gcagtggatc tgggacagat ttcactctca ccatcagcag tctccaacct     240
gaagatgttg caacttacta ctgtcaattg agtcggacgt tcggccacgg gaccaaggtt     300
gaaatcaaac                                                            310
```

<210> SEQ ID NO 67
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Asp Ile Gln Val Thr Gln Ser Pro Ser Ser Leu Ser Ala Ser Val Gly
1               5                   10                  15

Asp Arg Val Thr Ile Ser Cys Arg Ala Ser Gln Arg Leu Asn Ser Tyr
            20                  25                  30

Leu His Trp Tyr Gln Gln Thr Pro Gly Gln Ala Pro Lys Leu Leu Ile
        35                  40                  45

Tyr Ala Thr Ser Thr Leu Gln Ser Gly Val Ser Pro Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Leu Ser Arg Thr Phe Gly His
                85                  90                  95

Gly Thr Lys Val Glu Ile Lys
            100

<210> SEQ ID NO 68
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Ala Ser Gln Arg Leu Asn Ser Tyr Leu His
1               5                   10

<210> SEQ ID NO 69
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ala Thr Ser Thr Leu Gln Ser
1               5

<210> SEQ ID NO 70
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gln Leu Ser Arg Thr
1               5

<210> SEQ ID NO 71
<211> LENGTH: 385
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
caggtacagc tgcagcagtc aggtccagga ctggtgaagc cctcgcagac cctctccctc      60
acctgtgtca tctccggaga cactgtctct agcaacagag ctacttggaa ttggatgagg     120
cagtccccat tgagaggcct tgagtggctg gaaggacat actacaggtc caagtggtat      180
aatgattacg cagtttctgt gaaaagtcga gtagtcatca acccagacac atccaagaac    240
caagtctccc tgcagttgaa cactgtgact cccgatgact cgggtgtata cttttgtgca    300
agaggtggcc acatcacggt cttggagtg aatattgacg cttttgacat ctggggcctc    360
gggacaaagg tcaccgtctc ttcag                                          385

<210> SEQ ID NO 72
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Val Gln Leu Gln Gln Ser Gly Pro Gly Leu Val Lys Pro Ser Gln
1               5                   10                  15

Thr Leu Ser Leu Thr Cys Val Ile Ser Gly Asp Thr Val Ser Ser Asn
            20                  25                  30

Arg Ala Thr Trp Asn Trp Met Arg Gln Ser Pro Leu Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Val Val Ile Asn Pro Asp Thr Ser Lys Asn
65                  70                  75                  80

Gln Val Ser Leu Gln Leu Asn Thr Val Thr Pro Asp Asp Ser Gly Val
                85                  90                  95
```

Tyr Phe Cys Ala Arg Gly Gly His Ile Thr Val Phe Gly Val Asn Ile
            100                 105                 110

Asp Ala Phe Asp Ile Trp Gly Leu Gly Thr Lys Val Thr Val Ser Ser
        115                 120                 125

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ser Asn Arg Ala Thr Trp Asn
1               5

<210> SEQ ID NO 74
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Arg Thr Tyr Tyr Arg Ser Lys Trp Tyr Asn Asp Tyr Ala Val Ser Val
1               5                   10                  15

Lys Ser

<210> SEQ ID NO 75
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Gly His Ile Thr Val Phe Gly Val Asn Ile Asp Ala Phe Asp Ile
1               5                   10                  15

<210> SEQ ID NO 76
<211> LENGTH: 310
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76
gacatccaga tgacccagtc tccatcctcc ctgtctgcat ctgtaggaga cagagttacc      60
atctcttgcc gggcaagtca gagacttaat agttatctac attggtatca gcagacacca     120
gggcaagccc cgaagctgct gatctatgca acgtccactt tgcaaagtgg ggtctcacca     180
agattcagtg gcagtggatc tgggacagat ttcactctca ccatcagcag tctccaacct     240
gaagatgttg caacttacta ctgtcaattg agtcggacgt tcggccacgg gaccaaggtg     300
gaaatcaaac                                                            310

<210> SEQ ID NO 77
<211> LENGTH: 103
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 77

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Arg Leu Asn Ser Tyr
            20                  25                  30

Leu His Trp Tyr Gln Gln Thr Pro Gly Gln Ala Pro Lys Leu Leu Ile
        35                  40                  45

Tyr Ala Thr Ser Thr Leu Gln Ser Gly Val Ser Pro Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Leu Ser Arg Thr Phe Gly His
                85                  90                  95

Gly Thr Lys Val Glu Ile Lys
            100

<210> SEQ ID NO 78
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Arg Ala Ser Gln Arg Leu Asn Ser Tyr Leu His
1               5                   10

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ala Thr Ser Thr Leu Gln Ser
1               5

<210> SEQ ID NO 80
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gln Leu Ser Arg Thr
1               5

<210> SEQ ID NO 81
<211> LENGTH: 385
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81

```
caagtagagc tgcagcagtc aggtccagga ctggtgaagc cctcgcagac cctctcactc    60
acctgtgcca tctccgggga cagtgtctct agcaacagtg ctacttggaa ctggatcagg   120
cagtccccat cgagaggcct tgagtggctg ggaaggacat actacaggtc caagtggtat   180
aatgattatg cagattttct gaaaaggcga ataaccatca atccagacac atccaacaac   240
gaggtctccc tgcggctgac ctctgtgact cccgacgaca cggctttgta ttactgtgca   300
agaggtggcc acattacggt gtttggagtg aatattgacg cctttgacgt ctggggccaa   360
gggacaatgg ccaccgtctc ttcag                                         385
```

<210> SEQ ID NO 82
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

```
Gln Val Glu Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Thr Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Asp Phe Leu Lys Arg Arg Ile Thr Ile Asn Pro Asp Thr Ser Asn Asn
65                  70                  75                  80

Glu Val Ser Leu Arg Leu Thr Ser Val Thr Pro Asp Asp Thr Ala Leu
                85                  90                  95

Tyr Tyr Cys Ala Arg Gly Gly His Ile Thr Val Phe Gly Val Asn Ile
            100                 105                 110

Asp Ala Phe Asp Val Trp Gly Gln Gly Thr Met Ala Thr Val Ser Ser
        115                 120                 125
```

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

```
Ser Asn Ser Ala Thr Trp Asn
1               5
```

<210> SEQ ID NO 84
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

```
Arg Thr Tyr Tyr Arg Ser Lys Trp Tyr Asn Asp Tyr Ala Asp Phe Leu
1               5                   10                  15

Lys Arg
```

<210> SEQ ID NO 85
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Gly His Ile Thr Val Phe Gly Val Asn Ile Asp Ala Phe Asp Val
1               5                   10                  15

<210> SEQ ID NO 86
<211> LENGTH: 310
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86
gacatccagg tgacccagtc tccatcctcc ctgtctgcat ctgtaggaga cagaatcacc    60
atctcttgcc ggacaagtca gagccttagg agctatttac attggtatca gcaaaaacca   120
gggaaagccc ctaagctcct gatctatgct tcatccactt tacaaagtgg ggtcccatca   180
aggttcagtg gcagtggatc tgggacagat ttcactctca ccatcagcaa tctccaacct   240
gaagattttg caacttacta ctgtcaactg agtcggacgt tcggccaagg gaccaaggtt   300
gaaatcaaac                                                          310

<210> SEQ ID NO 87
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Asp Ile Gln Val Thr Gln Ser Pro Ser Ser Leu Ser Ala Ser Val Gly
1               5                   10                  15

Asp Arg Ile Thr Ile Ser Cys Arg Thr Ser Gln Ser Leu Arg Ser Tyr
            20                  25                  30

Leu His Trp Tyr Gln Gln Lys Pro Gly Lys Ala Pro Lys Leu Leu Ile
        35                  40                  45

Tyr Ala Ser Ser Thr Leu Gln Ser Gly Val Pro Ser Arg Phe Ser Gly
    50                  55                  60

Ser Gly Ser Gly Thr Asp Phe Thr Leu Thr Ile Ser Asn Leu Gln Pro
65                  70                  75                  80

Glu Asp Phe Ala Thr Tyr Tyr Cys Gln Leu Ser Arg Thr Phe Gly Gln
                85                  90                  95

Gly Thr Lys Val Glu Ile Lys
            100

<210> SEQ ID NO 88
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Arg Thr Ser Gln Ser Leu Arg Ser Tyr Leu His
1               5                   10

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ala Ser Ser Thr Leu Gln Ser
1               5

<210> SEQ ID NO 90
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gln Leu Ser Arg Thr
1               5

<210> SEQ ID NO 91
<211> LENGTH: 385
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91
caggtacagc tgcagcagtc aggtccagga ctggtgaagc cctcgcagac cctctcactc      60
acctgtgcca tctccgggga cagtgtctct agcaacagtg ctacttggaa ctggatcagg     120
cagtccccat cgagaggcct tgagtggctg gaaggacat actacaggtc caagtggtat      180
aatgattatg cagattttct gaaaaggcga ataaccatca tccagacac atccaacaac      240 gaggtctccc tgcggctgac ctctgtgact cccgacgaca cggctttgta ttactgtgca    300
agaggtggcc acattacggt gtttggagtg aatattgacg cctttgacgt ctggggccaa    360
gggacaatgg tcaccgtctc ttcag                                          385

<210> SEQ ID NO 92
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Thr Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

```
Asp Phe Leu Lys Arg Arg Ile Thr Ile Asn Pro Asp Thr Ser Asn Asn
 65                  70                  75                  80

Glu Val Ser Leu Arg Leu Thr Ser Val Thr Pro Asp Asp Thr Ala Leu
                 85                  90                  95

Tyr Tyr Cys Ala Arg Gly Gly His Ile Thr Val Phe Gly Val Asn Ile
            100                 105                 110

Asp Ala Phe Asp Val Trp Gly Gln Gly Thr Met Val Thr Val Ser Ser
        115                 120                 125

<210> SEQ ID NO 93
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ser Asn Ser Ala Thr Trp Asn
1               5

<210> SEQ ID NO 94
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Arg Thr Tyr Tyr Arg Ser Lys Trp Tyr Asn Asp Tyr Ala Asp Phe Leu
1               5                   10                  15

Lys Arg

<210> SEQ ID NO 95
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Gly His Ile Thr Val Phe Gly Val Asn Ile Asp Ala Phe Asp Val
1               5                   10                  15

<210> SEQ ID NO 96
<211> LENGTH: 310
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
gacatccaga tgacccagtc tccatcctcc ctgtctgcat ctgtaggaga cagaatcacc      60
atctcttgcc ggacaagtca gagccttagg agctatttac attggtatca gcaaaaacca    120
gggaaagccc ctaagctcct gatctatgct tcatccactt tacaaagtgg ggtcccatca    180
aggttcagtg gcagtggatc tgggacagat ttcactctca ccatcagcaa tctccaacct    240
gaagattttg caacttacta ctgtcaactg agtcggacgt tcggccaagg gaccaaggtg    300
gagatcaaac                                                           310
```

<210> SEQ ID NO 97
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

```
Asp Ile Gln Met Thr Gln Ser Pro Ser Ser Leu Ser Ala Ser Val Gly
1               5                   10                  15

Asp Arg Ile Thr Ile Ser Cys Arg Thr Ser Gln Ser Leu Arg Ser Tyr
            20                  25                  30

Leu His Trp Tyr Gln Gln Lys Pro Gly Lys Ala Pro Lys Leu Leu Ile
        35                  40                  45

Tyr Ala Ser Ser Thr Leu Gln Ser Gly Val Pro Ser Arg Phe Ser Gly
    50                  55                  60

Ser Gly Ser Gly Thr Asp Phe Thr Leu Thr Ile Ser Asn Leu Gln Pro
65                  70                  75                  80

Glu Asp Phe Ala Thr Tyr Tyr Cys Gln Leu Ser Arg Thr Phe Gly Gln
                85                  90                  95

Gly Thr Lys Val Glu Ile Lys
            100
```

<210> SEQ ID NO 98
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

```
Arg Thr Ser Gln Ser Leu Arg Ser Tyr Leu His
1               5                   10
```

<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

```
Ala Ser Ser Thr Leu Gln Ser
1               5
```

<210> SEQ ID NO 100
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

```
Gln Leu Ser Arg Thr
1               5
```

<210> SEQ ID NO 101
<211> LENGTH: 384
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 101

```
caggtccagc tgcagcagag cggcccagga ctggtcaagc cttcacagac actgagcctg      60
acatgcgcca ttagcggaga tagcgtgagc tcctacaatg ccgtgtggaa ctggatcagg     120
cagtctccaa gtcgaggact ggagtggctg ggacgaacat actatagatc cgggtggtac     180
aatgactatg ctgaatcagt gaaaagccga attactatca ccccgatac ctccaagaat      240 cagttctctc tgcagctgaa cagtgtgacc cctgaggaca cagccgtgta ctactgcgcc     300
agaagcggcc atatcaccgt ctttggcgtc aatgtggatg ctttcgatat gtgggggcag     360
gggactatgg tcaccgtgtc aagc                                             384
```

<210> SEQ ID NO 102
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 102

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Tyr
            20                  25                  30

Asn Ala Val Trp Asn Trp Ile Arg Gln Ser Pro Ser Arg Gly Leu Glu
        35                  40                  45

Trp Leu Gly Arg Thr Tyr Tyr Arg Ser Gly Trp Tyr Asn Asp Tyr Ala
    50                  55                  60

Glu Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Ser Gly His Ile Thr Val Phe Gly Val Asn Val
            100                 105                 110

Asp Ala Phe Asp Met Trp Gly Gln Gly Thr Met Val Thr Val Ser Ser
        115                 120                 125
```

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 103

```
Ser Tyr Asn Ala Val Trp Asn
1               5
```

<210> SEQ ID NO 104
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 104

Arg Thr Tyr Tyr Arg Ser Gly Trp Tyr Asn Asp Tyr Ala Glu Ser Val
1               5                   10                  15

Lys Ser

<210> SEQ ID NO 105
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ser Gly His Ile Thr Val Phe Gly Val Asn Val Asp Ala Phe Asp Met
1               5                   10                  15

<210> SEQ ID NO 106
<211> LENGTH: 309
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106
gatattcaga tgacccagag cccttccagc ctgtccgctt cagtggggga tcgagtgacc      60
attacctgcc gaaccagcca gagcctgagc tcctacacgc actggtatca gcagaagccc     120
ggcaaagccc ctaagctgct gatctacgcc gcttctagtc ggctgtccgg agtgccaagc     180
cggttctccg gatctgggag tggaaccgac tttaccctga caatttcaag cctgcagccc     240
gaggatttcg ctacatacta ctgtcagcag agcagaactt cgggcagggg cactaaggtg     300
gagatcaaa                                                            309

<210> SEQ ID NO 107
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Ser Leu Ser Ser Tyr
            20                  25                  30

Thr His Trp Tyr Gln Gln Lys Pro Gly Lys Ala Pro Lys Leu Leu Ile
        35                  40                  45

Tyr Ala Ala Ser Ser Arg Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Arg Thr Phe Gly Gln
                85                  90                  95

Gly Thr Lys Val Glu Ile Lys
            100

<210> SEQ ID NO 108
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Arg Thr Ser Gln Ser Leu Ser Ser Tyr Thr His
1               5                   10

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ala Ala Ser Ser Arg Leu Ser
1               5

<210> SEQ ID NO 110
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gln Gln Ser Arg Thr
1               5

<210> SEQ ID NO 111
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111
caggtccagc tgcagcagag cggcccccgga ctggtcaagc cttcacagac actgagcctg      60
acatgcgcca ttagcggaga tagcgtgagc tcctacaatg ccgtgtggaa ctggatcagg      120
cagtctccaa gtcgaggact ggagtggctg ggacgaacat actatagatc cgggtggtac      180
aatgactatg ctgaatcagt gaaaagccga attactatca accccgatac ctccaagaat      240
cagttctctc tgcagctgaa cagtgtgacc cctgaggaca cagccgtgta ctactgcgcc      300
agaagcggcc atatcaccgt ctttggcgtc aatgtggatg ctttcgatat gtgggggcag      360
gggactatgg tcaccgtgtc aagc                                             384

<210> SEQ ID NO 112
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Tyr
```

```
                        20                  25                  30

Asn Ala Val Trp Asn Trp Ile Arg Gln Ser Pro Ser Arg Gly Leu Glu
                35                  40                  45

Trp Leu Gly Arg Thr Tyr Tyr Arg Ser Gly Trp Tyr Asn Asp Tyr Ala
        50                  55                  60

Glu Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Ser Gly His Ile Thr Val Phe Gly Val Asn Val
            100                 105                 110

Asp Ala Phe Asp Met Trp Gly Gln Gly Thr Met Val Thr Val Ser Ser
        115                 120                 125

<210> SEQ ID NO 113
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Ser Tyr Asn Ala Val Trp Asn
1               5

<210> SEQ ID NO 114
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Arg Thr Tyr Tyr Arg Ser Gly Trp Tyr Asn Asp Tyr Ala Glu Ser Val
1               5                   10                  15

Lys Ser

<210> SEQ ID NO 115
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Ser Gly His Ile Thr Val Phe Gly Val Asn Val Asp Ala Phe Asp Met
1               5                   10                  15

<210> SEQ ID NO 116
<211> LENGTH: 309
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 116
gatattcaga tgacccagag cccttccagc ctgtccgctt cagtggggga tcgagtgacc     60
attacctgcc gaaccagcca gagcctgagc tcctacacgc actggtatca gcagaagccc    120
```

```
ggcaaagccc ctaagctgct gatctacgcc gcttctagtc gggggtccgg agtgccaagc      180
cggttctccg gatctgggag tggaaccgac tttaccctga caatttcaag cctgcagccc      240
gaggatttcg ctacatacta ctgtcagcag agcagaactt tcgggcaggg cactaaggtg      300
gagatcaaa                                                              309
```

<210> SEQ ID NO 117
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Ser Leu Ser Ser Tyr
            20                  25                  30

Thr His Trp Tyr Gln Gln Lys Pro Gly Lys Ala Pro Lys Leu Leu Ile
        35                  40                  45

Tyr Ala Ala Ser Ser Arg Gly Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Arg Thr Phe Gly Gln
                85                  90                  95

Gly Thr Lys Val Glu Ile Lys
            100

<210> SEQ ID NO 118
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Arg Thr Ser Gln Ser Leu Ser Ser Tyr Thr His
1               5                   10

<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ala Ala Ser Ser Arg Gly Ser
1               5

<210> SEQ ID NO 120
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gln Gln Ser Arg Thr
1               5

<210> SEQ ID NO 121
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121
caggtccagc tgcagcagag cggccccgga ctggtcaagc cttcacagac actgagcctg      60
acatgcgcca ttagcggaga tagcgtgagc tcctacaatg ccgtgtggaa ctggatcagg     120
cagtctccaa gtcgaggact ggagtggctg gacgaacat actatagatc cgggtggtac      180
aatgactatg ctgaatcagt gaaaagccga attactatca accccgatac ctccaagaat     240
cagttctctc tgcagctgaa cagtgtgacc cctgaggaca cagccgtgta ctactgcgcc     300
agaagcggcc atatcaccgt ctttggcgtc aatgtggatg ctttcgatat gtgggggcag     360
gggactatgg tcaccgtgtc aagc                                            384

<210> SEQ ID NO 122
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Tyr
                20                  25                  30

Asn Ala Val Trp Asn Trp Ile Arg Gln Ser Pro Ser Arg Gly Leu Glu
            35                  40                  45

Trp Leu Gly Arg Thr Tyr Tyr Arg Ser Gly Trp Tyr Asn Asp Tyr Ala
        50                  55                  60

Glu Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Ser Gly His Ile Thr Val Phe Gly Val Asn Val
            100                 105                 110

Asp Ala Phe Asp Met Trp Gly Gln Gly Thr Met Val Thr Val Ser Ser
        115                 120                 125

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ser Tyr Asn Ala Val Trp Asn
1               5

<210> SEQ ID NO 124

-continued

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Arg Thr Tyr Tyr Arg Ser Gly Trp Tyr Asn Asp Tyr Ala Glu Ser Val
1               5                   10                  15

Lys Ser

<210> SEQ ID NO 125
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Ser Gly His Ile Thr Val Phe Gly Val Asn Val Asp Ala Phe Asp Met
1               5                   10                  15

<210> SEQ ID NO 126
<211> LENGTH: 309
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 126
gatattcaga tgacccagag cccttccagc ctgtccgctt cagtggggga tcgagtgacc        60
attacctgcc gaaccagcca gagcctgagc tcctacgacc actggtatca gcagaagccc       120
ggcaaagccc ctaagctgct gatctacgcc gcttctagtc ggctgtccgg agtgccaagc       180
cggttctccg gatctgggag tggaaccgac tttacccctga caatttcaag cctgcagccc      240
gaggatttcg ctacatacta ctgtcagcag agcagaactt tcgggcaggg cactaaggtg       300
gagatcaaa                                                              309

<210> SEQ ID NO 127
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Ser Leu Ser Ser Tyr
                20                  25                  30

Asp His Trp Tyr Gln Gln Lys Pro Gly Lys Ala Pro Lys Leu Leu Ile
            35                  40                  45

Tyr Ala Ala Ser Ser Arg Leu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Arg Thr Phe Gly Gln
                85                  90                  95
```

Gly Thr Lys Val Glu Ile Lys
            100

<210> SEQ ID NO 128
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Arg Thr Ser Gln Ser Leu Ser Ser Tyr Asp His
1               5                   10

<210> SEQ ID NO 129
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ala Ala Ser Ser Arg Leu Ser
1               5

<210> SEQ ID NO 130
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gln Gln Ser Arg Thr
1               5

<210> SEQ ID NO 131
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 131
caggtccagc tgcagcagag cggcccccgga ctggtcaagc cttcacagac actgagcctg      60
acatgcgcca ttagcggaga tagcgtgagc tccaacaatg ccgtgtggaa ctggatcagg     120
cagtctccaa gtcgaggact ggagtggctg gacgaacat actatagatc caagtggtac      180
aatgactatg ctgaatcagt gaaaagccga attactatca accccgatac ctccaagaat     240
cagttctctc tgcagctgaa cagtgtgacc cctgaggaca cagccgtgta ctactgcgcc     300
agaagcggcc atatcaccgt ctttggcgtc aatgtggatg ctttcgatat gtgggggcag     360
gggaccacag tcaccgtctc ctca                                             384

<210> SEQ ID NO 132
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 132

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Asn Ala Val Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Glu Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Ser Gly His Ile Thr Val Phe Gly Val Asn Val
            100                 105                 110

Asp Ala Phe Asp Met Trp Gly Gln Gly Thr Thr Val Thr Val Ser Ser
        115                 120                 125

<210> SEQ ID NO 133
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ser Asn Asn Ala Val Trp Asn
1               5

<210> SEQ ID NO 134
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Arg Thr Tyr Tyr Arg Ser Lys Trp Tyr Asn Asp Tyr Ala Glu Ser Val
1               5                   10                  15

Lys Ser

<210> SEQ ID NO 135
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Ser Gly His Ile Thr Val Phe Gly Val Asn Val Asp Ala Phe Asp Met
1               5                   10                  15

<210> SEQ ID NO 136
<211> LENGTH: 309
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 136

```
gatattcaga tgacccagag cccttccagc ctgtccgctt cagtgggggga tcgagtgacc      60 attacctgcc gaaccagcca gagcctgagc tcctacacgc actggtatca gcagaagccc     120
ggcaaagccc ctaagctgct gatctacgcc gcttctagtc ggctgtccgg agtgccaagc     180
cggttctccg gatctgggag tggaaccgac tttacccctga caatttcaag cctgcagccc    240
gaggatttcg ctacatacta ctgtcagcag agcagaactt tcgggcaggg cactaaggtg     300
gagatcaaa                                                              309
```

<210> SEQ ID NO 137
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

```
Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Ser Leu Ser Ser Tyr
            20                  25                  30

Thr His Trp Tyr Gln Gln Lys Pro Gly Lys Ala Pro Lys Leu Leu Ile
        35                  40                  45

Tyr Ala Ala Ser Ser Arg Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Arg Thr Phe Gly Gln
                85                  90                  95

Gly Thr Lys Val Glu Ile Lys
            100
```

<210> SEQ ID NO 138
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

```
Arg Thr Ser Gln Ser Leu Ser Ser Tyr Thr His
1               5                   10
```

<210> SEQ ID NO 139
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

```
Ala Ala Ser Ser Arg Leu Ser
1               5
```

<210> SEQ ID NO 140
<211> LENGTH: 5
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 140

Gln Gln Ser Arg Thr
1               5

<210> SEQ ID NO 141
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 141
caggtccagc tgcagcagag cggccccgga ctggtcaagc cttcacagac actgagcctg      60
acatgcgcca ttagcggaga tagcgtgagc tccaacaatg ccgtgtggaa ctggatcagg     120
cagtctccaa gtcgaggact ggagtggctg ggacgaacat actatagatc caagtggtac     180
aatgactatg ctgaatcagt gaaaagccga attactatca accccgatac tccaagaat     240 cagttctctc tgcagctgaa cagtgtgacc cctgaggaca cagccgtgta ctactgcgcc     300
agaagcggcc atatcaccgt ctttggcgtc aatgtggatg ctttcgatat gtggggggcag    360 gggaccacag tcaccgtctc ctca                                            384

<210> SEQ ID NO 142
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Asn Ala Val Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Glu Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Ser Gly His Ile Thr Val Phe Gly Val Asn Val
            100                 105                 110

Asp Ala Phe Asp Met Trp Gly Gln Gly Thr Thr Val Thr Val Ser Ser
        115                 120                 125

<210> SEQ ID NO 143
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Ser Asn Asn Ala Val Trp Asn
1               5

<210> SEQ ID NO 144
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Arg Thr Tyr Tyr Arg Ser Lys Trp Tyr Asn Asp Tyr Ala Glu Ser Val
1               5                   10                  15

Lys Ser

<210> SEQ ID NO 145
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ser Gly His Ile Thr Val Phe Gly Val Asn Val Asp Ala Phe Asp Met
1               5                   10                  15

<210> SEQ ID NO 146
<211> LENGTH: 309
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 146
gatattcaga tgacccagag cccttccagc ctgtccgctt cagtggggga tcgagtgacc      60
attacctgcc gaaccagcca gagcctgagy tcctacacgc actggtatca gcagaagccc     120
ggcaaagccc ctaagctgct gatctacgcc gcttctagtc gggggtccgg agtgccaagc     180
cggttctccg gatctgggag tggaaccgac tttacccctga caatttcaag cctgcagccc     240
gaggatttcg ctacatacta ctgtcagcag agcagaactt tcgggcaggg cactaaggtg     300
gagatcaaa                                                             309

<210> SEQ ID NO 147
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Asp Ile Gln Met Thr Gln Ser Pro Ser Leu Ser Ala Ser Val Gly
1               5                   10                  15

Asp Arg Val Thr Ile Thr Cys Arg Thr Ser Gln Ser Leu Ser Ser Tyr
                20                  25                  30

Thr His Trp Tyr Gln Gln Lys Pro Gly Lys Ala Pro Lys Leu Leu Ile
            35                  40                  45

Tyr Ala Ala Ser Ser Arg Gly Ser Gly Val Pro Ser Arg Phe Ser Gly

```
                    50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Arg Thr Phe Gly Gln
                 85                  90                  95

Gly Thr Lys Val Glu Ile Lys
            100
```

<210> SEQ ID NO 148
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

```
Arg Thr Ser Gln Ser Leu Ser Ser Tyr Thr His
 1               5                  10
```

<210> SEQ ID NO 149
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

```
Ala Ala Ser Ser Arg Gly Ser
 1               5
```

<210> SEQ ID NO 150
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

```
Gln Gln Ser Arg Thr
 1               5
```

<210> SEQ ID NO 151
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 151

```
caggtccagc tgcagcagag cggccccgga ctggtcaagc cttcacagac actgagcctg      60
acatgcgcca ttagcggaga tagcgtgagc tccaacaatg ccgtgtggaa ctggatcagg     120
cagtctccaa gtcgaggact ggagtggctg ggacgaacat actatagatc caagtggtac     180
aatgactatg ctgaatcagt gaaaagccga attactatca accccgatac ctccaagaat     240
cagttctctc tgcagctgaa cagtgtgacc cctgaggaca cagccgtgta ctactgcgcc     300
agaagcggcc atatcaccgt ctttggcgtc aatgtggatg ctttcgatat gtggggggcag     360 gggaccacag tcaccgtctc ctca                                             384
```

-continued

```
<210> SEQ ID NO 152
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Asn Ala Val Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Glu Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Ser Gly His Ile Thr Val Phe Gly Val Asn Val
            100                 105                 110

Asp Ala Phe Asp Met Trp Gly Gln Gly Thr Thr Val Thr Val Ser Ser
        115                 120                 125

<210> SEQ ID NO 153
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ser Asn Asn Ala Val Trp Asn
1               5

<210> SEQ ID NO 154
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Arg Thr Tyr Tyr Arg Ser Lys Trp Tyr Asn Asp Tyr Ala Glu Ser Val
1               5                   10                  15

Lys Ser

<210> SEQ ID NO 155
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Ser Gly His Ile Thr Val Phe Gly Val Asn Val Asp Ala Phe Asp Met
1               5                   10                  15
```

-continued

```
<210> SEQ ID NO 156
<211> LENGTH: 309
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 156
gatattcaga tgacccagag cccttccagc ctgtccgctt cagtggggga tcgagtgacc      60
attacctgcc gaaccagcca gagcctgagc tcctacctgc actggtatca gcagaagccc     120
ggcaaagccc ctaagctgct gatctacgcc gcttctagtc tgcagtccgg agtgccaagc     180
cggttctccg gatctgggag tggaaccgac tttaccctga caatttcaag cctgcagccc     240
gaggatttcg ctacatacta ctgtcagcag agcagaactt cgggcaggg cactaaggtg      300 gagatcaaa                                                             309

<210> SEQ ID NO 157
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Ser Leu Ser Ser Tyr
            20                  25                  30

Leu His Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Arg Thr Phe Gly Gln
                85                  90                  95

Gly Thr Lys Val Glu Ile Lys
            100

<210> SEQ ID NO 158
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Arg Thr Ser Gln Ser Leu Ser Ser Tyr Leu His
1               5                   10

<210> SEQ ID NO 159
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159
```

```
Ala Ala Ser Ser Leu Gln Ser
1               5

<210> SEQ ID NO 160
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Gln Gln Ser Arg Thr
1               5

<210> SEQ ID NO 161
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Asn or Tyr
<220> FEATURE:
<221> NAME/KEY: MOD_RES
<222> LOCATION: (3)..(3)
<223> OTHER INFORMATION: Asn, Ser or Arg
<220> FEATURE:
<221> NAME/KEY: MOD_RES
<222> LOCATION: (5)..(5)
<223> OTHER INFORMATION: Val or Thr

<400> SEQUENCE: 161

Ser Xaa Xaa Ala Xaa Trp Asn
1               5

<210> SEQ ID NO 162
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Lys or Gly
<220> FEATURE:
<221> NAME/KEY: MOD_RES
<222> LOCATION: (10)..(10)
<223> OTHER INFORMATION: Asn or Tyr
<220> FEATURE:
<221> NAME/KEY: MOD_RES
<222> LOCATION: (14)..(14)
<223> OTHER INFORMATION: Glu, Val or Asp
<220> FEATURE:
<221> NAME/KEY: MOD_RES
<222> LOCATION: (15)..(15)
<223> OTHER INFORMATION: Ser or Phe
<220> FEATURE:
<221> NAME/KEY: MOD_RES
<222> LOCATION: (16)..(16)
<223> OTHER INFORMATION: Val or Leu

<400> SEQUENCE: 162

Arg Thr Tyr Tyr Arg Ser Xaa Trp Tyr Xaa Asp Tyr Ala Xaa Xaa Xaa
1               5                   10                  15

Lys
```

```
<210> SEQ ID NO 163
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Gly
<220> FEATURE:
<221> NAME/KEY: MOD_RES
<222> LOCATION: (6)..(6)
<223> OTHER INFORMATION: Val or Glu
<220> FEATURE:
<221> NAME/KEY: MOD_RES
<222> LOCATION: (9)..(9)
<223> OTHER INFORMATION: Val or Leu
<220> FEATURE:
<221> NAME/KEY: MOD_RES
<222> LOCATION: (11)..(11)
<223> OTHER INFORMATION: Val or Ile
<220> FEATURE:
<221> NAME/KEY: MOD_RES
<222> LOCATION: (14)..(14)
<223> OTHER INFORMATION: Phe or Tyr
<220> FEATURE:
<221> NAME/KEY: MOD_RES
<222> LOCATION: (16)..(16)
<223> OTHER INFORMATION: Met, Ile or Val

<400> SEQUENCE: 163

Xaa Gly His Ile Thr Xaa Phe Gly Xaa Asn Xaa Asp Ala Xaa Asp Xaa
1               5                   10                  15

<210> SEQ ID NO 164
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Thr, Ala or absent
<220> FEATURE:
<221> NAME/KEY: MOD_RES
<222> LOCATION: (3)..(3)
<223> OTHER INFORMATION: Ser or Ala
<220> FEATURE:
<221> NAME/KEY: MOD_RES
<222> LOCATION: (5)..(5)
<223> OTHER INFORMATION: Ser or Arg
<220> FEATURE:
<221> NAME/KEY: MOD_RES
<222> LOCATION: (7)..(7)
<223> OTHER INFORMATION: Ser, Asn or Arg
<220> FEATURE:
<221> NAME/KEY: MOD_RES
<222> LOCATION: (10)..(10)
<223> OTHER INFORMATION: Leu, Thr or Asp

<400> SEQUENCE: 164

Arg Xaa Xaa Gln Xaa Leu Xaa Ser Tyr Xaa His
1               5                   10

<210> SEQ ID NO 165
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
                          peptide
<220> FEATURE:
<221> NAME/KEY: MOD_RES
<222> LOCATION: (2)..(2)
<223> OTHER INFORMATION: Ala, Thr or Ser
<220> FEATURE:
<221> NAME/KEY: MOD_RES
<222> LOCATION: (3)..(4)
<223> OTHER INFORMATION: Ser or Thr
<220> FEATURE:
<221> NAME/KEY: MOD_RES
<222> LOCATION: (5)..(5)
<223> OTHER INFORMATION: Leu or Arg
<220> FEATURE:
<221> NAME/KEY: MOD_RES
<222> LOCATION: (6)..(6)
<223> OTHER INFORMATION: Gln, Leu or Gly

<400> SEQUENCE: 165

Ala Xaa Xaa Xaa Xaa Xaa Ser
1               5

<210> SEQ ID NO 166
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gln or Leu

<400> SEQUENCE: 166

Gln Xaa Ser Arg Thr
1               5

<210> SEQ ID NO 167
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Asn Ala Val Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Glu Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Ser Gly His Ile Thr Val Phe Gly Val Asn Val
            100                 105                 110

Asp Ala Phe Asp Met Trp Gly Gln Gly Thr Met Val Thr Val Ser Ser
        115                 120                 125

<210> SEQ ID NO 168
<211> LENGTH: 103
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Ser Leu Ser Ser Tyr
            20                  25                  30

Leu His Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Arg Thr Phe Gly Gln
                85                  90                  95

Gly Thr Lys Val Glu Ile Lys
            100

<210> SEQ ID NO 169
<211> LENGTH: 221
<212> TYPE: PRT
<213> ORGANISM: Influenza A virus

<400> SEQUENCE: 169

Gly Ile Phe Gly Ala Ile Ala Gly Phe Ile Glu Asn Gly Trp Glu Gly
1               5                   10                  15

Met Val Asp Gly Trp Tyr Gly Phe Arg His Gln Asn Ser Glu Gly Ile
            20                  25                  30

Gly Gln Ala Ala Asp Leu Lys Ser Thr Gln Ala Ala Ile Asn Gln Ile
        35                  40                  45

Asn Gly Lys Leu Asn Arg Leu Ile Gly Lys Thr Asn Glu Lys Phe His
    50                  55                  60

Gln Ile Glu Lys Glu Phe Ser Glu Val Glu Gly Arg Ile Gln Asp Leu
65                  70                  75                  80

Glu Lys Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Leu Thr Asp
            100                 105                 110

Ser Glu Met Asn Lys Leu Phe Glu Arg Thr Lys Lys Gln Leu Arg Glu
        115                 120                 125

Asn Ala Glu Asp Met Gly Asn Gly Cys Phe Lys Ile Tyr His Lys Cys
    130                 135                 140

Asp Asn Ala Cys Ile Gly Ser Ile Arg Asn Gly Thr Tyr Asp His Asp
145                 150                 155                 160

Val Tyr Arg Asp Glu Ala Leu Asn Asn Arg Phe Gln Ile Lys Gly Val
                165                 170                 175

Glu Leu Lys Ser Gly Tyr Lys Asp Trp Ile Leu Trp Ile Ser Phe Ala
            180                 185                 190

Ile Ser Cys Phe Leu Leu Cys Val Ala Leu Leu Gly Phe Ile Met Trp
        195                 200                 205

Ala Cys Gln Lys Gly Asn Ile Arg Cys Asn Ile Cys Ile
    210                 215                 220

<210> SEQ ID NO 170
<211> LENGTH: 221
<212> TYPE: PRT
<213> ORGANISM: Influenza A virus

<400> SEQUENCE: 170

Gly Ile Phe Gly Ala Ile Ala Gly Phe Ile Glu Asn Gly Trp Glu Gly
1               5                   10                  15

Met Val Asp Gly Trp Tyr Gly Phe Arg His Gln Asn Ser Glu Gly Thr
            20                  25                  30

Gly Gln Ala Ala Asp Leu Lys Ser Thr Gln Ala Ala Ile Asn Gln Ile
        35                  40                  45

Asn Gly Lys Leu Asn Arg Leu Ile Glu Lys Thr Asn Glu Lys Phe His
    50                  55                  60

Gln Ile Glu Lys Glu Phe Ser Glu Val Glu Gly Arg Ile Gln Asp Leu
65                  70                  75                  80

Glu Lys Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Leu Thr Asp
            100                 105                 110

Ser Glu Met Asn Lys Leu Phe Glu Arg Thr Lys Lys Gln Leu Arg Glu
        115                 120                 125

Asn Ala Glu Asp Met Gly Asn Gly Cys Phe Lys Ile Tyr His Lys Cys
    130                 135                 140

Asp Asn Ala Cys Ile Gly Ser Ile Arg Asn Gly Thr Tyr Asp His Asp
145                 150                 155                 160

Val Tyr Arg Asp Glu Ala Leu Asn Asn Arg Phe Gln Ile Lys Gly Val
                165                 170                 175

Glu Leu Lys Ser Gly Tyr Lys Asp Trp Ile Leu Trp Ile Ser Phe Ala
            180                 185                 190

Ile Ser Cys Phe Leu Leu Cys Val Val Leu Leu Gly Phe Ile Met Trp
        195                 200                 205

Ala Cys Gln Lys Gly Asn Ile Arg Cys Asn Ile Cys Ile
    210                 215                 220

<210> SEQ ID NO 171
<211> LENGTH: 221
<212> TYPE: PRT
<213> ORGANISM: Influenza A virus

<400> SEQUENCE: 171

Gly Leu Phe Gly Ala Ile Ala Gly Phe Ile Glu Asn Gly Trp Glu Gly
1               5                   10                  15

Met Ile Asp Gly Trp Tyr Gly Phe Arg His Gln Asn Ser Glu Gly Thr
            20                  25                  30

Gly Gln Ala Ala Asp Leu Lys Ser Thr Gln Ala Ala Ile Asp Gln Ile
        35                  40                  45

Asn Gly Lys Leu Asn Arg Val Ile Glu Lys Thr Asn Glu Lys Phe His
    50                  55                  60

Gln Ile Glu Lys Glu Phe Ser Glu Val Glu Gly Arg Ile Gln Asp Leu
65                  70                  75                  80

Glu Lys Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Leu Thr Asp
            100                 105                 110

```
Ser Glu Met Asn Lys Leu Phe Glu Lys Thr Arg Arg Gln Leu Arg Glu
            115                 120                 125

Asn Ala Glu Glu Met Gly Asn Gly Cys Phe Lys Ile Tyr His Lys Cys
        130                 135                 140

Asp Asn Ala Cys Ile Glu Ser Ile Arg Asn Gly Thr Tyr Asp His Asp
145                 150                 155                 160

Val Tyr Arg Asp Glu Ala Leu Asn Asn Arg Phe Gln Ile Lys Gly Val
                165                 170                 175

Glu Leu Lys Ser Gly Tyr Lys Asp Trp Ile Leu Trp Ile Ser Phe Ala
            180                 185                 190

Ile Ser Cys Phe Leu Leu Cys Val Val Leu Leu Gly Phe Ile Met Trp
        195                 200                 205

Ala Cys Gln Arg Gly Asn Ile Arg Cys Asn Ile Cys Ile
        210                 215                 220

<210> SEQ ID NO 172
<211> LENGTH: 221
<212> TYPE: PRT
<213> ORGANISM: Influenza A virus

<400> SEQUENCE: 172

Gly Leu Phe Gly Ala Ile Ala Gly Phe Ile Glu Asn Gly Trp Glu Gly
1               5                   10                  15

Met Ile Asp Gly Trp Tyr Gly Phe Arg His Gln Asn Ser Glu Gly Thr
            20                  25                  30

Gly Gln Ala Ala Asp Leu Lys Ser Thr Gln Ala Ala Ile Asp Gln Ile
        35                  40                  45

Asn Gly Lys Leu Asn Arg Val Ile Glu Lys Thr Asn Glu Lys Phe His
    50                  55                  60

Gln Ile Glu Lys Glu Phe Ser Glu Val Glu Gly Arg Ile Gln Asp Leu
65                  70                  75                  80

Glu Lys Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Leu Thr Asp
            100                 105                 110

Ser Glu Met Asn Lys Leu Phe Glu Lys Thr Arg Arg Gln Leu Arg Glu
            115                 120                 125

Asn Ala Glu Asp Met Gly Asn Gly Cys Phe Lys Ile Tyr His Lys Cys
        130                 135                 140

Asp Asn Ala Cys Ile Glu Ser Ile Arg Asn Gly Thr Tyr Asp His Asp
145                 150                 155                 160

Val Tyr Arg Asp Glu Ala Leu Asn Asn Arg Phe Gln Ile Lys Gly Val
                165                 170                 175

Glu Leu Lys Ser Gly Tyr Lys Asp Trp Ile Leu Trp Ile Ser Phe Ala
            180                 185                 190

Ile Ser Cys Phe Leu Leu Cys Val Val Leu Leu Gly Phe Ile Met Trp
        195                 200                 205

Ala Cys Gln Arg Gly Asn Ile Arg Cys Asn Ile Cys Ile
        210                 215                 220
```